US006509156B1

(12) United States Patent
Stewart et al.

(10) Patent No.: US 6,509,156 B1
(45) Date of Patent: Jan. 21, 2003

(54) **DNA CLONING METHOD RELYING ON THE *E. COLI* RECE/RECT RECOMBINATION SYSTEM**

(75) Inventors: Francis Stewart, Leimen; Youming Zhang, Heidelberg; Frank Buchholz, Bremen, all of (DE)

(73) Assignee: Europaisches Laboratorium Fur Molekularoiologie (EMBL), Heidelberg (DE)

( * ) Notice: Subject to any disclaimer, the term of this patent is extended or adjusted under 35 U.S.C. 154(b) by 0 days.

(21) Appl. No.: 09/555,510

(22) PCT Filed: Dec. 7, 1998

(86) PCT No.: PCT/EP98/07945

§ 371 (c)(1),
(2), (4) Date: Jun. 5, 2000

(87) PCT Pub. No.: WO99/29837

PCT Pub. Date: Jun. 17, 1999

(30) Foreign Application Priority Data

Dec. 5, 1997 (EP) .............................. 97121462
Oct. 5, 1998 (EP) ............................. 98118756

(51) Int. Cl.[7] .............................. C12Q 1/68; C12N 1/20; C12N 1/00; C12N 15/00; C12N 15/09; C12N 15/63; C12N 15/70; C12N 15/74
(52) U.S. Cl. ...................... 435/6; 435/252.3; 435/320.1
(58) Field of Search ..................... 435/6, 252.3, 320.1

(56) References Cited

FOREIGN PATENT DOCUMENTS

WO    WO 95/22625    *   8/1995

OTHER PUBLICATIONS

GeneBank Accession No. V00638, "Lambda genome from map unit 74 backward to map unit 67" (1995).*
Stratagene Catalog, p. 39 (1988).*
Hall, D. S. et al., "Homologous pairing and strand exchange promoted by the *Escherichia coli* RecT protein", PNAS USA, vol. 91, pp. 3205–3209 (1994).*
Oliner et al., "In vivo cloning of PCR Products in *E. coli*", Nucleic Acids Research, vol 21. No. 22, 1993, pp. 5192–5197.
Nussbaum et al., "Restriction–stimulated recombination of plasmids by the RecE pathway of *Escherichia coli*", Genetics, vol. 130, No. 1, Jan. 1992, pp.37–49.
Zhang et al., "A new logic for DNA engineering using recombination in *Escherichia coli*", Nature Genetics, vol. 20, No. 2, Oct. 1998, pp. 123–128.
Kolodner et al., "Homologous pairing proteins encoded by the *Escherichia coli* recE and recT genes" Molecular Microbiology, vol. 11, No. 1. 1994. pp. 23–30.
Luisi–Deluca et al., "Genetic and physical analysis of plasmid recombination in recB recC scbB and recB reC scbA *Escherichia coli* K–12 mutants", Genetics, vol. 122, 19889, pp. 269–278.

(List continued on next page.)

*Primary Examiner*—Kenneth R. Horlick
*Assistant Examiner*—Teresa Strzelecka

(57) ABSTRACT

The invention relates to methods for cloning DNA molecules using recE/recT-mediated homologous recombination mechanism between at least two DNA molecules where one DNA molecule is a circular or linear DNA molecule and the second DNA molecule is a circular DNA molecule, and the second DNA molecule contains two regions with sequence homology to the first DNA molecule. Competent cells and vectors are also described.

61 Claims, 65 Drawing Sheets

OTHER PUBLICATIONS

Figure 1:
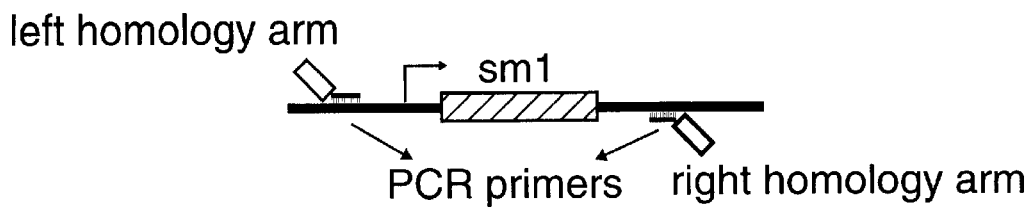
Figure 1:
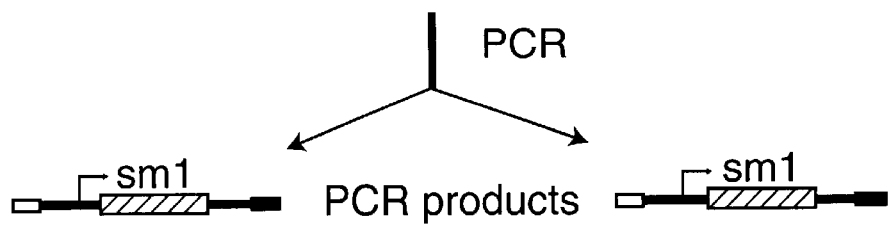
Figure 1:
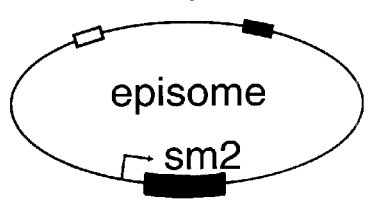
Figure 1:
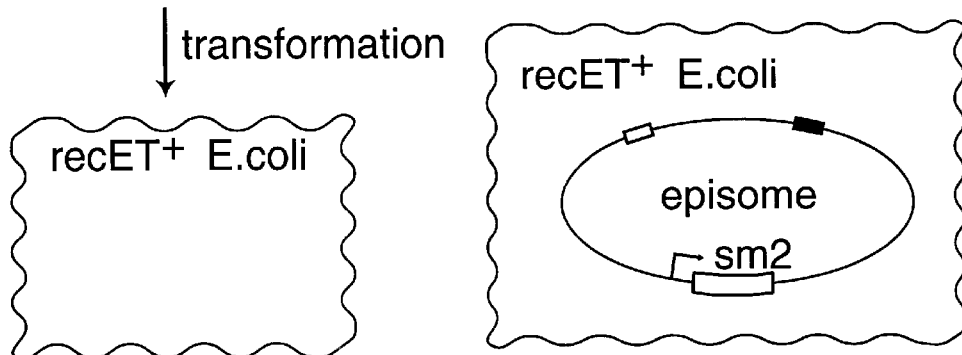
Figure 1:
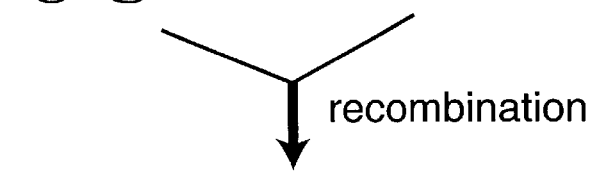
Figure 1:
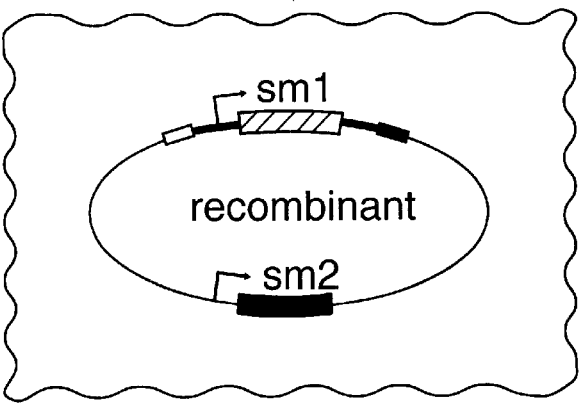

Degryse et al, "Evaluation of *Escherichia coli* recBC sbcBC mutants for cloning by recombination in vivo", Journal of Biotechnology, vol. 2, No. 39, Apr. 15, 1995, pp. 181–187.

Yang et al., "Homologous recombination based modification in *Escherichia coli* and germ line transmission in transgenic mice of a bacterial artificial chromosome", Nature Biotechnology, vol. 15, Sep. 1997, pp. 859–865.

Murphy, "Lambda Gam protein inhibits the helicase and Chi–stimulated recombination activities of *Escherichia coli* RecBD enzyme", Journal of Bacteriology, vol. 173, No. 18, Sep. 1991, pp. 5808–5821.

* cited by examiner

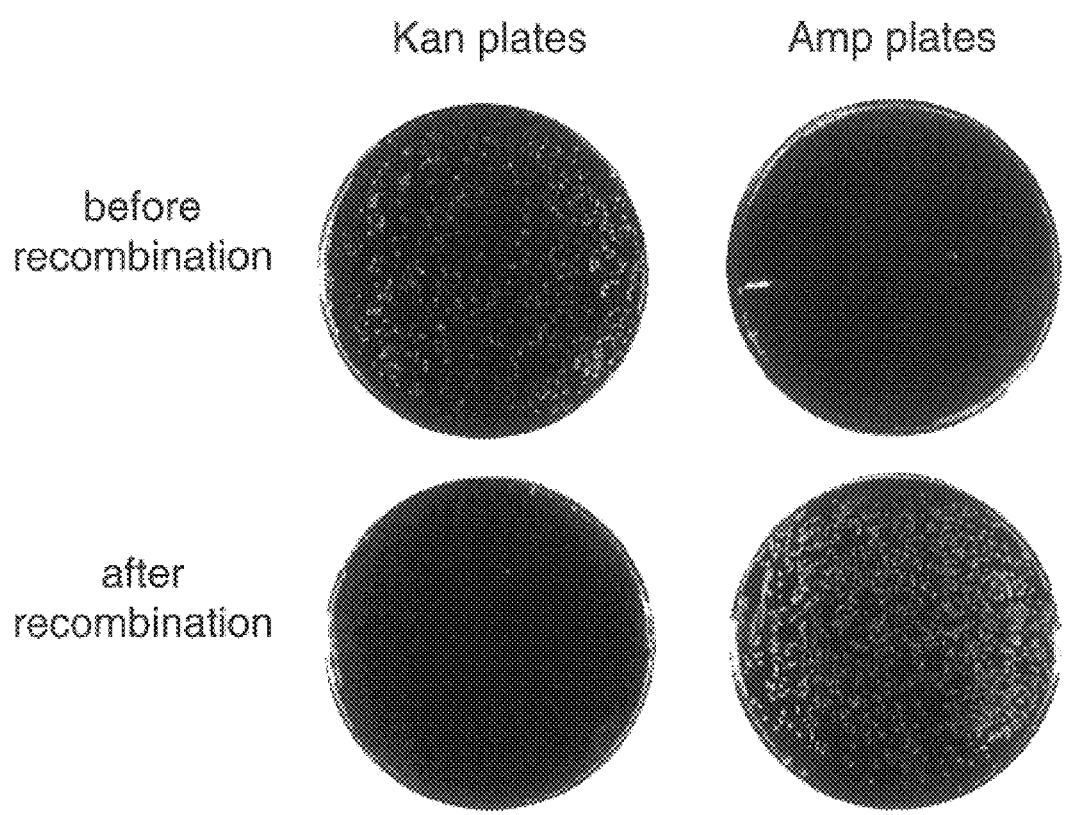

P1 DNA digested with EcoRI | hybridized with a bla probe (Amp) | hybridized with a Hoxa-1 probe Lane 1: 1 of p1-Hox clone in NS3145 original bacterial strain (Kan resistance)
Lane 2-3: 2 of p1-Hox cloned in JC9604 before homologous recombination *Kan resistance)
Lane 4-6: 3 of P1-Hox clones in JC9604 after homologous recombination (Amp resistance)

Pvu II digestion pZero-2.1 alone pZero-2.1 + PCR products

IPTG + Kan

JC5547
(recA⁻, recB⁻, recC⁻)

+

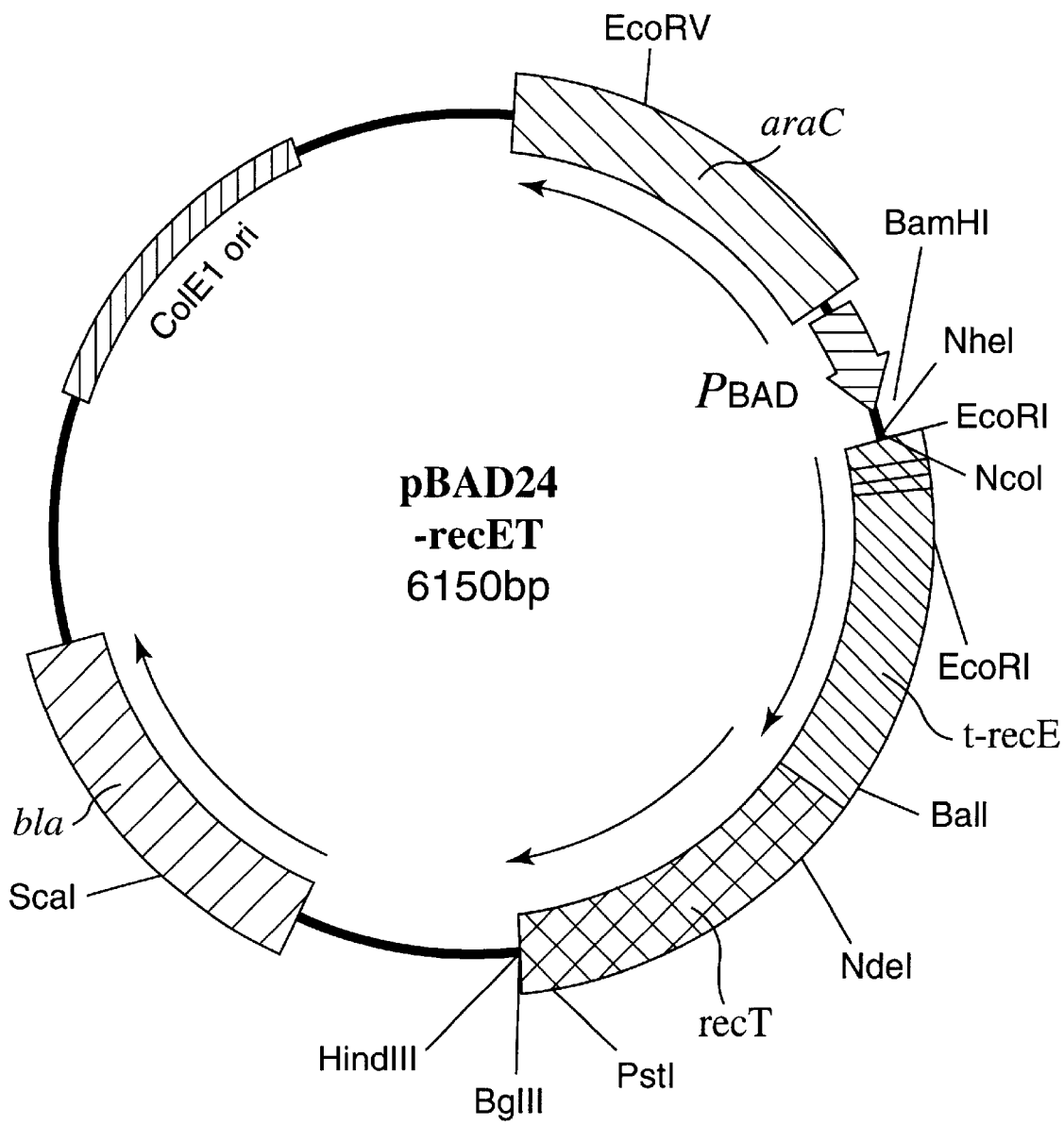
t-recE---truncated recE (from 588 aa ---> end. 866 aa)

Fig.7b

```
  1 ATCGATGCATAATGTGCCTGTCAAATGGACGAAGCAGGGATTC

44 TGCAAACCCTATGCTACTCCGTCAAGCCGTCAATTGTCTGATT

87 CGTTACCAA TTA TGA CAA CTT GAC GGC TAC ATC
         293◄ • • •  Ser Leu Lys Val Ala Val Asp

120 ATT CAC TTT TTC TTC ACA ACC GGC ACG GAA CTC
285◄Asn Val Lys Glu Glu Cys Gly Ala Arg Phe Glu

153 GCT CGG GCT GGC CCC GGT GCA TTT TTT AAA TAC
274◄Ser Pro Ser Ala Gly Thr Cys Lys Lys Phe Val

186 CCG CGA GAA ATA GAG TTG ATC GTC AAA ACC AAC
263◄Arg Ser Phe Tyr Leu Gln Asp Asp Phe Gly Val

219 ATT GCG ACC GAC GGT GGC GAT AGG CAT CCG GGT
252◄Asn Arg Gly Val Thr Ala Ile Pro Met Arg Thr

252 GGT GCT CAA AAG CAG CTT CGC CTG GCT GAT ACG
241◄Thr Ser Leu Leu Leu Lys Ala Gln Ser Ile Arg

285 TTG GTC CTC GCG CCA GCT TAA GAC GCT AAT CCC
230◄Gln Asp Glu Arg Trp Ser Leu Val Ser Ile Gly

318 TAA CTG CTG GCG GAA AAG ATG TGA CAG ACG CGA
219◄Leu Gln Gln Arg Phe Leu His Ser Leu Arg Ser

351 CGG CGA CAA GCA AAC ATG CTG TGC GAC GCT GGC
208◄Pro Ser Leu Cys Val His Gln Ala Val Ser Ala
      EcoRV
384 GAT ATC AAA ATT GCT GTC TGC CAG GTG ATC GCT
197◄Ile Asp Phe Asn Ser Asp Ala Leu His Asp Ser

417 GAT GTA CTG ACA AGC CTC GCG TAC CCG ATT ATC
186◄Ile Tyr Gln Cys Ala Glu Arg Val Arg Asn Asp
```

Fig.7c

```
450  CAT CGG TGG ATG GAG CGA CTC GTT AAT CGC TTC
175◄Met Pro Pro His Leu Ser Glu Asn Ile Ala Glu

483  CAT GCG CCG CAG TAA CAA TTG CTC AAG CAG ATT
164◄Met Arg Arg Leu Leu Leu Gln Glu Leu Leu Asn

516  TAT CGC CAG CAG CTC CGA ATA GCG CCC TTC CCC
153◄Ile Ala Leu Leu Glu Ser Tyr Arg Gly Glu Gly

549  TTG CCC GGC GTT AAT GAT TTG CCC AAA CAG GTC
142◄Gln Gly Ala Asn Ile Ile Gln Gly Phe Leu Asp

582  GCT GAA ATG CGG CTG GTG CGC TTC ATC CGG GCG
131◄Ser Phe His Pro Gln His Ala Glu Asp Pro Arg

615  AAA GAA CCC CGT ATT GGC AAA TAT TGA CGG CCA
120◄Phe Phe Gly Thr Asn Ala Phe Ile Ser Pro Trp

648  GTT AAG CCA TTC ATG CCA GTA GGC GCG CGG ACG
109◄Asn Leu Trp Glu His Trp Tyr Ala Arg Pro Arg

681  AAA GTA AAC CCA CTG GTG ATA CCA TTC GCG AGC
 98◄Phe Tyr Val Trp Gln His Tyr Trp Glu Arg Ala

714  CTC CGG ATG ACG ACC GTA GTG ATG AAT CTC TCC
 87◄Glu Pro His Arg Gly Tyr His His Ile Glu Gly

747  TGG CGG GAA CAG CAA AAT ATC ACC CGG TCG GCA
 76◄Pro Pro Phe Leu Leu Ile Asp Gly Pro Arg Cys

780  AAC AAA TTC TCG TCC CTG ATT TTT CAC CAC CCC
 65◄Val Phe Glu Arg Gly Gln Asn Lys Val Val Gly

813  CTG ACC GCG AAT GGT GAG ATT GAG AAT ATA ACC
 54◄Gln Gly Arg Ile Thr Leu Asn Leu Ile Tyr Gly

846  TTT CAT TCC CAG CGG TCG GTC GAT AAA AAA ATC
 43◄Lys Met Gly Leu Pro Arg Asp Ile Phe Phe Asp
```

Fig.7d

```
 879 GAG ATA ACC GTT GGC CTC AAT CGG CGT TAA ACC
  32◄Leu Tyr Gly Asn Ala Glu Ile Pro Thr Leu Gly

912 CGC CAC CAG ATG GGC ATT AAA CGA GTA TCC CGG
  21◄Ala Val Leu His Ala Asn Phe Ser Tyr Gly Pro

945 CAG CAG GGG ATC ATT TTG CGC TTC AGC CAT
  10◄Leu Leu Pro Asp Asn Gln Ala Glu Ala Met

975 ACTTTTCATA CTCCCGCCAT TCAGAGAAGA AACCAATTGT
1015 CCATATTGCA TCAGACATTG CCGTCACTGC GTCTTTTACT
1055 GGCTCTTCTC GCTAACCAAA CCGGTAACCC CGCTTATTAA
1095 AAGCATTCTG TAACAAAGCG GGACCAAAGC CATGACAAAA
1135 ACGCGTAACA AAGTGTCTA TAATCACGGC AGAAAAGTCC
1175 ACATTGATTA TTTGCACGGC GTCACACTTT GCTATGCCAT
                                        BamHI
1215 AGCATTTTTA TCCATAAGAT TAGCGGATCC TACCTGACGC
1255 TTTTTATCGC AACTCTCTAC TGTTTCTCCA TACCCGTTTT
         NheI           EcoRI       NcoI
1295 TTTGGGCTAG CAGGAGGAAT TCACC ATG GAT CCC GTA

1►Met Asp Pro Val

1332 ATC GTA GAA GAC ATA GAG CCA GGT ATT TAT TAC
  5►Ile Val Glu Asp Ile Glu Pro Gly Ile Tyr Tyr

1365 GGA ATT TCG AAT GAG AAT TAC CAC GCG GGT CCC
 16►Gly Ile Ser Asn Glu Asn Tyr His Ala Gly Pro

1398 GGT ATC AGT AAG TCT CAG CTC GAT GAC ATT GCT
```

Fig.7e

```
  27▶ Gly  Ile  Ser  Lys  Ser  Gln  Leu  Asp  Asp  Ile  Ala
1431  GAT  ACT  CCG  GCA  CTA  TAT  TTG  TGG  CGT  AAA  AAT

38▶ Asp  Thr  Pro  Ala  Leu  Tyr  Leu  Trp  Arg  Lys  Asn
1464  GCC  CCC  GTG  GAC  ACC  ACA  AAG  ACA  AAA  ACG  CTC

49▶ Ala  Pro  Val  Asp  Thr  Thr  Lys  Thr  Lys  Thr  Leu
1497  GAT  TTA  GGA  ACT  GCT  TTC  CAC  TGC  CGG  GTA  CTT

60▶ Asp  Leu  Gly  Thr  Ala  Phe  His  Cys  Arg  Val  Leu
                       EcoRI
1530  GAA  CCG  GAA  GAA  TTC  AGT  AAC  CGC  TTT  ATC  GTA

71▶ Glu  Pro  Glu  Glu  Phe  Ser  Asn  Arg  Phe  Ile  Val
1563  GCA  CCT  GAA  TTT  AAC  CGC  CGT  ACA  AAC  GCC  GGA

82▶ Ala  Pro  Glu  Phe  Asn  Arg  Arg  Thr  Asn  Ala  Gly
1596  AAA  GAA  GAA  GAG  AAA  GCG  TTT  CTG  ATG  GAA  TGC

93▶ Lys  Glu  Glu  Glu  Lys  Ala  Phe  Leu  Met  Glu  Cys
1629  GCA  AGC  ACA  GGA  AAA  ACG  GTT  ATC  ACT  GCG  GAA

104▶ Ala  Ser  Thr  Gly  Lys  Thr  Val  Ile  Thr  Ala  Glu
1662  GAA  GGC  CGG  AAA  ATT  GAA  CTC  ATG  TAT  CAA  AGC

115▶ Glu  Gly  Arg  Lys  Ile  Glu  Leu  Met  Tyr  Gln  Ser
```

Fig.7f

```
1695  GTT  ATG  GCT  TTG  CCG  CTG  GGG  CAA  TGG  CTT  GTT

126▶  Val  Met  Ala  Leu  Pro  Leu  Gly  Gln  Trp  Leu  Val

1728  GAA  AGC  GCC  GGA  CAC  GCT  GAA  TCA  TCA  ATT  TAC

137▶  Glu  Ser  Ala  Gly  His  Ala  Glu  Ser  Ser  Ile  Tyr

1761  TGG  GAA  GAT  CCT  GAA  ACA  GGA  ATT  TTG  TGT  CGG

148▶  Trp  Glu  Asp  Pro  Glu  Thr  Gly  Ile  Leu  Cys  Arg

1794  TGC  CGT  CCG  GAC  AAA  ATT  ATC  CCT  GAA  TTT  CAC

159▶  Cys  Arg  Pro  Asp  Lys  Ile  Ile  Pro  Glu  Phe  His

1827  TGG  ATC  ATG  GAC  GTG  AAA  ACT  ACG  GCG  GAT  ATT

170▶  Trp  Ile  Met  Asp  Val  Lys  Thr  Thr  Ala  Asp  Ile

1860  CAA  CGA  TTC  AAA  ACC  GCT  TAT  TAC  GAC  TAC  CGC

181▶  Gln  Arg  Phe  Lys  Thr  Ala  Tyr  Tyr  Asp  Tyr  Arg

1893  TAT  CAC  GTT  CAG  GAT  GCA  TTC  TAC  AGT  GAC  GGT

192▶  Tyr  His  Val  Gln  Asp  Ala  Phe  Tyr  Ser  Asp  Gly

1926  TAT  GAA  GCA  CAG  TTT  GGA  GTG  CAG  CCA  ACT  TTC

203▶  Tyr  Glu  Ala  Gln  Phe  Gly  Val  Gln  Pro  Thr  Phe

1959  GTT  TTT  CTG  GTT  GCC  AGC  ACA  ACT  ATT  GAA  TGC

214▶  Val  Phe  Leu  Val  Ala  Ser  Thr  Thr  Ile  Glu  Cys

1992  GGA  CGT  TAT  CCG  GTT  GAA  ATT  TTC  ATG  ATG  GGC
```

Fig.7g

```
225▶ Gly Arg Tyr Pro Val Glu Ile Phe Met Met Gly
2025  GAA GAA GCA AAA CTG GCA GGT CAA CAG GAA TAT

236▶ Glu Glu Ala Lys Leu Ala Gly Gln Gln Glu Tyr
2058  CAC CGC AAT CTG CGA ACC CTG TCT GAC TGC CTG

247▶ His Arg Asn Leu Arg Thr Leu Ser Asp Cys Leu
                      BalI
2091  AAT ACC GAT GAA TGG CCA GCT ATT AAG ACA TTA

258▶ Asn Thr Asp Glu Trp Pro Ala Ile Lys Thr Leu
2124  TCA CTG CCC CGC TGG GCT AAG GAA TAT GCAA

269▶ Ser Leu Pro Arg Trp Ala Lys Glu Tyr AlaA
2155  ATG ACT AAG CAA CCA CCA ATC GCA AAA GCC GAT
   1▶ Met Thr Lys Gln Pro Pro Ile Ala Lys Ala Asp
279▶ s nAs p• • •
2188  CTG CAA AAA ACT CAG GGA AAC CGT GCA CCA GCA
  12▶ Leu Gln Lys Thr Gln Gly Asn Arg Ala Pro Ala
2221  GCA GTT AAA AAT AGC GAC GTG ATT AGT TTT ATT
  23▶ Ala Val Lys Asn Ser Asp Val Ile Ser Phe Ile
2254  AAC CAG CCA TCA ATG AAA GAG CAA CTG GCA GCA
  34▶ Asn Gln Pro Ser Met Lys Glu Gln Leu Ala Ala
                          NdeI
2287  GCT CTT CCA CGC CAT ATG ACG GCT GAA CGT ATG
  45▶ Ala Leu Pro Arg His Met Thr Ala Glu Arg Met
```

Fig.7h

```
2320 ATC CGT ATC GCC ACC ACA GAA ATT CGT AAA GTT
  56▶Ile Arg Ile Ala Thr Thr Glu Ile Arg Lys Val
2353 CCG GCG TTA GGA AAC TGT GAC ACT ATG AGT TTT
  67▶Pro Ala Leu Gly Asn Cys Asp Thr Met Ser Phe
2386 GTC AGT GCG ATC GTA CAG TGT TCA CAG CTC GGA
  78▶Val Ser Ala Ile Val Gln Cys Ser Gln Leu Gly
2419 CTT GAG CCA GGT AGC GCC CTC GGT CAT GCA TAT
  89▶Leu Glu Pro Gly Ser Ala Leu Gly His Ala Tyr
2452 TTA CTG CCT TTT GGT AAT AAA AAC GAA AAG AGC
 100▶Leu Leu Pro Phe Gly Asn Lys Asn Glu Lys Ser
2485 GGT AAA AAG AAC GTT CAG CTA ATC ATT GGC TAT
 111▶Gly Lys Lys Asn Val Gln Leu Ile Ile Gly Tyr
2518 CGC GGC ATG ATT GAT CTG GCT CGC CGT TCT GGT
 122▶Arg Gly Met Ile Asp Leu Ala Arg Arg Ser Gly
2551 CAA ATC GCC AGC CTG TCA GCC CGT GTT GTC CGT
 133▶Gln Ile Ala Ser Leu Ser Ala Arg Val Val Arg
2584 GAA GGT GAC GAG TTT AGC TTC GAA TTT GGC CTT
 144▶Glu Gly Asp Glu Phe Ser Phe Glu Phe Gly Leu
2617 GAT GAA AAG TTA ATA CAC CGC CCG GGA GAA AAC
 155▶Asp Glu Lys Leu Ile His Arg Pro Gly Glu Asn
2650 GAA GAT GCC CCG GTT ACC CAC GTC TAT GCT GTC
 166▶Glu Asp Ala Pro Val Thr His Val Tyr Ala Val
2683 GCA AGA CTG AAA GAC GGA GGT ACT CAG TTT GAA
 177▶Ala Arg Leu Lys Asp Gly Gly Thr Gln Phe Glu
2716 GTT ATG ACG CGC AAA CAG ATT GAG CTG GTG CGC
 188▶Val Met Thr Arg Lys Gln Ile Glu Leu Val Arg
```

Fig.7i

```
2749 AGC CTG AGT AAA GCT GGT AAT AAC GGG CCG TGG
 199▶Ser Leu Ser Lys Ala Gly Asn Asn Gly Pro Trp
2782 GTA ACT CAC TGG GAA GAA ATG GCA AAG AAA ACG
 210▶Val Thr His Trp Glu Glu Met Ala Lys Lys Thr
2815 GCT ATT CGT CGC CTG TTC AAA TAT TTG CCC GTA
 221▶Ala Ile Arg Arg Leu Phe Lys Tyr Leu Pro Val
2848 TCA ATT GAG ATC CAG CGT GCA GTA TCA ATG GAT
 232▶Ser Ile Glu Ile Gln Arg Ala Val Ser Met Asp
                                          PstI
2881 GAA AAG GAA CCA CTG ACA ATC GAT CCT GCA GAT
 243▶Glu Lys Glu Pro Leu Thr Ile Asp Pro Ala Asp
2914 TCC TCT GTA TTA ACC GGG GAA TAC AGT GTA ATC
 254▶Ser Ser Val Leu Thr Gly Glu Tyr Ser Val Ile
                            BglII     HindIII
2947 GAT AAT TCA GAG GAA TAG ATCTAAGCTT
 265▶Asp Asn Ser Glu Glu •••
2975 GGCTGTTTTG GCGGATGAGA GAAGATTTTC AGCCTGATAC
3015 AGATTAAATC AGAACGCAGA AGCGGTCTGA TAAAACAGAA
3055 TTTGCCTGGC GGCAGTAGCG CGGTGGTCCC ACCTGACCCC
3095 ATGCCGAACT CAGAAGTGAA ACGCCGTAGC GCCGATGGTA
3135 GTGTGGGGTC TCCCCATGCG AGAGTAGGGA ACTGCCAGGC
3175 ATCAAATAAA ACGAAAGGCT CAGTCGAAAG ACTGGGCCTT
3215 TCGTTTTATC TGTTGTTTGT CGGTGAACGC TCTCCTGAGT
3255 AGGACAAATC CGCCGGGAGC GGATTTGAAC GTTGCGAAGC
3295 AACGGCCCGG AGGGTGGCGG GCAGGACGCC CGCCATAAAC
3335 TGCCAGGCAT CAAATTAAGC AGAAGGCCAT CCTGACGGAT
```

Fig.7j

```
3375 GGCCTTTTTG CGTTTCTACA AACTCTTTTG TTTATTTTTC
3415 TAAATACATT CAAATATGTA TCCGCTCATG AGACAATAAC
3455 CCTGATAAAT GCTTCAATAA TATTGAAAAA GGAAGAGT AT
                                             1▶Me
3495 G   AGT ATT CAA CAT TTC CGT GTC GCC CTT ATT
  1▶t Ser Ile Gln His Phe Arg Val Ala Leu Ile
3526 CCC TTT TTT GCG GCA TTT TGC CTT CCT GTT TTT
 12▶ Pro Phe Phe Ala Ala Phe Cys Leu Pro Val Phe
3559 GCT CAC CCA GAA ACG CTG GTG AAA GTA AAA GAT
 23▶ Ala His Pro Glu Thr Leu Val Lys Val Lys Asp
3592 GCT GAA GAT CAG TTG GGT GCA CGA GTG GGT TAC
 34▶ Ala Glu Asp Gln Leu Gly Ala Arg Val Gly Tyr
3625 ATC GAA CTG GAT CTC AAC AGC GGT AAG ATC CTT
 45▶ Ile Glu Leu Asp Leu Asn Ser Gly Lys Ile Leu
3658 GAG AGT TTT CGC CCC GAA GAA CGT TTT CCA ATG
 56▶ Glu Ser Phe Arg Pro Glu Glu Arg Phe Pro Met
3691 ATG AGC ACT TTT AAA GTT CTG CTA TGT GGC GCG
 67▶ Met Ser Thr Phe Lys Val Leu Leu Cys Gly Ala
3724 GTA TTA TCC CGT GTT GAC GCC GGG CAA GAG CAA
 78▶ Val Leu Ser Arg Val Asp Ala Gly Gln Glu Gln
3757 CTC GGT CGC CGC ATA CAC TAT TCT CAG AAT GAC
 89▶ Leu Gly Arg Arg Ile His Tyr Ser Gln Asn Asp
                   Scal
3790 TTG GTT GAG TAC TCA CCA GTC ACA GAA AAG CAT
100▶ Leu Val Glu Tyr Ser Pro Val Thr Glu Lys His
3823 CTT ACG GAT GGC ATG ACA GTA AGA GAA TTA TGC
111▶ Leu Thr Asp Gly Met Thr Val Arg Glu Leu Cys
```

Fig.7k

```
3856  AGT  GCT  GCC  ATA  ACC  ATG  AGT  GAT  AAC  ACT  GCG
 122▶ Ser  Ala  Ala  Ile  Thr  Met  Ser  Asp  Asn  Thr  Ala

3889  GCC  AAC  TTA  CTT  CTG  ACA  ACG  ATC  GGA  GGA  CCG
 133▶ Ala  Asn  Leu  Leu  Leu  Thr  Thr  Ile  Gly  Gly  Pro

3922  AAG  GAG  CTA  ACC  GCT  TTT  TTG  CAC  AAC  ATG  GGG
 144▶ Lys  Glu  Leu  Thr  Ala  Phe  Leu  His  Asn  Met  Gly

3955  GAT  CAT  GTA  ACT  CGC  CTT  GAT  CGT  TGG  GAA  CCG
 155▶ Asp  His  Val  Thr  Arg  Leu  Asp  Arg  Trp  Glu  Pro

3988  GAG  CTG  AAT  GAA  GCC  ATA  CCA  AAC  GAC  GAG  CGT
 166▶ Glu  Leu  Asn  Glu  Ala  Ile  Pro  Asn  Asp  Glu  Arg

4021  GAC  ACC  ACG  ATG  CCT  GTA  GCA  ATG  GCA  ACA  ACG
 177▶ Asp  Thr  Thr  Met  Pro  Val  Ala  Met  Ala  Thr  Thr

4054  TTG  CGC  AAA  CTA  TTA  ACT  GGC  GAA  CTA  CTT  ACT
 188▶ Leu  Arg  Lys  Leu  Leu  Thr  Gly  Glu  Leu  Leu  Thr

4087  CTA  GCT  TCC  CGG  CAA  CAA  TTA  ATA  GAC  TGG  ATG
 199▶ Leu  Ala  Ser  Arg  Gln  Gln  Leu  Ile  Asp  Trp  Met

4120  GAG  GCG  GAT  AAA  GTT  GCA  GGA  CCA  CTT  CTG  CGC
 210▶ Glu  Ala  Asp  Lys  Val  Ala  Gly  Pro  Leu  Leu  Arg

4153  TCG  GCC  CTT  CCG  GCT  GGC  TGG  TTT  ATT  GCT  GAT
 221▶ Ser  Ala  Leu  Pro  Ala  Gly  Trp  Phe  Ile  Ala  Asp

4186  AAA  TCT  GGA  GCC  GGT  GAG  CGT  GGG  TCT  CGC  GGT
 232▶ Lys  Ser  Gly  Ala  Gly  Glu  Arg  Gly  Ser  Arg  Gly

4219  ATC  ATT  GCA  GCA  CTG  GGG  CCA  GAT  GGT  AAG  CCC
 243▶ Ile  Ile  Ala  Ala  Leu  Gly  Pro  Asp  Gly  Lys  Pro

4252  TCC  CGT  ATC  GTA  GTT  ATC  TAC  ACG  ACG  GGG  AGT
 254▶ Ser  Arg  Ile  Val  Val  Ile  Tyr  Thr  Thr  Gly  Ser
```

Fig.71

```
4285 CAG GCA ACT ATG GAT GAA CGA AAT AGA CAG ATC
 265▶Gln Ala Thr Met Asp Glu Arg Asn Arg Gln Ile
4318 GCT GAG ATA GGT GCC TCA CTG ATT AAG CAT TGG
 276▶Ala Glu Ile Gly Ala Ser Leu Ile Lys His Trp
4351 TAA CTGTCAGACC AAGTTTACTC ATATATACTT
 287▶···
4384 TAGATTGATT TACGCGCCCT GTAGCGGCGC ATTAAGCGCG
4424 GCGGGTGTGG TGGTTACGCG CAGCGTGACC GCTACACTTG
4464 CCAGCGCCCT AGCGCCGCT CCTTTCGCTT TCTTCCCTTC
4504 CTTTCTCGCC ACGTTCGCCG GCTTTCCCCG TCAAGCTCTA
4544 AATCGGGGGC TCCCTTTAGG GTTCCGATTT AGTGCTTTAC
4584 GGCACCTCGA CCCCAAAAAA CTTGATTTGG GTGATGGTTC
4624 ACGTAGTGGG CCATCGCCCT GATAGACGGT TTTTCGCCCT
4664 TTGACGTTGG AGTCCACGTT CTTTAATAGT GGACTCTTGT
4704 TCCAAACTTG AACAACACTC AACCCTATCT CGGGCTATTC
4744 TTTTGATTTA TAAGGGATTT TGCCGATTTC GGCCTATTGG
4784 TTAAAAATG AGCTGATTTA ACAAAATTT AACGCGAATT
4824 TTAACAAAAT ATTAACGTTT ACAATTTAAA AGGATCTAGG
4864 TGAAGATCCT TTTTGATAAT CTCATGACCA AAATCCCTTA
4904 ACGTGAGTTT TCGTTCCACT GAGCGTCAGA CCCCGTAGAA
4944 AAGATCAAAG GATCTTCTTG AGATCCTTTT TTTCTGCGCG
4984 TAATCTGCTG CTTGCAAACA AAAAAACCAC CGCTACCAGC
5024 GGTGGTTTGT TTGCCGGATC AAGAGCTACC AACTCTTTTT
```

Fig.7m

```
5064  CCGAAGGTAA CTGGCTTCAG CAGAGCGCAG ATACCAAATA
5104  CTGTCCTTCT AGTGTAGCCG TAGTTAGGCC ACCACTTCAA
5144  GAACTCTGTA GCACCGCCTA CATACCTCGC TCTGCTAATC
5184  CTGTTACCAG TGGCTGCTGC CAGTGGCGAT AAGTCGTGTC
5224  TTACCGGGTT GGACTCAAGA CGATAGTTAC CGGATAAGGC
5264  GCAGCGGTCG GGCTGAACGG GGGGTTCGTG CACACAGCCC
5304  AGCTTGGAGC GAACGACCTA CACCGAACTG AGATACCTAC
5344  AGCGTGAGCT ATGAGAAAGC GCCACGCTTC CCGAAGGGAG
5384  AAAGGCGGAC AGGTATCCGG TAAGCGGCAG GGTCGGAACA
5424  GGAGAGCGCA CGAGGGAGCT TCCAGGGGGA AACGCCTGGT
5464  ATCTTTATAG TCCTGTCGGG TTTCGCCACC TCTGACTTGA
5504  GCGTCGATTT TTGTGATGCT CGTCAGGGGG GCGGAGCCTA
5544  TGGAAAAACG CCAGCAACGC GGCCTTTTTA CGGTTCCTGG
5584  CCTTTTGCTG GCCTTTTGCT CACATGTTCT TTCCTGCGTT
5624  ATCCCCTGAT TCTGTGGATA ACCGTATTAC CGCCTTTGAG
5664  TGAGCTGATA CCGCTCGCCG CAGCCGAACG ACCGAGCGCA
5704  GCGAGTCAGT GAGCGAGGAA GCGGAAGAGC GCCTGATGCG
5744  GTATTTTCTC CTTACGCATC TGTGCGGTAT TCACACCGC
5784  ATAGGGTCAT GGCTGCGCCC CGACACCCGC CAACACCCGC
5824  TGACGCGCCC TGACGGGCTT GTCTGCTCCC GGCATCCGCT
5864  TACAGACAAG CTGTGACCGT CTCCGGGAGC TGCATGTGTC
5904  AGAGGTTTTC ACCGTCATCA CCGAAACGCG CGAGGCAGCA
5944  AGGAGATGGC GCCCAACAGT CCCCCGGCCA CGGGGCCTGC
```

Fig.7n

```
5984   CACCATACCC  ACGCCGAAAC  AAGCGCTCAT  GAGCCCGAAG
6024   TGGCGAGCCC  GATCTTCCCC  ATCGGTGATG  TCGGCGATAT
6064   AGGCGCCAGC  AACCGCACCT  GTGGCGCCGG  TGATGCCGGC
6104   CACGATGCGT  CCGGCGTAGA  GGATCTGCTC  ATGTTTGACA
6144   GCTTATC
```

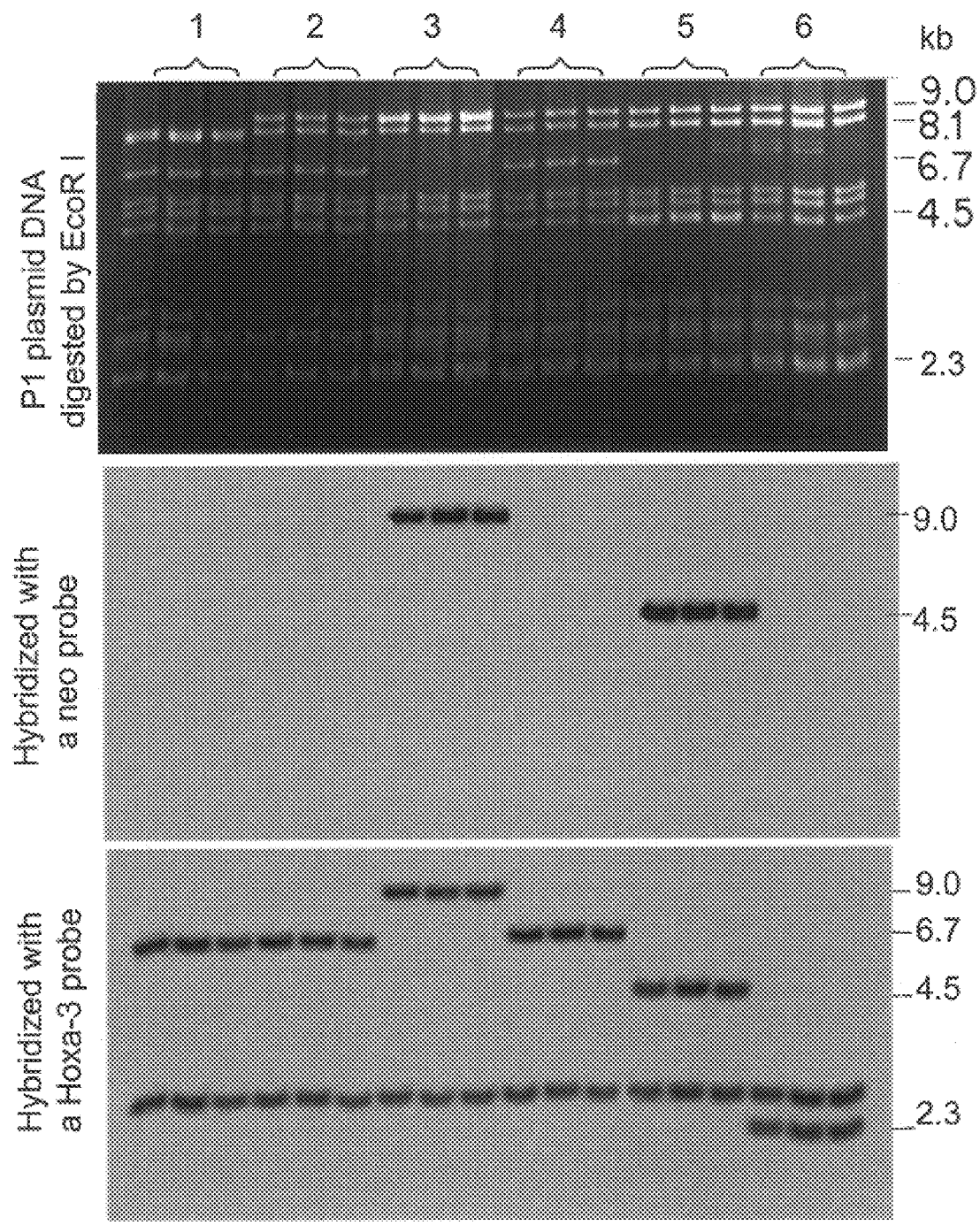

NS3145 (recA⁻, recBC⁺), P1 packaging strain

+

Fig.13b

```
  1 ATCGATGCATAATGTGCCTGTCAAATGGACGAAGCAGGG

40 ATTCTGCAAACCCTATGCTACTCCGTCAAGCCGTCAATT

79 GTCTGATTCGTTACCAA TTA TGA CAA CTT GAC
                     293◄• • • Ser Leu Lys Val

111 GGC TAC ATC ATT CAC TTT TTC TTC ACA ACC
288◄Ala Val Asp Asn Val Lys Glu Glu Cys Gly

141 GGC ACG GAA CTC GCT CGG GCT GGC CCC GGT
278◄Ala Arg Phe Glu Ser Pro Ser Ala Gly Thr

171 GCA TTT TTT AAA TAC CCG CGA GAA ATA GAG
268◄Cys Lys Lys Phe Val Arg Ser Phe Tyr Leu

201 TTG ATC GTC AAA ACC AAC ATT GCG ACC GAC
258◄Gln Asp Asp Phe Gly Val Asn Arg Gly Val

231 GGT GGC GAT AGG CAT CCG GGT GGT GCT CAA
248◄Thr Ala Ile Pro Met Arg Thr Thr Ser Leu

261 AAG CAG CTT CGC CTG GCT GAT ACG TTG GTC
238◄Leu Leu Lys Ala Gln Ser Ile Arg Gln Asp

291 CTC GCG CCA GCT TAA GAC GCT AAT CCC TAA
228◄Glu Arg Trp Ser Leu Val Ser Ile Gly Leu

321 CTG CTG GCG GAA AAG ATG TGA CAG ACG CGA
218◄Gln Gln Arg Phe Leu His Ser Leu Arg Ser

351 CGG CGA CAA GCA AAC ATG CTG TGC GAC GCT
208◄Pro Ser Leu Cys Val His Gln Ala Val Ser

381 GGC GAT ATC AAA ATT GCT GTC TGC CAG GTG
198◄Ala Ile Asp Phe Asn Ser Asp Ala Leu His

411 ATC GCT GAT GTA CTG ACA AGC CTC GCG TAC
```

Fig.13c

```
188◄Asp Ser Ile Tyr Gln Cys Ala Glu Arg Val
441  CCG ATT ATC CAT CGG TGG ATG GAG CGA CTC
178◄Arg Asn Asp Met Pro Pro His Leu Ser Glu
471  GTT AAT CGC TTC CAT GCG CCG CAG TAA CAA
168◄Asn Ile Ala Glu Met Arg Arg Leu Leu Leu
501  TTG CTC AAG CAG ATT TAT CGC CAG CAG CTC
158◄Gln Glu Leu Leu Asn Ile Ala Leu Leu Glu
531  CGA ATA GCG CCC TTC CCC TTG CCC GGC GTT
148◄Ser Tyr Arg Gly Glu Gly Gln Gly Ala Asn
561  AAT GAT TTG CCC AAA CAG GTC GCT GAA ATG
138◄Ile Ile Gln Gly Phe Leu Asp Ser Phe His
591  CGG CTG GTG CGC TTC ATC CGG GCG AAA GAA
128◄Pro Gln His Ala Glu Asp Pro Arg Phe Phe
621  CCC CGT ATT GGC AAA TAT TGA CGG CCA GTT
118◄Gly Thr Asn Ala Phe Ile Ser Pro Trp Asn
651  AAG CCA TTC ATG CCA GTA GGC GCG CGG ACG
108◄Leu Trp Glu His Trp Tyr Ala Arg Pro Arg
681  AAA GTA AAC CCA CTG GTG ATA CCA TTC GCG
 98◄Phe Tyr Val Trp Gln His Tyr Trp Glu Arg
711  AGC CTC CGG ATG ACG ACC GTA GTG ATG AAT
 88◄Ala Glu Pro His Arg Gly Tyr His His Ile
741  CTC TCC TGG CGG GAA CAG CAA AAT ATC ACC
 78◄Glu Gly Pro Pro Phe Leu Leu Ile Asp Gly
771  CGG TCG GCA AAC AAA TTC TCG TCC CTG ATT
 68◄Pro Arg Cys Val Phe Glu Arg Gly Gln Asn
```

Fig.13e

```
                                    NheI         EcoRI      NcoI  BamHI
1255 TTTTTATCGCAACTCTCTACTGTTTCTCCATACCCGTTT
1294 TTTTGGGCTAGCAGGAGGAAT TCACC ATG GAT CCC
                                        1▶Met Asp Pro
1329 GTA ATC GTA GAA GAC ATA GAG CCA GGT ATT
   4▶Val Ile Val Glu Asp Ile Glu Pro Gly Ile
1359 TAT TAC GGA ATT TCG AAT GAG AAT TAC CAC
  14▶Tyr Tyr Gly Ile Ser Asn Glu Asn Tyr His
1389 GCG GGT CCC GGT ATC AGT AAG TCT CAG CTC
  24▶Ala Gly Pro Gly Ile Ser Lys Ser Gln Leu
1419 GAT GAC ATT GCT GAT ACT CCG GCA CTA TAT
  34▶Asp Asp Ile Ala Asp Thr Pro Ala Leu Tyr
1449 TTG TGG CGT AAA AAT GCC CCC GTG GAC ACC
  44▶Leu Trp Arg Lys Asn Ala Pro Val Asp Thr
1479 ACA AAG ACA AAA ACG CTC GAT TTA GGA ACT
  54▶Thr Lys Thr Lys Thr Leu Asp Leu Gly Thr
1509 GCT TTC CAC TGC CGG GTA CTT GAA CCG GAA
  64▶Ala Phe His Cys Arg Val Leu Glu Pro Glu
       EcoRI
1539 GAA TTC AGT AAC CGC TTT ATC GTA GCA CCT
  74▶Glu Phe Ser Asn Arg Phe Ile Val Ala Pro
1569 GAA TTT AAC CGC CGT ACA AAC GCC GGA AAA
  84▶Glu Phe Asn Arg Arg Thr Asn Ala Gly Lys
1599 GAA GAA GAG AAA GCG TTT CTG ATG GAA TGC
  94▶Glu Glu Glu Lys Ala Phe Leu Met Glu Cys
1629 GCA AGC ACA GGA AAA ACG GTT ATC ACT GCG
 104▶Ala Ser Thr Gly Lys Thr Val Ile Thr Ala
```

Fig.13f

```
1659 GAA GAA GGC CGG AAA ATT GAA CTC ATG TAT
114▶ Glu Glu Gly Arg Lys Ile Glu Leu Met Tyr

1689 CAA AGC GTT ATG GCT TTG CCG CTG GGG CAA
124▶ Gln Ser Val Met Ala Leu Pro Leu Gly Gln

1719 TGG CTT GTT GAA AGC GCC GGA CAC GCT GAA
134▶ Trp Leu Val Glu Ser Ala Gly His Ala Glu

1749 TCA TCA ATT TAC TGG GAA GAT CCT GAA ACA
144▶ Ser Ser Ile Tyr Trp Glu Asp Pro Glu Thr

1779 GGA ATT TTG TGT CGG TGC CGT CCG GAC AAA
154▶ Gly Ile Leu Cys Arg Cys Arg Pro Asp Lys

1809 ATT ATC CCT GAA TTT CAC TGG ATC ATG GAC
164▶ Ile Ile Pro Glu Phe His Trp Ile Met Asp

1839 GTG AAA ACT ACG GCG GAT ATT CAA CGA TTC
174▶ Val Lys Thr Thr Ala Asp Ile Gln Arg Phe

1869 AAA ACC GCT TAT TAC GAC TAC CGC TAT CAC
184▶ Lys Thr Ala Tyr Tyr Asp Tyr Arg Tyr His

1899 GTT CAG GAT GCA TTC TAC AGT GAC GGT TAT
194▶ Val Gln Asp Ala Phe Tyr Ser Asp Gly Tyr

1929 GAA GCA CAG TTT GGA GTG CAG CCA ACT TTC
204▶ Glu Ala Gln Phe Gly Val Gln Pro Thr Phe

1959 GTT TTT CTG GTT GCC AGC ACA ACT ATT GAA
214▶ Val Phe Leu Val Ala Ser Thr Thr Ile Glu

1989 TGC GGA CGT TAT CCG GTT GAA ATT TTC ATG
224▶ Cys Gly Arg Tyr Pro Val Glu Ile Phe Met

2019 ATG GGC GAA GAA GCA AAA CTG GCA GGT CAA
234▶ Met Gly Glu Glu Ala Lys Leu Ala Gly Gln
```

Fig.13g

```
2049 CAG GAA TAT CAC CGC AAT CTG CGA ACC CTG
 244▶Gln Glu Tyr His Arg Asn Leu Arg Thr Leu

2079 TCT GAC TGC CTG AAT ACC GAT GAA TGG CCA
 254▶Ser Asp Cys Leu Asn Thr Asp Glu Trp Pro

2109 GCT ATT AAG ACA TTA TCA CTG CCC CGC TGG
 264▶Ala Ile Lys Thr Leu Ser Leu Pro Arg Trp
                                     XhoI  KpnI
2139 GCT AAG GAA TAT GCA AAT GAC TAGATCTCGAG
 274▶Ala Lys Glu Tyr Ala Asn Asp

2171 GTACCCGAGCACGTGTTGACAATTAATCATCGGCATAGT

2210 ATATCGGCATAGTATAATACGACAAGGTGAGGAACTAAA
       NcoI
2249 CC ATG GCT AAG CAA CCA CCA ATC GCA AAA
      1▶Met Ala Lys Gln Pro Pro Ile Ala Lys

2278 GCC GAT CTG CAA AAA ACT CAG GGA AAC CGT
  10▶Ala Asp Leu Gln Lys Thr Gln Gly Asn Arg

2308 GCA CCA GCA GCA GTT AAA AAT AGC GAC GTG
  20▶Ala Pro Ala Ala Val Lys Asn Ser Asp Val

2338 ATT AGT TTT ATT AAC CAG CCA TCA ATG AAA
  30▶Ile Ser Phe Ile Asn Gln Pro Ser Met Lys

2368 GAG CAA CTG GCA GCA GCT CTT CCA CGC CAT
  40▶Glu Gln Leu Ala Ala Ala Leu Pro Arg His

2398 ATG ACG GCT GAA CGT ATG ATC CGT ATC GCC
  50▶Met Thr Ala Glu Arg Met Ile Arg Ile Ala

2428 ACC ACA GAA ATT CGT AAA GTT CCG GCG TTA
  60▶Thr Thr Glu Ile Arg Lys Val Pro Ala Leu
```

Fig.13h

```
2458  GGA AAC TGT GAC ACT ATG AGT TTT GTC AGT
  70▶ Gly Asn Cys Asp Thr Met Ser Phe Val Ser
2488  GCG ATC GTA CAG TGT TCA CAG CTC GGA CTT
  80▶ Ala Ile Val Gln Cys Ser Gln Leu Gly Leu
2518  GAG CCA GGT AGC GCC CTC GGT CAT GCA TAT
  90▶ Glu Pro Gly Ser Ala Leu Gly His Ala Tyr
2548  TTA CTG CCT TTT GGT AAT AAA AAC GAA AAG
 100▶ Leu Leu Pro Phe Gly Asn Lys Asn Glu Lys
2578  AGC GGT AAA AAG AAC GTT CAG CTA ATC ATT
 110▶ Ser Gly Lys Lys Asn Val Gln Leu Ile Ile
2608  GGC TAT CGC GGC ATG ATT GAT CTG GCT CGC
 120▶ Gly Tyr Arg Gly Met Ile Asp Leu Ala Arg
2638  CGT TCT GGT CAA ATC GCC AGC CTG TCA GCC
 130▶ Arg Ser Gly Gln Ile Ala Ser Leu Ser Ala
2668  CGT GTT GTC CGT GAA GGT GAC GAG TTT AGC
 140▶ Arg Val Val Arg Glu Gly Asp Glu Phe Ser
2698  TTC GAA TTT GGC CTT GAT GAA AAG TTA ATA
 150▶ Phe Glu Phe Gly Leu Asp Glu Lys Leu Ile
2728  CAC CGC CCG GGA GAA AAC GAA GAT GCC CCG
 160▶ His Arg Pro Gly Glu Asn Glu Asp Ala Pro
2758  GTT ACC CAC GTC TAT GCT GTC GCA AGA CTG
 170▶ Val Thr His Val Tyr Ala Val Ala Arg Leu
2788  AAA GAC GGA GGT ACT CAG TTT GAA GTT ATG
 180▶ Lys Asp Gly Gly Thr Gln Phe Glu Val Met
2818  ACG CGC AAA CAG ATT GAG CTG GTG CGC AGC
 190▶ Thr Arg Lys Gln Ile Glu Leu Val Arg Ser
```

Fig.13i

```
2848 CTG AGT AAA GCT GGT AAT AAC GGG CCG TGG
 200▶Leu Ser Lys Ala Gly Asn Asn Gly Pro Trp

2878 GTA ACT CAC TGG GAA GAA ATG GCA AAG AAA
 210▶Val Thr His Trp Glu Glu Met Ala Lys Lys

2908 ACG GCT ATT CGT CGC CTG TTC AAA TAT TTG
 220▶Thr Ala Ile Arg Arg Leu Phe Lys Tyr Leu

2938 CCC GTA TCA ATT GAG ATC CAG CGT GCA GTA
 230▶Pro Val Ser Ile Glu Ile Gln Arg Ala Val

2968 TCA ATG GAT GAA AAG GAA CCA CTG ACA ATC
 240▶Ser Met Asp Glu Lys Glu Pro Leu Thr Ile

2998 GAT CCT GCA GAT TCC TCT GTA TTA ACC GGG
 250▶Asp Pro Ala Asp Ser Ser Val Leu Thr Gly

3028 GAA TAC AGT GTA ATC GAT AAT TCA GAG GAA
 260▶Glu Tyr Ser Val Ile Asp Asn Ser Glu Glu
          BglII    HindIII
3058 TAG ATCTAAGCTTCCTGCTGAACATCAAAGGCAAGAAA
 270▶• • •

3096 ACATCTGTTGTCAAAGACAGCATCCTTGAACAAGGACAA

3135 TTAACAGTTAACAAATAAAAACGCAAAGAAAATGCCGA

3174 TATCCTATTGGCATTTTCTTTTATTTCTTATCAACATAA
                         XhoI
3213 AGGTGAATCCCATACCTCGAGCTTCACGCTGCCGCAAGC

3252 ACTCAGGGCGCAAGGGCTGCTAAAAGGAAGCGGAACACG

3291 TAGAAAGCCAGTCCGCAGAAACGGTGCTGACCCCGGATG

3330 AATGTCAGCTACTGGGCTATCTGGACAAGGGAAAACGCA

3369 AGCGCAAAGAGAAAGCAGGTAGCTTGCAGTGGGCTTACA
```

Fig.13j

```
3408  TGGCGATAGCTAGACTGGGCGGTTTTATGGACAGCAAGC
3447  GAACCGGAATTGCCAGCTGGGGCGCCCTCTGGTAAGGTT
3486  GGGAAGCCCTGCAAAGTAAACTGGATGGCTTTCTTGCCG
                                         BglII
3525  CCAAGGATCTGATGGCGCAGGGGATCAAGATCTGATCAA
3564  GAGACAGGATGAGGATCGTTTCGC ATG GAT ATT
                                    1▸Met Asp Ile
```

| 3597 | AAT | ACT | GAA | ACT | GAG | ATC | AAG | CAA | AAG | CAT |
|---|---|---|---|---|---|---|---|---|---|---|
| 4▸ | Asn | Thr | Glu | Thr | Glu | Ile | Lys | Gln | Lys | His |
| 3627 | TCA | CTA | ACC | CCC | TTT | CCT | GTT | TTC | CTA | ATC |
| 14▸ | Ser | Leu | Thr | Pro | Phe | Pro | Val | Phe | Leu | Ile |
| 3657 | AGC | CCG | GCA | TTT | CGC | GGG | CGA | TAT | TTT | CAC |
| 24▸ | Ser | Pro | Ala | Phe | Arg | Gly | Arg | Tyr | Phe | His |
| 3687 | AGC | TAT | TTC | AGG | AGT | TCA | GCC | ATG | AAC | GCT |
| 34▸ | Ser | Tyr | Phe | Arg | Ser | Ser | Ala | Met | Asn | Ala |
| 3717 | TAT | TAC | ATT | CAG | GAT | CGT | CTT | GAG | GCT | CAG |
| 44▸ | Tyr | Tyr | Ile | Gln | Asp | Arg | Leu | Glu | Ala | Gln |
| 3747 | AGC | TGG | GCG | CGT | CAC | TAC | CAG | CAG | CTC | GCC |
| 54▸ | Ser | Trp | Ala | Arg | His | Tyr | Gln | Gln | Leu | Ala |
| 3777 | CGT | GAA | GAG | AAA | GAG | GCA | GAA | CTG | GCA | GAC |
| 64▸ | Arg | Glu | Glu | Lys | Glu | Ala | Glu | Leu | Ala | Asp |
| 3807 | GAC | ATG | GAA | AAA | GGC | CTG | CCC | CAG | CAC | CTG |
| 74▸ | Asp | Met | Glu | Lys | Gly | Leu | Pro | Gln | His | Leu |
| 3837 | TTT | GAA | TCG | CTA | TGC | ATC | GAT | CAT | TTG | CAA |
| 84▸ | Phe | Glu | Ser | Leu | Cys | Ile | Asp | His | Leu | Gln |
| 3867 | CGC | CAC | GGG | GCC | AGC | AAA | AAA | TCC | ATT | ACC |
| 94▸ | Arg | His | Gly | Ala | Ser | Lys | Lys | Ser | Ile | Thr |

Fig.13k

```
3897 CGT GCG TTT GAT GAC GAT GTT GAG TTT CAG
 104▶Arg Ala Phe Asp Asp Asp Val Glu Phe Gln
3927 GAG CGC ATG GCA GAA CAC ATC CGG TAC ATG
 114▶Glu Arg Met Ala Glu His Ile Arg Tyr Met
3957 GTT GAA ACC ATT GCT CAC CAC CAG GTT GAT
 124▶Val Glu Thr Ile Ala His His Gln Val Asp
                                        HindIII
3987 ATT GAT TCA GAG GTA TAA AACGAGTAGA AGCT
 134▶Ile Asp Ser Glu Val •••
4019 TGGCTGTTTTGGCGGATGAGAGAAGATTTTCAGCCTGAT
4058 ACAGATTAAATCAGAACGCAGAAGCGGTCTGATAAAACA
4097 GAATTTGCCTGGCGGCAGTAGCGCGGTGGTCCCACCTGA
4136 CCCCATGCCGAACTCAGAAGTGAAACGCCGTAGCGCCGA
4175 TGGTAGTGTGGGGTCTCCCCATGCGAGAGTAGGGAACTG
4214 CCAGGCATCAAATAAAACGAAAGGCTCAGTCGAAAGACT
4253 GGGCCTTTCGTTTTATCTGTTGTTTGTCGGTGAACGCTC
4292 TCCTGAGTAGGACAAATCCGCCGGGAGCGGATTTGAACG
4331 TTGCGAAGCAACGGCCCGGAGGGTGGCGGGCAGGACGCC
4370 CGCCATAAACTGCCAGGCATCAAATTAAGCAGAAGGCCA
4409 TCCTGACGGATGGCCTTTTTGCGTTTCTACAAACTCTTT
4448 TGTTTATTTTTCTAAATACATTCAAATATGTATCCGCTC
4487 ATGAGACAATAACCCTGATAAATGCTTCAATAATATTGA
4526 AAAAGGAAGAGT ATG AGT ATT CAA CAT TTC
               1▶Met Ser Ile Gln His Phe
```

Fig.13I

```
4556  CGT GTC GCC CTT ATT CCC TTT TTT GCG GCA
   7▶ Arg Val Ala Leu Ile Pro Phe Phe Ala Ala
4586  TTT TGC CTT CCT GTT TTT GCT CAC CCA GAA
  17▶ Phe Cys Leu Pro Val Phe Ala His Pro Glu
4616  ACG CTG GTG AAA GTA AAA GAT GCT GAA GAT
  27▶ Thr Leu Val Lys Val Lys Asp Ala Glu Asp
4646  CAG TTG GGT GCA CGA GTG GGT TAC ATC GAA
  37▶ Gln Leu Gly Ala Arg Val Gly Tyr Ile Glu
4676  CTG GAT CTC AAC AGC GGT AAG ATC CTT GAG
  47▶ Leu Asp Leu Asn Ser Gly Lys Ile Leu Glu
4706  AGT TTT CGC CCC GAA GAA CGT TTT CCA ATG
  57▶ Ser Phe Arg Pro Glu Glu Arg Phe Pro Met
4736  ATG AGC ACT TTT AAA GTT CTG CTA TGT GGC
  67▶ Met Ser Thr Phe Lys Val Leu Leu Cys Gly
4766  GCG GTA TTA TCC CGT GTT GAC GCC GGG CAA
  77▶ Ala Val Leu Ser Arg Val Asp Ala Gly Gln
4796  GAG CAA CTC GGT CGC CGC ATA CAC TAT TCT
  87▶ Glu Gln Leu Gly Arg Arg Ile His Tyr Ser
                                        ScaI
4826  CAG AAT GAC TTG GTT GAG TAC TCA CCA GTC
  97▶ Gln Asn Asp Leu Val Glu Tyr Ser Pro Val
4856  ACA GAA AAG CAT CTT ACG GAT GGC ATG ACA
 107▶ Thr Glu Lys His Leu Thr Asp Gly Met Thr
4886  GTA AGA GAA TTA TGC AGT GCT GCC ATA ACC
 117▶ Val Arg Glu Leu Cys Ser Ala Ala Ile Thr
4916  ATG AGT GAT AAC ACT GCG GCC AAC TTA CTT
 127▶ Met Ser Asp Asn Thr Ala Ala Asn Leu Leu
```

Fig.13m

```
4946 CTG ACA ACG ATC GGA GGA CCG AAG GAG CTA
 137▶Leu Thr Thr Ile Gly Gly Pro Lys Glu Leu

4976 ACC GCT TTT TTG CAC AAC ATG GGG GAT CAT
 147▶Thr Ala Phe Leu His Asn Met Gly Asp His

5006 GTA ACT CGC CTT GAT CGT TGG GAA CCG GAG
 157▶Val Thr Arg Leu Asp Arg Trp Glu Pro Glu

5036 CTG AAT GAA GCC ATA CCA AAC GAC GAG CGT
 167▶Leu Asn Glu Ala Ile Pro Asn Asp Glu Arg

5066 GAC ACC ACG ATG CCT GTA GCA ATG GCA ACA
 177▶Asp Thr Thr Met Pro Val Ala Met Ala Thr

5096 ACG TTG CGC AAA CTA TTA ACT GGC GAA CTA
 187▶Thr Leu Arg Lys Leu Leu Thr Gly Glu Leu

5126 CTT ACT CTA GCT TCC CGG CAA CAA TTA ATA
 197▶Leu Thr Leu Ala Ser Arg Gln Gln Leu Ile

5156 GAC TGG ATG GAG GCG GAT AAA GTT GCA GGA
 207▶Asp Trp Met Glu Ala Asp Lys Val Ala Gly

5186 CCA CTT CTG CGC TCG GCC CTT CCG GCT GGC
 217▶Pro Leu Leu Arg Ser Ala Leu Pro Ala Gly

5216 TGG TTT ATT GCT GAT AAA TCT GGA GCC GGT
 227▶Trp Phe Ile Ala Asp Lys Ser Gly Ala Gly

5246 GAG CGT GGG TCT CGC GGT ATC ATT GCA GCA
 237▶Glu Arg Gly Ser Arg Gly Ile Ile Ala Ala

5276 CTG GGG CCA GAT GGT AAG CCC TCC CGT ATC
 247▶Leu Gly Pro Asp Gly Lys Pro Ser Arg Ile

5306 GTA GTT ATC TAC ACG ACG GGG AGT CAG GCA
 257▶Val Val Ile Tyr Thr Thr Gly Ser Gln Ala
```

Fig.13n

```
5336 ACT ATG GAT GAA CGA AAT AGA CAG ATC GCT
 267▶Thr Met Asp Glu Arg Asn Arg Gln Ile Ala

5366 GAG ATA GGT GCC TCA CTG ATT AAG CAT TGG
 277▶Glu Ile Gly Ala Ser Leu Ile Lys His Trp

5396 TAA CTGTCAGACCAAGTTTACTCATATATACTTTAGAT
 287▶···

5434 TGATTTACGCGCCCTGTAGCGGCGCATTAAGCGCGGCGG
5473 GTGTGGTGGTTACGCGCAGCGTGACCGCTACACTTGCCA
5512 GCGCCCTAGCGCCCGCTCCTTTCGCTTTCTTCCCTTCCT
5551 TTCTCGCCACGTTCGCCGGCTTTCCCCGTCAAGCTCTAA
5590 ATCGGGGGCTCCCTTTAGGGTTCCGATTTAGTGCTTTAC
5629 GGCACCTCGACCCCAAAAAACTTGATTTGGGTGATGGTT
5668 CACGTAGTGGGCCATCGCCCTGATAGACGGTTTTTCGCC
5707 CTTTGACGTTGGAGTCCACGTTCTTTAATAGTGGACTCT
5746 TGTTCCAAACTTGAACAACACTCAACCCTATCTCGGGCT
5785 ATTCTTTTGATTTATAAGGGATTTTGCCGATTTCGGCCT
5824 ATTGGTTAAAAAATGAGCTGATTTAACAAAAATTTAACG
5863 CGAATTTTAACAAAATATTAACGTTTACAATTTAAAAGG
5902 ATCTAGGTGAAGATCCTTTTTGATAATCTCATGACCAAA
5941 ATCCCTTAACGTGAGTTTTCGTTCCACTGAGCGTCAGAC
5980 CCCGTAGAAAAGATCAAAGGATCTTCTTGAGATCCTTTT
6019 TTTCTGCGCGTAATCTGCTGCTTGCAAACAAAAAAACCA
6058 CCGCTACCAGCGGTGGTTTGTTTGCCGGATCAAGAGCTA
6097 CCAACTCTTTTTCCGAAGGTAACTGGCTTCAGCAGAGCG
```

Fig.13o

```
6136  CAGATACCAAATACTGTCCTTCTAGTGTAGCCGTAGTTA
6175  GGCCACCACTTCAAGAACTCTGTAGCACCGCCTACATAC
6214  CTCGCTCTGCTAATCCTGTTACCAGTGGCTGCTGCCAGT
6253  GGCGATAAGTCGTGTCTTACCGGGTTGGACTCAAGACGA
6292  TAGTTACCGGATAAGGCGCAGCGGTCGGGCTGAACGGGG
6331  GGTTCGTGCACACAGCCCAGCTTGGAGCGAACGACCTAC
6370  ACCGAACTGAGATACCTACAGCGTGAGCTATGAGAAAGC
6409  GCCACGCTTCCCGAAGGGAGAAAGGCGGACAGGTATCCG
6448  GTAAGCGGCAGGGTCGGAACAGGAGAGCGCACGAGGGAG
6487  CTTCCAGGGGGAAACGCCTGGTATCTTTATAGTCCTGTC
6526  GGGTTTCGCCACCTCTGACTTGAGCGTCGATTTTTGTGA
6565  TGCTCGTCAGGGGGGCGGAGCCTATGGAAAAACGCCAGC
6604  AACGCGGCCTTTTTACGGTTCCTGGCCTTTTGCTGGCCT
6643  TTTGCTCACATGTTCTTTCCTGCGTTATCCCCTGATTCT
6682  GTGGATAACCGTATTACCGCCTTTGAGTGAGCTGATACC
6721  GCTCGCCGCAGCCGAACGACCGAGCGCAGCGAGTCAGTG
6760  AGCGAGGAAGCGGAAGAGCGCCTGATGCGGTATTTTCTC
6799  CTTACGCATCTGTGCGGTATTTCACACCGCATAGGGTCA
6838  TGGCTGCGCCCCGACACCCGCCAACACCCGCTGACGCGC
6877  CCTGACGGGCTTGTCTGCTCCCGGCATCCGCTTACAGAC
6916  AAGCTGTGACCGTCTCCGGGAGCTGCATGTGTCAGAGGT
6955  TTTCACCGTCATCACCGAAACGCGCGAGGCAGCAAGGAG
```

Fig.13p

```
6994  ATGGCGCCCAACAGTCCCCCGGCCACGGGGCCTGCCACC
7033  ATACCCACGCCGAAACAAGCGCTCATGAGCCCGAAGTGG
7072  CGAGCCCGATCTTCCCCATCGGTGATGTCGGCGATATAG
7111  GCGCCAGCAACCGCACCTGTGGCGCCGGTGATGCCGGCC
7150  ACGATGCGTCCGGCGTAGAGGATCTGCTCATGTTTGACA
7189  GCTTATC
```

Fig.14b

```
           NsiI
  1  ATCGATGCATAATGTGCCTGTCAAATGGACGAAGCAGGG

40  ATTCTGCAAACCCTATGCTACTCCGTCAAGCCGTCAATT

79  GTCTGATTCGTTACCAA TTA TGA CAA CTT GAC
                   293◄ ••• Ser Leu Lys Val

111  GGC TAC ATC ATT CAC TTT TTC TTC ACA ACC
288◄ Ala Val Asp Asn Val Lys Glu Glu Cys Gly

141  GGC ACG GAA CTC GCT CGG GCT GGC CCC GGT
278◄ Ala Arg Phe Glu Ser Pro Ser Ala Gly Thr

171  GCA TTT TTT AAA TAC CCG CGA GAA ATA GAG
268◄ Cys Lys Lys Phe Val Arg Ser Phe Tyr Leu

201  TTG ATC GTC AAA ACC AAC ATT GCG ACC GAC
258◄ Gln Asp Asp Phe Gly Val Asn Arg Gly Val

231  GGT GGC GAT AGG CAT CCG GGT GGT GCT CAA
248◄ Thr Ala Ile Pro Met Arg Thr Thr Ser Leu

261  AAG CAG CTT CGC CTG GCT GAT ACG TTG GTC
238◄ Leu Leu Lys Ala Gln Ser Ile Arg Gln Asp

291  CTC GCG CCA GCT TAA GAC GCT AAT CCC TAA
228◄ Glu Arg Trp Ser Leu Val Ser Ile Gly Leu

321  CTG CTG GCG GAA AAG ATG TGA CAG ACG CGA
218◄ Gln Gln Arg Phe Leu His Ser Leu Arg Ser

351  CGG CGA CAA GCA AAC ATG CTG TGC GAC GCT
208◄ Pro Ser Leu Cys Val His Gln Ala Val Ser
             EcoRV
381  GGC GAT ATC AAA ATT GCT GTC TGC CAG GTG
198◄ Ala Ile Asp Phe Asn Ser Asp Ala Leu His
```

Fig.14c

```
411 ATC GCT GAT GTA CTG ACA AGC CTC GCG TAC
188◄Asp Ser Ile Tyr Gln Cys Ala Glu Arg Val

441 CCG ATT ATC CAT CGG TGG ATG GAG CGA CTC
178◄Arg Asn Asp Met Pro Pro His Leu Ser Glu

471 GTT AAT CGC TTC CAT GCG CCG CAG TAA CAA
168◄Asn Ile Ala Glu Met Arg Arg Leu Leu Leu

501 TTG CTC AAG CAG ATT TAT CGC CAG CAG CTC
158◄Gln Glu Leu Leu Asn Ile Ala Leu Leu Glu

531 CGA ATA GCG CCC TTC CCC TTG CCC GGC GTT
148◄Ser Tyr Arg Gly Glu Gly Gln Gly Ala Asn

561 AAT GAT TTG CCC AAA CAG GTC GCT GAA ATG
138◄Ile Ile Gln Gly Phe Leu Asp Ser Phe His

591 CGG CTG GTG CGC TTC ATC CGG GCG AAA GAA
128◄Pro Gln His Ala Glu Asp Pro Arg Phe Phe

621 CCC CGT ATT GGC AAA TAT TGA CGG CCA GTT
118◄Gly Thr Asn Ala Phe Ile Ser Pro Trp Asn

651 AAG CCA TTC ATG CCA GTA GGC GCG CGG ACG
108◄Leu Trp Glu His Trp Tyr Ala Arg Pro Arg

681 AAA GTA AAC CCA CTG GTG ATA CCA TTC GCG
 98◄Phe Tyr Val Trp Gln His Tyr Trp Glu Arg

711 AGC CTC CGG ATG ACG ACC GTA GTG ATG AAT
 88◄Ala Glu Pro His Arg Gly Tyr His His Ile

741 CTC TCC TGG CGG GAA CAG CAA AAT ATC ACC
 78◄Glu Gly Pro Pro Phe Leu Leu Ile Asp Gly

771 CGG TCG GCA AAC AAA TTC TCG TCC CTG ATT
 68◄Pro Arg Cys Val Phe Glu Arg Gly Gln Asn
```

Fig.14d

```
 801 TTT CAC CAC CCC CTG ACC GCG AAT GGT GAG
  58◄Lys Val Val Gly Gln Gly Arg Ile Thr Leu
 831 ATT GAG AAT ATA ACC TTT CAT TCC CAG CGG
  48◄Asn Leu Ile Tyr Gly Lys Met Gly Leu Pro
 861 TCG GTC GAT AAA AAA ATC GAG ATA ACC GTT
  38◄Arg Asp Ile Phe Phe Asp Leu Tyr Gly Asn
 891 GGC CTC AAT CGG CGT TAA ACC CGC CAC CAG
  28◄Ala Glu Ile Pro Thr Leu Gly Ala Val Leu
 921 ATG GGC ATT AAA CGA GTA TCC CGG CAG CAG
  18◄His Ala Asn Phe Ser Tyr Gly Pro Leu Leu
 951 GGG ATC ATT TTG CGC TTC AGC CAT ACTTTTC
   8◄Pro Asp Asn Gln Ala Glu Ala Met
 982 ATACTCCCGCCATTCAGAGAAGAAACCAATTGTCCATAT
1021 TGCATCAGACATTGCCGTCACTGCGTCTTTTACTGGCTC
1060 TTCTCGCTAACCAAACCGGTAACCCCGCTTATTAAAAGC
1099 ATTCTGTAACAAAGCGGGACCAAAGCCATGACAAAAACG
1138 CGTAACAAAAGTGTCTATAATCACGGCAGAAAAGTCCAC
1177 ATTGATTATTTGCACGGCGTCACACTTTGCTATGCCATA
                                      BamHI
1216 GCATTTTTATCCATAAGATTAGCGGATCCTACCTGACGC
1255 TTTTTATCGCAACTCTCTACTGTTTCTCCATACCCGTTT
          NheI            EcoRI
1294 TTTTGGGCTAGCAGGAGGAATTCACC ATG ACA CCG
                                   1►Met Thr Pro
                  PstI
1329 GAC ATT ATC CTG CAG CGT ACC GGG ATC GAT
```

Fig.14e

```
   4▶Asp  Ile  Ile  Leu  Gln  Arg  Thr  Gly  Ile  Asp
1359 GTG  AGA  GCT  GTC  GAA  CAG  GGG  GAT  GAT  GCG
  14▶Val  Arg  Ala  Val  Glu  Gln  Gly  Asp  Asp  Ala
1389 TGG  CAC  AAA  TTA  CGG  CTC  GGC  GTC  ATC  ACC
  24▶Trp  His  Lys  Leu  Arg  Leu  Gly  Val  Ile  Thr
1419 GCT  TCA  GAA  GTT  CAC  AAC  GTG  ATA  GCA  AAA
  34▶Ala  Ser  Glu  Val  His  Asn  Val  Ile  Ala  Lys
1449 CCC  CGC  TCC  GGA  AAG  AAG  TGG  CCT  GAC  ATG
  44▶Pro  Arg  Ser  Gly  Lys  Lys  Trp  Pro  Asp  Met
1479 AAA  ATG  TCC  TAC  TTC  CAC  ACC  CTG  CTT  GCT
  54▶Lys  Met  Ser  Tyr  Phe  His  Thr  Leu  Leu  Ala
1509 GAG  GTT  TGC  ACC  GGT  GTG  GCT  CCG  GAA  GTT
  64▶Glu  Val  Cys  Thr  Gly  Val  Ala  Pro  Glu  Val
1539 AAC  GCT  AAA  GCA  CTG  GCC  TGG  GGA  AAA  CAG
  74▶Asn  Ala  Lys  Ala  Leu  Ala  Trp  Gly  Lys  Gln
                                                    EcoRI
1569 TAC  GAG  AAC  GAC  GCC  AGA  ACC  CTG  TTT  GAA
  84▶Tyr  Glu  Asn  Asp  Ala  Arg  Thr  Leu  Phe  Glu
1599 TTC  ACT  TCC  GGC  GTG  AAT  GTT  ACT  GAA  TCC
  94▶Phe  Thr  Ser  Gly  Val  Asn  Val  Thr  Glu  Ser
1629 CCG  ATC  ATC  TAT  CGC  GAC  GAA  AGT  ATG  CGT
 104▶Pro  Ile  Ile  Tyr  Arg  Asp  Glu  Ser  Met  Arg
1659 ACC  GCC  TGC  TCT  CCC  GAT  GGT  TTA  TGC  AGT
 114▶Thr  Ala  Cys  Ser  Pro  Asp  Gly  Leu  Cys  Ser
1689 GAC  GGC  AAC  GGC  CTT  GAA  CTG  AAA  TGC  CCG
 124▶Asp  Gly  Asn  Gly  Leu  Glu  Leu  Lys  Cys  Pro
```

Fig.14f

```
1719 TTT ACC TCC CGG GAT TTC ATG AAG TTC CGG
134▶Phe Thr Ser Arg Asp Phe Met Lys Phe Arg
1749 CTC GGT GGT TTC GAG GCC ATA AAG TCA GCT
144▶Leu Gly Gly Phe Glu Ala Ile Lys Ser Ala
1779 TAC ATG GCC CAG GTG CAG TAC AGC ATG TGG
154▶Tyr Met Ala Gln Val Gln Tyr Ser Met Trp
1809 GTG ACG CGA AAA AAT GCC TGG TAC TTT GCC
164▶Val Thr Arg Lys Asn Ala Trp Tyr Phe Ala
1839 AAC TAT GAC CCG CGT ATG AAG CGT GAA GGC
174▶Asn Tyr Asp Pro Arg Met Lys Arg Glu Gly
1869 CTG CAT TAT GTC GTG ATT GAG CGG GAT GAA
184▶Leu His Tyr Val Val Ile Glu Arg Asp Glu
1899 AAG TAC ATG GCG AGT TTT GAC GAG ATC GTG
194▶Lys Tyr Met Ala Ser Phe Asp Glu Ile Val
1929 CCG GAG TTC ATC GAA AAA ATG GAC GAG GCA
204▶Pro Glu Phe Ile Glu Lys Met Asp Glu Ala
1959 CTG GCT GAA ATT GGT TTT GTA TTT GGG GAG
214▶Leu Ala Glu Ile Gly Phe Val Phe Gly Glu
                              KpnI
1989 CAA TGG CGA TAGATCCGGTACCCGAGCACGTGTTGA
224▶Gln Trp Arg •••
2025 CAATTAATCATCGGCATAGTATATCGGCATAGTATAATA
2064 CGACAAGGTGAGGAACTAAACC ATG AGT ACT GCA
                              1▶Met Ser Thr Ala
2098 CTC GCA ACG CTG GCT GGG AAG CTG GCT GAA
5▶Leu Ala Thr Leu Ala Gly Lys Leu Ala Glu
```

Fig.14g

```
                                                 SalI
2128 CGT GTC GGC ATG GAT TCT GTC GAC CCA CAG
  15▶Arg Val Gly Met Asp Ser Val Asp Pro Gln

2158 GAA CTG ATC ACC ACT CTT CGC CAG ACG GCA
  25▶Glu Leu Ile Thr Thr Leu Arg Gln Thr Ala

2188 TTT AAA GGT GAT GCC AGC GAT GCG CAG TTC
  35▶Phe Lys Gly Asp Ala Ser Asp Ala Gln Phe

2218 ATC GCA TTA CTG ATC GTT GCC AAC CAG TAC
  45▶Ile Ala Leu Leu Ile Val Ala Asn Gln Tyr

2248 GGC CTT AAT CCG TGG ACG AAA GAA ATT TAC
  55▶Gly Leu Asn Pro Trp Thr Lys Glu Ile Tyr

2278 GCC TTT CCT GAT AAG CAG AAT GGC ATC GTT
  65▶Ala Phe Pro Asp Lys Gln Asn Gly Ile Val

2308 CCG GTG GTG GGC GTT GAT GGC TGG TCC CGC
  75▶Pro Val Val Gly Val Asp Gly Trp Ser Arg

2338 ATC ATC AAT GAA AAC CAG CAG TTT GAT GGC
  85▶Ile Ile Asn Glu Asn Gln Gln Phe Asp Gly

2368 ATG GAC TTT GAG CAG GAC AAT GAA TCC TGT
  95▶Met Asp Phe Glu Gln Asp Asn Glu Ser Cys

2398 ACA TGC CGG ATT TAC CGC AAG GAC CGT AAT
 105▶Thr Cys Arg Ile Tyr Arg Lys Asp Arg Asn

2428 CAT CCG ATC TGC GTT ACC GAA TGG ATG GAT
 115▶His Pro Ile Cys Val Thr Glu Trp Met Asp

2458 GAA TGC CGC CGC GAA CCA TTC AAA ACT CGC
 125▶Glu Cys Arg Arg Glu Pro Phe Lys Thr Arg

2488 GAA GGC AGA GAA ATC ACG GGG CCG TGG CAG
 135▶Glu Gly Arg Glu Ile Thr Gly Pro Trp Gln
```

Fig.14h

```
2518  TCG  CAT  CCC  AAA  CGG  ATG  TTA  CGT  CAT  AAA
145▶  Ser  His  Pro  Lys  Arg  Met  Leu  Arg  His  Lys

2548  GCC  ATG  ATT  CAG  TGT  GCC  CGT  CTG  GCC  TTC
155▶  Ala  Met  Ile  Gln  Cys  Ala  Arg  Leu  Ala  Phe

2578  GGA  TTT  GCT  GGT  ATC  TAT  GAC  AAG  GAT  GAA
165▶  Gly  Phe  Ala  Gly  Ile  Tyr  Asp  Lys  Asp  Glu

2608  GCC  GAG  CGC  ATT  GTC  GAA  AAT  ACT  GCA  TAC
175▶  Ala  Glu  Arg  Ile  Val  Glu  Asn  Thr  Ala  Tyr
                              PstI
2638  ACT  GCA  GAA  CGT  CAG  CCG  GAA  CGC  GAC  ATC
185▶  Thr  Ala  Glu  Arg  Gln  Pro  Glu  Arg  Asp  Ile

2668  ACT  CCG  GTT  AAC  GAT  GAA  ACC  ATG  CAG  GAG
195▶  Thr  Pro  Val  Asn  Asp  Glu  Thr  Met  Gln  Glu

2698  ATT  AAC  ACT  CTG  CTG  ATC  GCC  CTG  GAT  AAA
205▶  Ile  Asn  Thr  Leu  Leu  Ile  Ala  Leu  Asp  Lys

2728  ACA  TGG  GAT  GAC  GAC  TTA  TTG  CCG  CTC  TGT
215▶  Thr  Trp  Asp  Asp  Asp  Leu  Leu  Pro  Leu  Cys

2758  TCC  CAG  ATA  TTT  CGC  CGC  GAC  ATT  CGT  GCA
225▶  Ser  Gln  Ile  Phe  Arg  Arg  Asp  Ile  Arg  Ala

2788  TCG  TCA  GAA  CTG  ACA  CAG  GCC  GAA  GCA  GTA
235▶  Ser  Ser  Glu  Leu  Thr  Gln  Ala  Glu  Ala  Val

2818  AAA  GCT  CTT  GGA  TTC  CTG  AAA  CAG  AAA  GCC
245▶  Lys  Ala  Leu  Gly  Phe  Leu  Lys  Gln  Lys  Ala
                                           BglII Xhol
2848  GCA  GAG  CAG  AAG  GTG  GCA  GCA  TAGATCTCGAG
255▶  Ala  Glu  Gln  Lys  Val  Ala  Ala  •••
```

Fig.14i

```
     HindIII
2880 AAGCTTCCTGCTGAACATCAAAGGCAAGAAAACATCTGT
2919 TGTCAAAGACAGCATCCTTGAACAAGGACAATTAACAGT
2958 TAACAAATAAAAACGCAAAAGAAAATGCCGATATCCTAT
2997 TGGCATTTTCTTTTATTTCTTATCAACATAAAGGTGAAT
         XhoI
3036 CCCATACCTCGAGCTTCACGCTGCCGCAAGCACTCAGGG
3075 CGCAAGGGCTGCTAAAAGGAAGCGGAACACGTAGAAAGC
3114 CAGTCCGCAGAAACGGTGCTGACCCCGGATGAATGTCAG
3153 CTACTGGGCTATCTGGACAAGGGAAAACGCAAGCGCAAA
3192 GAGAAAGCAGGTAGCTTGCAGTGGGCTTACATGGCGATA
3231 GCTAGACTGGGCGGTTTTATGGACAGCAAGCGAACCGGA
         PvuII
3270 ATTGCCAGCTGGGGCGCCCTCTGGTAAGGTTGGGAAGCC
3309 CTGCAAAGTAAACTGGATGGCTTTCTTGCCGCCAAGGAT
              BglII
3348 CTGATGGCGCAGGGGATCAAGATCTGATCAAGAGACAGG
3387 ATGAGGATCGTTTCGC ATG GAT ATT AAT ACT
                   1▶Met Asp Ile Asn Thr
3418 GAA ACT GAG ATC AAG CAA AAG CAT TCA CTA
   6▶Glu Thr Glu Ile Lys Gln Lys His Ser Leu
3448 ACC CCC TTT CCT GTT TTC CTA ATC AGC CCG
  16▶Thr Pro Phe Pro Val Phe Leu Ile Ser Pro
3478 GCA TTT CGC GGG CGA TAT TTT CAC AGC TAT
  26▶Ala Phe Arg Gly Arg Tyr Phe His Ser Tyr
3508 TTC AGG AGT TCA GCC ATG AAC GCT TAT TAC
  36▶Phe Arg Ser Ser Ala Met Asn Ala Tyr Tyr
```

Fig.14j

```
3538 ATT CAG GAT CGT CTT GAG GCT CAG AGC TGG
  46▶ Ile Gln Asp Arg Leu Glu Ala Gln Ser Trp
3568 GCG CGT CAC TAC CAG CAG CTC GCC CGT GAA
  56▶ Ala Arg His Tyr Gln Gln Leu Ala Arg Glu
3598 GAG AAA GAG GCA GAA CTG GCA GAC GAC ATG
  66▶ Glu Lys Glu Ala Glu Leu Ala Asp Asp Met
3628 GAA AAA GGC CTG CCC CAG CAC CTG TTT GAA
  76▶ Glu Lys Gly Leu Pro Gln His Leu Phe Glu
3658 TCG CTA TGC ATC GAT CAT TTG CAA CGC CAC
  86▶ Ser Leu Cys Ile Asp His Leu Gln Arg His
3688 GGG GCC AGC AAA AAA TCC ATT ACC CGT GCG
  96▶ Gly Ala Ser Lys Lys Ser Ile Thr Arg Ala
3718 TTT GAT GAC GAT GTT GAG TTT CAG GAG CGC
 106▶ Phe Asp Asp Asp Val Glu Phe Gln Glu Arg
3748 ATG GCA GAA CAC ATC CGG TAC ATG GTT GAA
 116▶ Met Ala Glu His Ile Arg Tyr Met Val Glu
3778 ACC ATT GCT CAC CAC CAG GTT GAT ATT GAT
 126▶ Thr Ile Ala His His Gln Val Asp Ile Asp
                                    HindIII
3808 TCA GAG GTA TAA AACGAGTAGA AGC TTG GCT
 136▶ Ser Glu Val •••
3839 GTT TTG GCG GAT GAG AGA AGA TTT TCA GCC
3869 TGA TACAGATTAAATCAGAACGCAGAAGCGGTCTGATA
3907 AAACAGAATTTGCCTGGCGGCAGTAGCGCGGTGGTCCCA
3946 CCTGACCCCATGCCGAACTCAGAAGTGAAACGCCGTAGC
3985 GCCGATGGTAGTGTGGGGTCTCCCCATGCGAGAGTAGGG
```

Fig.14k

```
4024 AACTGCCAGGCATCAAATAAAACGAAAGGCTCAGTCGAA
4063 AGACTGGGCCTTTCGTTTTATCTGTTGTTTGTCGGTGAA
4102 CGCTCTCCTGAGTAGGACAAATCCGCCGGGAGCGGATTT
4141 GAACGTTGCGAAGCAACGGCCCGGAGGGTGGCGGGCAGG
4180 ACGCCCGCCATAAACTGCCAGGCATCAAATTAAGCAGAA
4219 GGCCATCCTGACGGATGGCCTTTTTGCGTTTCTACAAAC
4258 TCTTTTGTTTATTTTTCTAAATACATTCAAATATGTATC
4297 CGCTCATGAGACAATAACCCTGATAAATGCTTCAATAAT
4336 ATTGAAAAGGAAGAGT ATG AGT ATT CAA CAT
                    1▸Met Ser Ile Gln His
4368 TTC CGT GTC GCC CTT ATT CCC TTT TTT GCG
   6▸Phe Arg Val Ala Leu Ile Pro Phe Phe Ala
4398 GCA TTT TGC CTT CCT GTT TTT GCT CAC CCA
  16▸Ala Phe Cys Leu Pro Val Phe Ala His Pro
4428 GAA ACG CTG GTG AAA GTA AAA GAT GCT GAA
  26▸Glu Thr Leu Val Lys Val Lys Asp Ala Glu
4458 GAT CAG TTG GGT GCA CGA GTG GGT TAC ATC
  36▸Asp Gln Leu Gly Ala Arg Val Gly Tyr Ile
4488 GAA CTG GAT CTC AAC AGC GGT AAG ATC CTT
  46▸Glu Leu Asp Leu Asn Ser Gly Lys Ile Leu
4518 GAG AGT TTT CGC CCC GAA GAA CGT TTT CCA
  56▸Glu Ser Phe Arg Pro Glu Glu Arg Phe Pro
4548 ATG ATG AGC ACT TTT AAA GTT CTG CTA TGT
  66▸Met Met Ser Thr Phe Lys Val Leu Leu Cys
```

Fig.14I

```
4578 GGC GCG GTA TTA TCC CGT GTT GAC GCC GGG
  76▶Gly Ala Val Leu Ser Arg Val Asp Ala Gly
4608 CAA GAG CAA CTC GGT CGC CGC ATA CAC TAT
  86▶Gln Glu Gln Leu Gly Arg Arg Ile His Tyr
                                        ScaI
4638 TCT CAG AAT GAC TTG GTT GAG TAC TCA CCA
  96▶Ser Gln Asn Asp Leu Val Glu Tyr Ser Pro
4668 GTC ACA GAA AAG CAT CTT ACG GAT GGC ATG
 106▶Val Thr Glu Lys His Leu Thr Asp Gly Met
4698 ACA GTA AGA GAA TTA TGC AGT GCT GCC ATA
 116▶Thr Val Arg Glu Leu Cys Ser Ala Ala Ile
4728 ACC ATG AGT GAT AAC ACT GCG GCC AAC TTA
 126▶Thr Met Ser Asp Asn Thr Ala Ala Asn Leu
4758 CTT CTG ACA ACG ATC GGA GGA CCG AAG GAG
 136▶Leu Leu Thr Thr Ile Gly Gly Pro Lys Glu
4788 CTA ACC GCT TTT TTG CAC AAC ATG GGG GAT
 146▶Leu Thr Ala Phe Leu His Asn Met Gly Asp
4818 CAT GTA ACT CGC CTT GAT CGT TGG GAA CCG
 156▶His Val Thr Arg Leu Asp Arg Trp Glu Pro
4848 GAG CTG AAT GAA GCC ATA CCA AAC GAC GAG
 166▶Glu Leu Asn Glu Ala Ile Pro Asn Asp Glu
4878 CGT GAC ACC ACG ATG CCT GTA GCA ATG GCA
 176▶Arg Asp Thr Thr Met Pro Val Ala Met Ala
4908 ACA ACG TTG CGC AAA CTA TTA ACT GGC GAA
 186▶Thr Thr Leu Arg Lys Leu Leu Thr Gly Glu
4938 CTA CTT ACT CTA GCT TCC CGG CAA CAA TTA
 196▶Leu Leu Thr Leu Ala Ser Arg Gln Gln Leu
```

Fig.14m

```
4968 ATA GAC TGG ATG GAG GCG GAT AAA GTT GCA
 206▶Ile Asp Trp Met Glu Ala Asp Lys Val Ala

4998 GGA CCA CTT CTG CGC TCG GCC CTT CCG GCT
 216▶Gly Pro Leu Leu Arg Ser Ala Leu Pro Ala

5028 GGC TGG TTT ATT GCT GAT AAA TCT GGA GCC
 226▶Gly Trp Phe Ile Ala Asp Lys Ser Gly Ala

5058 GGT GAG CGT GGG TCT CGC GGT ATC ATT GCA
 236▶Gly Glu Arg Gly Ser Arg Gly Ile Ile Ala

5088 GCA CTG GGG CCA GAT GGT AAG CCC TCC CGT
 246▶Ala Leu Gly Pro Asp Gly Lys Pro Ser Arg

5118 ATC GTA GTT ATC TAC ACG ACG GGG AGT CAG
 256▶Ile Val Val Ile Tyr Thr Thr Gly Ser Gln

5148 GCA ACT ATG GAT GAA CGA AAT AGA CAG ATC
 266▶Ala Thr Met Asp Glu Arg Asn Arg Gln Ile

5178 GCT GAG ATA GGT GCC TCA CTG ATT AAG CAT
 276▶Ala Glu Ile Gly Ala Ser Leu Ile Lys His

5208 TGG TAA CTGTCAGACCAAGTTTACTCATATATACTTT
 286▶Trp ***

5245 AGATTGATTTACGCGCCCTGTAGCGGCGCATTAAGCGCG
5284 GCGGGTGTGGTGGTTACGCGCAGCGTGACCGCTACACTT
5323 GCCAGCGCCCTAGCGCCCGCTCCTTTCGCTTTCTTCCCT
5362 TCCTTTCTCGCCACGTTCGCCGGCTTTCCCCGTCAAGCT
5401 CTAAATCGGGGGCTCCCTTTAGGGTTCCGATTTAGTGCT
5440 TTACGGCACCTCGACCCCAAAAAACTTGATTTGGGTGAT
5479 GGTTCACGTAGTGGGCCATCGCCCTGATAGACGGTTTTT
```

Fig.14n

```
5518  CGCCCTTTGACGTTGGAGTCCACGTTCTTTAATAGTGGA
5557  CTCTTGTTCCAAACTTGAACAACACTCAACCCTATCTCG
5596  GGCTATTCTTTTGATTTATAAGGGATTTTGCCGATTTCG
5635  GCCTATTGGTTAAAAATGAGCTGATTTAACAAAAATTT
5674  AACGCGAATTTTAACAAATATTAACGTTTACAATTTAA
5713  AAGGATCTAGGTGAAGATCCTTTTTGATAATCTCATGAC
5752  CAAAATCCCTTAACGTGAGTTTTCGTTCCACTGAGCGTC
5791  AGACCCCGTAGAAAAGATCAAAGGATCTTCTTGAGATCC
5830  TTTTTTTCTGCGCGTAATCTGCTGCTTGCAAACAAAAAA
5869  ACCACCGCTACCAGCGGTGGTTTGTTTGCCGGATCAAGA
5908  GCTACCAACTCTTTTTCCGAAGGTAACTGGCTTCAGCAG
5947  AGCGCAGATACCAAATACTGTCCTTCTAGTGTAGCCGTA
5986  GTTAGGCCACCACTTCAAGAACTCTGTAGCACCGCCTAC
6025  ATACCTCGCTCTGCTAATCCTGTTACCAGTGGCTGCTGC
6064  CAGTGGCGATAAGTCGTGTCTTACCGGGTTGGACTCAAG
6103  ACGATAGTTACCGGATAAGGCGCAGCGGTCGGGCTGAAC
6142  GGGGGGTTCGTGCACACAGCCCAGCTTGGAGCGAACGAC
6181  CTACACCGAACTGAGATACCTACAGCGTGAGCTATGAGA
6220  AAGCGCCACGCTTCCCGAAGGGAGAAAGGCGGACAGGTA
6259  TCCGGTAAGCGGCAGGGTCGGAACAGGAGAGCGCACGAG
6298  GGAGCTTCCAGGGGGAAACGCCTGGTATCTTTATAGTCC
6337  TGTCGGGTTTCGCCACCTCTGACTTGAGCGTCGATTTTT
```

Fig.14o

| | |
|---|---|
| 6376 | GTGATGCTCGTCAGGGGGGCGGAGCCTATGGAAAAACGC |
| 6415 | CAGCAACGCGGCCTTTTTACGGTTCCTGGCCTTTTGCTG |
| 6454 | GCCTTTTGCTCACATGTTCTTTCCTGCGTTATCCCCTGA |
| 6493 | TTCTGTGGATAACCGTATTACCGCCTTTGAGTGAGCTGA |
| 6532 | TACCGCTCGCCGCAGCCGAACGACCGAGCGCAGCGAGTC |
| 6571 | AGTGAGCGAGGAAGCGGAAGAGCGCCTGATGCGGTATTT |
| 6610 | TCTCCTTACGCATCTGTGCGGTATTTCACACCGCATAGG |
| 6649 | GTCATGGCTGCGCCCCGACACCCGCCAACACCCGCTGAC |
| 6688 | GCGCCCTGACGGGCTTGTCTGCTCCCGGCATCCGCTTAC |
| 6727 | AGACAAGCTGTGACCGTCTCCGGGAGCTGCATGTGTCAG |
| 6766 | AGGTTTTCACCGTCATCACCGAAACGCGCGAGGCAGCAA |
| 6805 | GGAGATGGCGCCCAACAGTCCCCCGGCCACGGGGCCTGC |
| 6844 | CACCATACCCACGCCGAAACAAGCGCTCATGAGCCCGAA |
| 6883 | GTGGCGAGCCCGATCTTCCCCATCGGTGATGTCGGCGAT |
| 6922 | ATAGGCGCCAGCAACCGCACCTGTGGCGCCGGTGATGCC |
| 6961 | GGCCACGATGCGTCCGGCGTAGAGGATCTGCTCATGTTT |
| 7000 | GACAGCTTATC |

SEQUENCE LISTING

<160> NUMBER OF SEQ ID NOS: 14

<210> SEQ ID NO 1
<211> LENGTH: 6150
<212> TYPE: DNA
<213> ORGANISM: Artificial Sequence
<220> FEATURE:
<221> NAME/KEY: misc_feature
<222> LOCATION: (1)..(6150)
<223> OTHER INFORMATION: plasmid pBAD24-rec ET
<221> NAME/KEY: misc_feature
<222> LOCATION: (96)..(974)
<223> OTHER INFORMATION: product = "araC"
<221> NAME/KEY: misc_feature
<222> LOCATION: (1320)..(2162)
<223> OTHER INFORMATION: product = "t-recE"
<221> NAME/KEY: misc_feature
<222> LOCATION: (2155)..(2972)
<223> OTHER INFORMATION: product = "recT"
<221> NAME/KEY: misc_feature
<222> LOCATION: (3493)..(4353)
<223> OTHER INFORMATION: product = "bla"

<400> SEQUENCE: 1

```
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcacttttt cttcacaacc ggcacggaac tcgctcgggc tggccccggt gcatttttta     180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttccccct gcccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattgcgc agcctccgga     720
tgacgaccgt agtgatgaat ctctcctggc gggaacagca aaatatcacc cggtcggcaa     780
acaaattctc gtccctgatt tttcaccacc ccctgaccgc gaatggtgag attgagaata     840
```

-continued

```
taacctttca ttcccagcgg tcggtcgata aaaaaatcga gataaccgtt ggcctcaatc      900
ggcgttaaac ccgccaccag atgggcatta aacgagtatc ccggcagcag gggatcattt      960
tgcgcttcag ccatactttt catactcccg ccattcagag aagaaaccaa ttgtccatat     1020
tgcatcagac attgccgtca ctgcgtcttt tactggctct tctcgctaac caaaccggta     1080
accccgctta ttaaaagcat tctgtaacaa agcgggacca agccatgac aaaaacgcgt      1140
aacaaaagtg tctataatca cggcagaaaa gtccacattg attatttgca cggcgtcaca     1200
ctttgctatg ccatagcatt tttatccata agattagcgg atcctacctg acgcttttta     1260
tcgcaactct ctactgtttc tccatacccg ttttttggg ctagcaggag gaattcacca      1320
tggatcccgt aatcgtagaa gacatagagc caggtattta ttacggaatt cgaatgaga     1380
attaccacgc gggtcccggt atcagtaagt ctcagctcga tgacattgct gatactccgg     1440
cactatattt gtggcgtaaa aatgcccccg tggacaccac aaagacaaaa acgctcgatt     1500
taggaactgc tttccactgc cgggtacttg aaccggaaga attcagtaac cgctttatcg     1560
tagcacctga atttaaccgc cgtacaaacg ccggaaaaga agaagagaaa gcgtttctga     1620
tggaatgcgc aagcacagga aaaacggtta tcactgcgga agaaggccgg aaaattgaac     1680
tcatgtatca aagcgttatg gctttgccgc tggggcaatg gcttgttgaa agcgccggac     1740
acgctgaatc atcaatttac tgggaagatc ctgaaacagg aattttgtgt cggtgccgtc     1800
cggacaaaat tatccctgaa tttcactgga tcatggacgt gaaaactacg gcggatattc     1860
aacgattcaa aaccgcttat tacgactacc gctatcacgt tcaggatgca ttctacagtg     1920
acggttatga agcacagttt ggagtgcagc caactttcgt ttttctggtt gccagcacaa     1980
ctattgaatg cggacgttat ccggttgaaa ttttcatgat gggcgaagaa gcaaaactgg     2040
caggtcaaca ggaatatcac cgcaatctgc gaaccctgtc tgactgcctg aataccgatg     2100
aatggccagc tattaagaca ttatcactgc cccgctgggc taaggaatat gcaaatgact     2160
aagcaaccac caatcgcaaa agccgatctg caaaaaactc agggaaaccg tgcaccagca     2220
gcagttaaaa atagcgacgt gattagtttt attaaccagc catcaatgaa agagcaactg     2280
gcagcagctc ttccacgcca tatgacggct gaacgtatga tccgtatcgc caccacagaa     2340
attcgtaaag ttccggcgtt aggaaactgt gacactatga gttttgtcag tgcgatcgta     2400
cagtgttcac agctcggact tgagccaggt agcgccctcg gtcatgcata tttactgcct     2460
tttggtaata aaaacgaaaa gagcggtaaa agaacgttc agctaatcat ggctatcgc      2520
ggcatgattg atctggctcg ccgttctggt caaatcgcca gcctgtcagc ccgtgttgtc     2580
cgtgaaggtg acgagtttag cttcgaattt ggccttgatg aaaagttaat acaccgcccg     2640
ggagaaaacg aagatgcccc ggttacccac gtctatgctg tcgcaagact gaaagacgga     2700
ggtactcagt ttgaagttat gacgcgcaaa cagattgagc tggtgcgcag cctgagtaaa     2760
gctggtaata acgggccgtg ggtaactcac tgggaagaaa tggcaaagaa aacggctatt     2820
cgtcgcctgt tcaaatattt gcccgtatca attgagatcc agcgtgcagt atcaatggat     2880
gaaaaggaac cactgacaat cgatcctgca gattcctctg tattaaccgg ggaatacagt     2940
gtaatcgata attcagagga atagatctaa gcttggctgt tttggcggat gagagaagat     3000
tttcagcctg atacagatta aatcagaacg cagaagcggt ctgataaaac agaatttgcc     3060
tggcggcagt agcgcggtgg tcccacctga ccccatgccg aactcagaag tgaaacgccg     3120
tagcgccgat ggtagtgtgg ggtctcccca tgcgagagta gggaactgcc aggcatcaaa     3180
taaaacgaaa ggctcagtcg aaagactggg cctttcgttt tatctgttgt ttgtcggtga     3240
```

-continued

```
acgctctcct gagtaggaca aatccgccgg gagcggattt gaacgttgcg aagcaacggc    3300
ccggagggtg gcgggcagga cgcccgccat aaactgccag gcatcaaatt aagcagaagg    3360
ccatcctgac ggatggcctt tttgcgtttc tacaaactct tttgtttatt tttctaaata    3420
cattcaaata tgtatccgct catgagacaa taaccctgat aaatgcttca ataatattga    3480
aaaaggaaga gtatgagtat tcaacatttc cgtgtcgccc ttattccctt ttttgcggca    3540
ttttgccttc ctgttttgc tcacccagaa acgctggtga agtaaaaga tgctgaagat    3600 cagttgggtg cacgagtggg ttacatcgaa ctggatctca acagcggtaa gatccttgag    3660
agttttcgcc ccgaagaacg ttttccaatg atgagcactt taaagttct gctatgtggc    3720 gcggtattat cccgtgttga cgccgggcaa gagcaactcg tcgccgcat acactattct    3780 cagaatgact tggttgagta ctcaccagtc acagaaaagc atcttacgga tggcatgaca    3840
gtaagagaat tatgcagtgc tgccataacc atgagtgata acactgcggc caacttactt    3900
ctgacaacga tcggaggacc gaaggagcta accgcttttt tgcacaacat ggggatcat     3960 gtaactcgcc ttgatcgttg ggaaccggag ctgaatgaag ccataccaaa cgacgagcgt    4020
gacaccacga tgcctgtagc aatggcaaca acgttgcgca aactattaac tggcgaacta    4080
cttactctag cttcccggca acaattaata gactggatgg aggcggataa agttgcagga    4140
ccacttctgc gctcggccct tccggctggc tggtttattg ctgataaatc tggagccggt    4200
gagcgtgggt ctcgcggtat cattgcagca ctggggccag atggtaagcc ctcccgtatc    4260
gtagttatct acacgacggg gagtcaggca actatggatg aacgaaatag acagatcgct    4320
gagataggtg cctcactgat taagcattgg taactgtcag accaagttta ctcatatata    4380
ctttagattg atttacgcgc cctgtagcgg cgcattaagc gcggcgggtg tggtggttac    4440
gcgcagcgtg accgctacac ttgccagcgc cctagcgccc gctcctttcg ctttcttccc    4500
ttcctttctc gccacgttcg ccggctttcc ccgtcaagct ctaaatcggg ggctcccttt    4560
agggttccga tttagtgctt tacggcacct cgaccccaaa aaacttgatt tgggtgatgg    4620
ttcacgtagt gggccatcgc cctgatagac ggtttttcgc cctttgacgt tggagtccac    4680
gttctttaat agtggactct tgttccaaac ttgaacaaca ctcaacccta tctcgggcta    4740
ttcttttgat ttataaggga ttttgccgat ttcggcctat tggttaaaaa atgagctgat    4800
ttaacaaaaa tttaacgcga attttaacaa aatattaacg tttacaattt aaaaggatct    4860
aggtgaagat ccttttttgat aatctcatga ccaaaatccc ttaacgtgag ttttcgttcc    4920
actgagcgtc agaccccgta gaaaagatca aaggatcttc ttgagatcct ttttttctgc    4980
gcgtaatctg ctgcttgcaa acaaaaaaac caccgctacc agcggtggtt tgtttgccgg    5040
atcaagagct accaactctt tttccgaagg taactggctt cagcagagcg cagataccaa    5100
atactgtcct tctagtgtag ccgtagttag gccaccactt caagaactct gtagcaccgc    5160
ctacatacct cgctctgcta atcctgttac cagtggctgc tgccagtggc gataagtcgt    5220
gtcttaccgg gttggactca agacgatagt taccggataa ggcgcagcgg tcgggctgaa    5280 cgggggggttc gtgcacacag cccagcttgg agcgaacgac ctacaccgaa ctgagatacc    5340
tacagcgtga gctatgagaa agcgccacgc ttcccgaagg gagaaaggcg gacaggtatc    5400
cggtaagcgg cagggtcgga acaggagagc gcacgaggga gcttccaggg ggaaacgcct    5460
ggtatcttta tagtcctgtc gggtttcgcc acctctgact tgagcgtcga ttttttgtgat    5520 gctcgtcagg ggggcggagc ctatggaaaa acgccagcaa cgcggccttt ttacggttcc    5580
```

-continued

```
tggccttttg ctggccttttt gctcacatgt tctttcctgc gttatcccct gattctgtgg    5640
ataaccgtat taccgccttt gagtgagctg ataccgctcg ccgcagccga acgaccgagc    5700
gcagcgagtc agtgagcgag gaagcggaag agcgcctgat gcggtatttt ctccttacgc    5760
atctgtgcgg tatttcacac cgcatagggt catggctgcg ccccgacacc cgccaacacc    5820
cgctgacgcg ccctgacggg cttgtctgct cccggcatcc gcttacagac aagctgtgac    5880
cgtctccggg agctgcatgt gtcagaggtt ttcaccgtca tcaccgaaac gcgcgaggca    5940
gcaaggagat ggcgcccaac agtccccggg ccacggggcc tgccaccata cccacgccga    6000
aacaagcgct catgagcccg aagtggcgag cccgatcttc cccatcggtg atgtcggcga    6060
tataggcgcc agcaaccgca cctgtggcgc cggtgatgcc ggccacgatg cgtccggcgt    6120
agaggatctg ctcatgtttg acagcttatc                                     6150
```

<210> SEQ ID NO 2
<211> LENGTH: 843
<212> TYPE: DNA
<213> ORGANISM: Artificial Sequence
<220> FEATURE:
<221> NAME/KEY: misc_feature
<222> LOCATION: (1)..(843)
<223> OTHER INFORMATION: t-recE on plasmid pBAD24-recET at 1320-2162
<221> NAME/KEY: CDS
<222> LOCATION: (1)..(843)
<223> OTHER INFORMATION: t-recE

<400> SEQUENCE: 2

```
atg gat ccc gta atc gta gaa gac ata gag cca ggt att tat tac gga        48
Met Asp Pro Val Ile Val Glu Asp Ile Glu Pro Gly Ile Tyr Tyr Gly
  1               5                  10                  15 att tcg aat gag aat tac cac gcg ggt ccc ggt atc agt aag tct cag        96
Ile Ser Asn Glu Asn Tyr His Ala Gly Pro Gly Ile Ser Lys Ser Gln
             20                  25                  30 ctc gat gac att gct gat act ccg gca cta tat ttg tgg cgt aaa aat       144
Leu Asp Asp Ile Ala Asp Thr Pro Ala Leu Tyr Leu Trp Arg Lys Asn
         35                  40                  45 gcc ccc gtg gac acc aca aag aca aaa acg ctc gat tta gga act gct       192
Ala Pro Val Asp Thr Thr Lys Thr Lys Thr Leu Asp Leu Gly Thr Ala
     50                  55                  60 ttc cac tgc cgg gta ctt gaa ccg gaa gaa ttc agt aac cgc ttt atc       240
Phe His Cys Arg Val Leu Glu Pro Glu Glu Phe Ser Asn Arg Phe Ile
 65                  70                  75                  80 gta gca cct gaa ttt aac cgc cgt aca aac gcc gga aaa gaa gaa gag       288
Val Ala Pro Glu Phe Asn Arg Arg Thr Asn Ala Gly Lys Glu Glu Glu
                 85                  90                  95 aaa gcg ttt ctg atg gaa tgc gca agc aca gga aaa acg gtt atc act       336
Lys Ala Phe Leu Met Glu Cys Ala Ser Thr Gly Lys Thr Val Ile Thr
            100                 105                 110 gcg gaa gaa ggc cgg aaa att gaa ctc atg tat caa agc gtt atg gct       384
Ala Glu Glu Gly Arg Lys Ile Glu Leu Met Tyr Gln Ser Val Met Ala
        115                 120                 125 ttg ccg ctg ggg caa tgg ctt gtt gaa agc gcc gga cac gct gaa tca       432
Leu Pro Leu Gly Gln Trp Leu Val Glu Ser Ala Gly His Ala Glu Ser
    130                 135                 140 tca att tac tgg gaa gat cct gaa aca gga att ttg tgt cgg tgc cgt       480
Ser Ile Tyr Trp Glu Asp Pro Glu Thr Gly Ile Leu Cys Arg Cys Arg
145                 150                 155                 160 ccg gac aaa att atc cct gaa ttt cac tgg atc atg gac gtg aaa act       528
Pro Asp Lys Ile Ile Pro Glu Phe His Trp Ile Met Asp Val Lys Thr
                165                 170                 175
```

```
                                                                         -continued acg gcg gat att caa cga ttc aaa acc gct tat tac gac tac cgc tat         576
Thr Ala Asp Ile Gln Arg Phe Lys Thr Ala Tyr Tyr Asp Tyr Arg Tyr
        180                 185                 190 cac gtt cag gat gca ttc tac agt gac ggt tat gaa gca cag ttt gga         624
His Val Gln Asp Ala Phe Tyr Ser Asp Gly Tyr Glu Ala Gln Phe Gly
            195                 200                 205 gtg cag cca act ttc gtt ttt ctg gtt gcc agc aca act att gaa tgc         672
Val Gln Pro Thr Phe Val Phe Leu Val Ala Ser Thr Thr Ile Glu Cys
    210                 215                 220 gga cgt tat ccg gtt gaa att ttc atg atg ggc gaa gaa gca aaa ctg         720
Gly Arg Tyr Pro Val Glu Ile Phe Met Met Gly Glu Glu Ala Lys Leu
225                 230                 235                 240 gca ggt caa cag gaa tat cac cgc aat ctg cga acc ctg tct gac tgc         768
Ala Gly Gln Gln Glu Tyr His Arg Asn Leu Arg Thr Leu Ser Asp Cys
                245                 250                 255 ctg aat acc gat gaa tgg cca gct att aag aca tta tca ctg ccc cgc         816
Leu Asn Thr Asp Glu Trp Pro Ala Ile Lys Thr Leu Ser Leu Pro Arg
            260                 265                 270 tgg gct aag gaa tat gca aat gac taa                                     843
Trp Ala Lys Glu Tyr Ala Asn Asp  *
        275                 280

<210> SEQ ID NO 3
<211> LENGTH: 280
<212> TYPE: PRT
<213> ORGANISM: Artificial Sequence
<220> FEATURE:
<221> NAME/KEY: misc_feature
<222> LOCATION: (1)..(280)
<223> OTHER INFORMATION: t-recE on plasmid pBAD24-recET at 1320-2162

<400> SEQUENCE: 3

Met Asp Pro Val Ile Val Glu Asp Ile Glu Pro Gly Ile Tyr Tyr Gly
  1               5                  10                  15

Ile Ser Asn Glu Asn Tyr His Ala Gly Pro Gly Ile Ser Lys Ser Gln
             20                  25                  30

Leu Asp Asp Ile Ala Asp Thr Pro Ala Leu Tyr Leu Trp Arg Lys Asn
         35                  40                  45

Ala Pro Val Asp Thr Thr Lys Thr Lys Thr Leu Asp Leu Gly Thr Ala
     50                  55                  60

Phe His Cys Arg Val Leu Glu Pro Glu Glu Phe Ser Asn Arg Phe Ile
 65                  70                  75                  80

Val Ala Pro Glu Phe Asn Arg Arg Thr Asn Ala Gly Lys Glu Glu
                 85                  90                  95

Lys Ala Phe Leu Met Glu Cys Ala Ser Thr Gly Lys Thr Val Ile Thr
            100                 105                 110

Ala Glu Glu Gly Arg Lys Ile Glu Leu Met Tyr Gln Ser Val Met Ala
        115                 120                 125

Leu Pro Leu Gly Gln Trp Leu Val Glu Ser Ala Gly His Ala Glu Ser
    130                 135                 140

Ser Ile Tyr Trp Glu Asp Pro Glu Thr Gly Ile Leu Cys Arg Cys Arg
145                 150                 155                 160

Pro Asp Lys Ile Ile Pro Glu Phe His Trp Ile Met Asp Val Lys Thr
                165                 170                 175

Thr Ala Asp Ile Gln Arg Phe Lys Thr Ala Tyr Tyr Asp Tyr Arg Tyr
            180                 185                 190

His Val Gln Asp Ala Phe Tyr Ser Asp Gly Tyr Glu Ala Gln Phe Gly
        195                 200                 205
```

```
Val Gln Pro Thr Phe Val Phe Leu Val Ala Ser Thr Thr Ile Glu Cys
    210                 215                 220
Gly Arg Tyr Pro Val Glu Ile Phe Met Met Gly Glu Ala Lys Leu
225                 230                 235                 240
Ala Gly Gln Gln Glu Tyr His Arg Asn Leu Arg Thr Leu Ser Asp Cys
                245                 250                 255
Leu Asn Thr Asp Glu Trp Pro Ala Ile Lys Thr Leu Ser Leu Pro Arg
            260                 265                 270
Trp Ala Lys Glu Tyr Ala Asn Asp
        275                 280

<210> SEQ ID NO 4
<211> LENGTH: 810
<212> TYPE: DNA
<213> ORGANISM: Artificial Sequence
<220> FEATURE:
<221> NAME/KEY: misc_feature
<222> LOCATION: (1)..(810)
<223> OTHER INFORMATION: recT on plasmid pBAD24-recET at 2155-2972
<221> NAME/KEY: CDS
<222> LOCATION: (1)..(810)
<223> OTHER INFORMATION: recT

<400> SEQUENCE: 4 atg act aag caa cca cca atc gca aaa gcc gat ctg caa aaa act cag      48
Met Thr Lys Gln Pro Pro Ile Ala Lys Ala Asp Leu Gln Lys Thr Gln
            285                 290                 295 gga aac cgt gca cca gca gca gtt aaa aat agc gac gtg att agt ttt      96
Gly Asn Arg Ala Pro Ala Ala Val Lys Asn Ser Asp Val Ile Ser Phe
        300                 305                 310 att aac cag cca tca atg aaa gag caa ctg gca gca gct ctt cca cgc     144
Ile Asn Gln Pro Ser Met Lys Glu Gln Leu Ala Ala Ala Leu Pro Arg
    315                 320                 325 cat atg acg gct gaa cgt atg atc cgt atc gcc acc aca gaa att cgt     192
His Met Thr Ala Glu Arg Met Ile Arg Ile Ala Thr Thr Glu Ile Arg
330                 335                 340                 345 aaa gtt ccg gcg tta gga aac tgt gac act atg agt ttt gtc agt gcg     240
Lys Val Pro Ala Leu Gly Asn Cys Asp Thr Met Ser Phe Val Ser Ala
                350                 355                 360 atc gta cag tgt tca cag ctc gga ctt gag cca ggt agc gcc ctc ggt     288
Ile Val Gln Cys Ser Gln Leu Gly Leu Glu Pro Gly Ser Ala Leu Gly
            365                 370                 375 cat gca tat tta ctg cct ttt ggt aat aaa aac gaa aag agc ggt aaa     336
His Ala Tyr Leu Leu Pro Phe Gly Asn Lys Asn Glu Lys Ser Gly Lys
        380                 385                 390 aag aac gtt cag cta atc att ggc tat cgc ggc atg att gat ctg gct     384
Lys Asn Val Gln Leu Ile Ile Gly Tyr Arg Gly Met Ile Asp Leu Ala
    395                 400                 405 cgc cgt tct ggt caa atc gcc agc ctg tca gcc cgt gtt gtc cgt gaa     432
Arg Arg Ser Gly Gln Ile Ala Ser Leu Ser Ala Arg Val Val Arg Glu
410                 415                 420                 425 ggt gac gag ttt agc ttc gaa ttt ggc ctt gat gaa aag tta ata cac     480
Gly Asp Glu Phe Ser Phe Glu Phe Gly Leu Asp Glu Lys Leu Ile His
                430                 435                 440 cgc ccg gga gaa aac gaa gat gcc ccg gtt acc cac gtc tat gct gtc     528
Arg Pro Gly Glu Asn Glu Asp Ala Pro Val Thr His Val Tyr Ala Val
            445                 450                 455 gca aga ctg aaa gac gga ggt act cag ttt gaa gtt atg acg cgc aaa     576
Ala Arg Leu Lys Asp Gly Gly Thr Gln Phe Glu Val Met Thr Arg Lys
        460                 465                 470 cag att gag ctg gtg cgc agc ctg agt aaa gct ggt aat aac ggg ccg     624
```

```
Gln Ile Glu Leu Val Arg Ser Leu Ser Lys Ala Gly Asn Asn Gly Pro
            475                 480                 485 tgg gta act cac tgg gaa gaa atg gca aag aaa acg gct att cgt cgc      672
Trp Val Thr His Trp Glu Glu Met Ala Lys Lys Thr Ala Ile Arg Arg
490                 495                 500                 505 ctg ttc aaa tat ttg ccc gta tca att gag atc cag cgt gca gta tca      720
Leu Phe Lys Tyr Leu Pro Val Ser Ile Glu Ile Gln Arg Ala Val Ser
                    510                 515                 520 atg gat gaa aag gaa cca ctg aca atc gat cct gca gat tcc tct gta      768
Met Asp Glu Lys Glu Pro Leu Thr Ile Asp Pro Ala Asp Ser Ser Val
                525                 530                 535 tta acc ggg gaa tac agt gta atc gat aat tca gag gaa tag              810
Leu Thr Gly Glu Tyr Ser Val Ile Asp Asn Ser Glu Glu *
            540                 545                 550

<210> SEQ ID NO 5
<211> LENGTH: 269
<212> TYPE: PRT
<213> ORGANISM: Artificial Sequence
<220> FEATURE:
<221> NAME/KEY: misc_feature
<222> LOCATION: (1)..(269)
<223> OTHER INFORMATION: recT on plasmid pBAD24-recET at 2155-2972

<400> SEQUENCE: 5

Met Thr Lys Gln Pro Pro Ile Ala Lys Ala Asp Leu Gln Lys Thr Gln
  1               5                  10                  15

Gly Asn Arg Ala Pro Ala Ala Val Lys Asn Ser Asp Val Ile Ser Phe
             20                  25                  30

Ile Asn Gln Pro Ser Met Lys Glu Gln Leu Ala Ala Ala Leu Pro Arg
         35                  40                  45

His Met Thr Ala Glu Arg Met Ile Arg Ile Ala Thr Thr Glu Ile Arg
     50                  55                  60

Lys Val Pro Ala Leu Gly Asn Cys Asp Thr Met Ser Phe Val Ser Ala
 65                  70                  75                  80

Ile Val Gln Cys Ser Gln Leu Gly Leu Glu Pro Gly Ser Ala Leu Gly
                 85                  90                  95

His Ala Tyr Leu Leu Pro Phe Gly Asn Lys Asn Glu Lys Ser Gly Lys
            100                 105                 110

Lys Asn Val Gln Leu Ile Ile Gly Tyr Arg Gly Met Ile Asp Leu Ala
        115                 120                 125

Arg Arg Ser Gly Gln Ile Ala Ser Leu Ser Ala Arg Val Val Arg Glu
    130                 135                 140

Gly Asp Glu Phe Ser Phe Glu Phe Gly Leu Asp Glu Lys Leu Ile His
145                 150                 155                 160

Arg Pro Gly Glu Asn Glu Asp Ala Pro Val Thr His Val Tyr Ala Val
                165                 170                 175

Ala Arg Leu Lys Asp Gly Gly Thr Gln Phe Glu Val Met Thr Arg Lys
            180                 185                 190

Gln Ile Glu Leu Val Arg Ser Leu Ser Lys Ala Gly Asn Asn Gly Pro
        195                 200                 205

Trp Val Thr His Trp Glu Glu Met Ala Lys Lys Thr Ala Ile Arg Arg
    210                 215                 220

Leu Phe Lys Tyr Leu Pro Val Ser Ile Glu Ile Gln Arg Ala Val Ser
225                 230                 235                 240

Met Asp Glu Lys Glu Pro Leu Thr Ile Asp Pro Ala Asp Ser Ser Val
                245                 250                 255
```

Leu Thr Gly Glu Tyr Ser Val Ile Asp Asn Ser Glu Glu
    260        265

<210> SEQ ID NO 6
<211> LENGTH: 876
<212> TYPE: DNA
<213> ORGANISM: Artificial Sequence
<220> FEATURE:
<221> NAME/KEY: misc_feature
<222> LOCATION: (1)..(876)
<223> OTHER INFORMATION: araC on plasmid pBAD24-recET at 974-996
<221> NAME/KEY: CDS
<222> LOCATION: (1)..(876)
<223> OTHER INFORMATION: araC

<400> SEQUENCE: 6

```
tgacaacttg acggctacat cattcacttt ttcttcacaa ccggcacgga actcgctcgg      60
gctggcccg gtgcattttt taaatacccg cgagaaatag agttgatcgt caaaaccaac     120
attgcgaccg acggtggcga taggcatccg ggtggtgctc aaaagcagct tcgcctggct     180
gatacgttgg tcctcgcgcc agcttaagac gctaatccct aactgctggc ggaaaagatg     240
tgacagacgc gacggcgaca agcaaacatg ctgtgcgacg ctggcgatat caaaattgct     300
gtctgccagg tgatcgctga tgtactgaca agcctcgcgt acccgattat ccatcggtgg     360
atggagcgac tcgttaatcg cttccatgcg ccgcagtaac aattgctcaa gcagatttat     420
cgccagcagc tccgaatagc gcccttcccc ttgcccggcg ttaatgattt gcccaaacag     480
gtcgctgaaa tgcggctggt gcgcttcatc cgggcgaaaa accccgtat tggcaaatat     540
tgacggccag ttaagccatt catgccagta ggcgcgcgga cgaaagtaaa cccactggtg     600
ataccattcg cgagcctccg gatgacgacc gtagtgatga atctctcctg gcgggaacag     660
caaaatatca cccggtcggc aaacaaattc tcgtccctga tttttcacca ccccctgacc     720
gcgaatggtg agattgagaa tataaccttt cattcccagc ggtcggtcga taaaaaaatc     780
gagataaccg ttggcctcaa tcggcgttaa acccgccacc agatgggcat taaacgagta     840
tcccggcagc aggggatcat tttgcgcttc agccat                              876
```

<210> SEQ ID NO 7
<211> LENGTH: 292
<212> TYPE: PRT
<213> ORGANISM: Artificial Sequence
<220> FEATURE:
<221> NAME/KEY: misc_feature
<222> LOCATION: (1)..(292)
<223> OTHER INFORMATION: araC on plasmid pBAD24-recET at 974-996

<400> SEQUENCE: 7

Met Ala Glu Ala Gln Asn Asp Pro Leu Leu Pro Gly Tyr Ser Phe Asn
1     5       10       15

Ala His Leu Val Ala Gly Leu Thr Pro Ile Glu Ala Asn Gly Tyr Leu
      20       25       30

Asp Phe Phe Ile Asp Arg Pro Leu Gly Met Lys Gly Tyr Ile Leu Asn
    35        40       45

Leu Thr Ile Arg Gly Gln Gly Val Val Lys Asn Gln Gly Arg Glu Phe
  50        55        60

Val Cys Arg Pro Gly Asp Ile Leu Leu Phe Pro Pro Gly Glu Ile His
65         70        75        80

His Tyr Gly Arg His Pro Glu Ala Arg Glu Trp Tyr His Gln Trp Val
       85        90       95

Tyr Phe Arg Pro Arg Ala Tyr Trp His Glu Trp Leu Asn Trp Pro Ser

-continued

```
                    100                 105                 110
Ile Phe Ala Asn Thr Gly Phe Arg Pro Asp Glu Ala His Gln Pro
            115                 120                 125
His Phe Ser Asp Leu Phe Gly Gln Ile Ile Asn Ala Gly Gln Gly Glu
        130                 135                 140
Gly Arg Tyr Ser Glu Leu Leu Ala Ile Asn Leu Leu Glu Gln Leu Leu
145                 150                 155                 160
Leu Arg Arg Met Glu Ala Ile Asn Glu Ser Leu His Pro Pro Met Asp
                165                 170                 175
Asn Arg Val Arg Glu Ala Cys Gln Tyr Ile Ser Asp His Leu Ala Asp
                180                 185                 190
Ser Asn Phe Asp Ile Ala Ser Val Ala Gln His Val Cys Leu Ser Pro
            195                 200                 205
Ser Arg Leu Ser His Leu Phe Arg Gln Gln Leu Gly Ile Ser Val Leu
        210                 215                 220
Ser Trp Arg Glu Asp Gln Arg Ile Ser Gln Ala Lys Leu Leu Leu Ser
225                 230                 235                 240
Thr Thr Arg Met Pro Ile Ala Thr Val Gly Arg Asn Val Gly Phe Asp
                245                 250                 255
Asp Gln Leu Tyr Phe Ser Arg Val Phe Lys Lys Cys Thr Gly Ala Ser
                260                 265                 270
Pro Ser Glu Phe Arg Ala Gly Cys Glu Glu Lys Val Asn Asp Val Ala
            275                 280                 285
Val Lys Leu Ser
        290

<210> SEQ ID NO 8
<211> LENGTH: 861
<212> TYPE: DNA
<213> ORGANISM: Artificial Sequence
<220> FEATURE:
<221> NAME/KEY: misc_feature
<222> LOCATION: (1)..(861)
<223> OTHER INFORMATION: bla gene on plasmid pBAD24-recET at 3493-4353
<221> NAME/KEY: CDS
<222> LOCATION: (1)..(861)
<223> OTHER INFORMATION: bla

<400> SEQUENCE: 8 atg agt att caa cat ttc cgt gtc gcc ctt att ccc ttt ttt gcg gca      48
Met Ser Ile Gln His Phe Arg Val Ala Leu Ile Pro Phe Phe Ala Ala
            295                 300                 305 ttt tgc ctt cct gtt ttt gct cac cca gaa acg ctg gtg aaa gta aaa     96
Phe Cys Leu Pro Val Phe Ala His Pro Glu Thr Leu Val Lys Val Lys
        310                 315                 320 gat gct gaa gat cag ttg ggt gca cga gtg ggt tac atc gaa ctg gat    144
Asp Ala Glu Asp Gln Leu Gly Ala Arg Val Gly Tyr Ile Glu Leu Asp
325                 330                 335                 340 ctc aac agc ggt aag atc ctt gag agt ttt cgc ccc gaa gaa cgt ttt    192
Leu Asn Ser Gly Lys Ile Leu Glu Ser Phe Arg Pro Glu Glu Arg Phe
                345                 350                 355 cca atg atg agc act ttt aaa gtt ctg cta tgt ggc gcg gta tta tcc    240
Pro Met Met Ser Thr Phe Lys Val Leu Leu Cys Gly Ala Val Leu Ser
            360                 365                 370 cgt gtt gac gcc ggg caa gag caa ctc ggt cgc cgc ata cac tat tct    288
Arg Val Asp Ala Gly Gln Glu Gln Leu Gly Arg Arg Ile His Tyr Ser
        375                 380                 385 cag aat gac ttg gtt gag tac tca cca gtc aca gaa aag cat ctt acg    336
Gln Asn Asp Leu Val Glu Tyr Ser Pro Val Thr Glu Lys His Leu Thr
```

-continued

```
         390                 395                 400
gat ggc atg aca gta aga gaa tta tgc agt gct gcc ata acc atg agt     384
Asp Gly Met Thr Val Arg Glu Leu Cys Ser Ala Ala Ile Thr Met Ser
405                 410                 415                 420 gat aac act gcg gcc aac tta ctt ctg aca acg atc gga gga ccg aag     432
Asp Asn Thr Ala Ala Asn Leu Leu Leu Thr Thr Ile Gly Gly Pro Lys
                425                 430                 435 gag cta acc gct ttt ttg cac aac atg ggg gat cat gta act cgc ctt     480
Glu Leu Thr Ala Phe Leu His Asn Met Gly Asp His Val Thr Arg Leu
            440                 445                 450 gat cgt tgg gaa ccg gag ctg aat gaa gcc ata cca aac gac gag cgt     528
Asp Arg Trp Glu Pro Glu Leu Asn Glu Ala Ile Pro Asn Asp Glu Arg
        455                 460                 465 gac acc acg atg cct gta gca atg gca aca acg ttg cgc aaa cta tta     576
Asp Thr Thr Met Pro Val Ala Met Ala Thr Thr Leu Arg Lys Leu Leu
    470                 475                 480 act ggc gaa cta ctt act cta gct tcc cgg caa caa tta ata gac tgg     624
Thr Gly Glu Leu Leu Thr Leu Ala Ser Arg Gln Gln Leu Ile Asp Trp
485                 490                 495                 500 atg gag gcg gat aaa gtt gca gga cca ctt ctg cgc tcg gcc ctt ccg     672
Met Glu Ala Asp Lys Val Ala Gly Pro Leu Leu Arg Ser Ala Leu Pro
                505                 510                 515 gct ggc tgg ttt att gct gat aaa tct gga gcc ggt gag cgt ggg tct     720
Ala Gly Trp Phe Ile Ala Asp Lys Ser Gly Ala Gly Glu Arg Gly Ser
            520                 525                 530 cgc ggt atc att gca gca ctg ggg cca gat ggt aag ccc tcc cgt atc     768
Arg Gly Ile Ile Ala Ala Leu Gly Pro Asp Gly Lys Pro Ser Arg Ile
        535                 540                 545 gta gtt atc tac acg acg ggg agt cag gca act atg gat gaa cga aat     816
Val Val Ile Tyr Thr Thr Gly Ser Gln Ala Thr Met Asp Glu Arg Asn
    550                 555                 560 aga cag atc gct gag ata ggt gcc tca ctg att aag cat tgg taa         861
Arg Gln Ile Ala Glu Ile Gly Ala Ser Leu Ile Lys His Trp *
565                 570                 575
```

<210> SEQ ID NO 9
<211> LENGTH: 286
<212> TYPE: PRT
<213> ORGANISM: Artificial Sequence
<220> FEATURE:
<221> NAME/KEY: DOMAIN
<222> LOCATION: (1)..(286)
<223> OTHER INFORMATION: bla gene on plasmid pBAD24-recET at 3493-4353

<400> SEQUENCE: 9

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110
```

```
Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
        275                 280                 285

<210> SEQ ID NO 10
<211> LENGTH: 7195
<212> TYPE: DNA
<213> ORGANISM: Artificial Sequence
<220> FEATURE:
<221> NAME/KEY: misc_feature
<222> LOCATION: (1)..(7195)
<223> OTHER INFORMATION: plasmid pBAD-ET-gamma
<221> NAME/KEY: CDS
<222> LOCATION: (1)..(7195)
<223> OTHER INFORMATION: red gamma

<400> SEQUENCE: 10
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcattttta      180 aatacccgcg agaaatagag ttgatcgtca aaccaacat tgcgaccgac ggtggcgata     240
ggcatccggg tggtgctcaa aagcagcttc gcctggctga tacgttggtc ctcgcgccag    300
cttaagacgc taatccctaa ctgctggcgg aaaagatgtg acagacgcga cggcgacaag    360
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttcccctt gcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag ggatcatttt    960
```

```
tgcgcttcag ccatactttt catactcccg ccattcagag aagaaaccaa ttgtccatat   1020
tgcatcagac attgccgtca ctgcgtcttt tactggctct tctcgctaac caaaccggta   1080
accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgcttttta   1260
tcgcaactct ctactgtttc tccatacccg ttttttgggg ctagcaggag gaattcacca   1320
tggatcccgt aatcgtagaa gacatagagc caggtattta ttacgaatt tcgaatgaga   1380 attaccacgc gggtcccggt atcagtaagt ctcagctcga tgacattgct gatactccgg   1440
cactatattt gtggcgtaaa aatgcccccg tggacaccac aaagacaaaa acgctcgatt   1500
taggaactgc tttccactgc cgggtacttg aaccggaaga attcagtaac cgctttatcg   1560
tagcacctga atttaaccgc cgtacaaacg ccggaaaaga agaagagaaa gcgtttctga   1620
tggaatgcgc aagcacagga aaaacggtta tcactgcgga agaaggccgg aaaattgaac   1680
tcatgtatca aagcgttatg gctttgccgc tggggcaatg gcttgttgaa agcgccggac   1740
acgctgaatc atcaatttac tgggaagatc ctgaaacagg aattttgtgt cggtgccgtc   1800
cggacaaaat tatccctgaa tttcactgga tcatggacgt gaaaactacg gcggatattc   1860
aacgattcaa aaccgcttat tacgactacc gctatcacgt tcaggatgca ttctacagtg   1920
acggttatga agcacagttt ggagtgcagc caactttcgt ttttctggtt gccagcacaa   1980
ctattgaatg cggacgttat ccggttgaaa ttttcatgat gggcgaagaa gcaaaactgg   2040
caggtcaaca ggaatatcac cgcaatctgc gaaccctgtc tgactgcctg aataccgatg   2100
aatggccagc tattaagaca ttatcactgc cccgctgggc taaggaatat gcaaatgact   2160
agatctcgag gtacccgagc acgtgttgac aattaatcat cggcatagta tatcggcata   2220
gtataatacg acaaggtgag gaactaaacc atggctaagc aaccaccaat cgcaaaagcc   2280
gatctgcaaa aaactcaggg aaaccgtgca ccagcagcag ttaaaaatag cgacgtgatt   2340
agttttatta accagccatc aatgaaagag caactggcag cagctcttcc acgccatatg   2400
acggctgaac gtatgatccg tatcgccacc acagaaattc gtaaagttcc ggcgttagga   2460
aactgtgaca ctatgagttt tgtcagtgcg atcgtacagt gttcacagct cggacttgag   2520
ccaggtagcg ccctcggtca tgcatattta ctgcctttg gtaataaaaa cgaaaagagc   2580
ggtaaaaaga acgttcagct aatcattggc tatcgcggca tgattgatct ggctcgccgt   2640
tctggtcaaa tcgccagcct gtcagcccgt gttgtccgtg aaggtgacga gtttagcttc   2700
gaatttggcc ttgatgaaaa gttaatacac cgcccgggag aaaacgaaga tgccccggtt   2760
acccacgtct atgctgtcgc aagactgaaa gacggaggta ctcagtttga agttatgacg   2820
cgcaaacaga ttgagctggt gcgcagcctg agtaaagctg gtaataacgg ccgtgggta   2880 actcactggg aagaaatggc aaagaaaacg gctattcgtc gcctgttcaa atatttgccc   2940
gtatcaattg agatccagcg tgcagtatca atggatgaaa aggaaccact gacaatcgat   3000
cctgcagatt cctctgtatt aaccggggaa tacagtgtaa tcgataattc agaggaatag   3060
atctaagctt cctgctgaac atcaaaggca agaaacatc tgttgtcaaa gacagcatcc   3120
ttgaacaagg acaattaaca gttaacaaat aaaaacgcaa aagaaaatgc cgatatccta   3180
ttggcatttt ctttttattc ttatcaacat aaaggtgaat cccataccte gagcttcacg   3240 ctgccgcaag cactcagggc gcaagggctg ctaaaaggaa gcggaacacg tagaaagcca   3300
```

-continued

```
gtccgcagaa acggtgctga ccccggatga atgtcagcta ctgggctatc tggacaaggg      3360
aaaacgcaag cgcaaagaga aagcaggtag cttgcagtgg gcttacatgg cgatagctag      3420
actgggcggt tttatggaca gcaagcgaac cggaattgcc agctgggcg ccctctggta       3480 aggttgggaa gccctgcaaa gtaaactgga tggctttctt gccgccaagg atctgatggc      3540 gcagggatc aagatctgat caagagacag gatgaggatc gtttcgcatg gatattaata      3600
ctgaaactga gatcaagcaa agcattcac taaccccctt tcctgttttc ctaatcagcc      3660
cggcatttcg cggcgatat tttcacagct atttcaggag ttcagccatg aacgcttatt      3720
acattcagga tcgtcttgag gctcagagct gggcgcgtca ctaccagcag ctcgcccgtg      3780
aagagaaaga ggcagaactg gcagacgaca tggaaaaagg cctgccccag cacctgtttg      3840
aatcgctatg catcgatcat ttgcaacgcc acggggccag caaaaaatcc attacccgtg      3900
cgtttgatga cgatgttgag tttcaggagc gcatggcaga acacatccgg tacatggttg      3960
aaaccattgc tcaccaccag gttgatattg attcagaggt ataaaacgag tagaagcttg      4020
gctgttttgg cggatgagag aagattttca gcctgataca gattaaatca gaacgcagaa      4080
gcggtctgat aaaacagaat ttgcctggcg gcagtagcgc ggtggtccca cctgacccca      4140
tgccgaactc agaagtgaaa cgccgtagcc ccgatggtag tgtggggtct ccccatgcga      4200
gagtagggaa ctgccaggca tcaaataaaa cgaaaggctc agtcgaaaga ctgggccttt      4260
cgttttatct gttgtttgtc ggtgaacgct ctcctgagta ggacaaatcc gccgggagcg      4320
gatttgaacg ttgcgaagca acggcccgga gggtggcggg caggacgccc gccataaact      4380
gccaggcatc aaattaagca gaaggccatc ctgacggatg ccttttttgc gtttctacaa      4440
actcttttgt ttattttctc aaatacattc aaatatgtat ccgctcatga gacaataacc      4500
ctgataaatg cttcaataat attgaaaaag gaagagtatg agtattcaac atttccgtgt      4560
cgcccttatt ccctttttg cggcattttg ccttcctgtt tttgctcacc cagaaacgct      4620
ggtgaaagta aaagatgctg aagatcagtt gggtgcacga gtgggttaca tcgaactgga      4680
tctcaacagc ggtaagatcc ttgagagttt tcgccccgaa gaacgttttc caatgatgag      4740
cacttttaaa gttctgctat gtggcgcggt attatcccgt gttgacgccg ggcaagagca      4800
actcggtcgc cgcatacact attctcagaa tgacttggtt gagtactcac cagtcacaga      4860
aaagcatctt acggatggca tgacagtaag agaattatgc agtgctgcca taaccatgag      4920
tgataacact gcggccaact tacttctgac aacgatcgga ggaccgaagg agctaaccgc      4980
ttttttgcac aacatggggg atcatgtaac tcgccttgat cgttgggaac cggagctgaa      5040
tgaagccata ccaaacgacg agcgtgacac cacgatgcct gtagcaatgg caacaacgtt      5100
gcgcaaacta ttaactggcg aactacttac tctagcttcc cggcaacaat taatagactg      5160
gatggaggcg gataaagttg caggaccact tctgcgctcg gcccttccgg ctggctggtt      5220
tattgctgat aaatctggag ccggtgagcg tgggtctcgc ggtatcattg cagcactggg      5280
gccagatggt aagccctccc gtatcgtagt tatctacacg acgggagtc aggcaactat       5340 ggatgaacga aatagacaga tcgctgagat aggtgcctca ctgattaagc attggtaact      5400
gtcagaccaa gtttactcat atatacttta gattgattta cgcgcccgt agcggcgcat      5460 taagcgcggc gggtgtggtg gttacgcgca gcgtgaccgc tacacttgcc agcgccctag      5520
cgcccgctcc tttcgctttc ttcccttcct ttctcgccac gttcgccggc tttccccgtc      5580
aagctctaaa tcggggggctc ctttagggt tccgatttag tgctttacgg cacctcgacc      5640
ccaaaaaact tgatttgggt gatggttcac gtagtgggcc atcgccctga tagacggttt      5700
```

```
ttcgcccttt gacgttggag tccacgttct ttaatagtgg actcttgttc caaacttgaa    5760
caacactcaa ccctatctcg ggctattctt ttgatttata agggattttg ccgatttcgg    5820
cctattggtt aaaaaatgag ctgatttaac aaaaatttaa cgcgaatttt aacaaaatat    5880
taacgtttac aatttaaaag gatctaggtg aagatccttt ttgataatct catgaccaaa    5940
atcccttaac gtgagttttc gttccactga gcgtcagacc ccgtagaaaa gatcaaagga    6000
tcttcttgag atcctttttt tctgcgcgta atctgctgct tgcaaacaaa aaaaccaccg    6060
ctaccagcgg tggtttgttt gccggatcaa gagctaccaa ctcttttttcc gaaggtaact    6120 ggcttcagca gagcgcagat accaaatact gtccttctag tgtagccgta gttaggccac    6180
cacttcaaga actctgtagc accgcctaca tacctcgctc tgctaatcct gttaccagtg    6240
gctgctgcca gtggcgataa gtcgtgtctt accgggttgg actcaagacg atagttaccg    6300
gataaggcgc agcggtcggg ctgaacgggg gttcgtgca cacagcccag cttggagcga    6360
acgacctaca ccgaactgag atacctacag cgtgagctat gagaaagcgc cacgcttccc    6420
gaagggagaa aggcggacag gtatccggta agcggcaggg tcggaacagg agagcgcacg    6480
agggagcttc caggggggaaa cgcctggtat ctttatagtc ctgtcgggtt tcgccacctc    6540
tgacttgagc gtcgattttt gtgatgctcg tcagggggc ggagcctatg gaaaaacgcc    6600
agcaacgcgg cctttttacg gttcctggcc ttttgctggc cttttgctca catgttcttt    6660
cctgcgttat cccctgattc tgtggataac cgtattaccg cctttgagtg agctgatacc    6720
gctcgccgca gccgaacgac cgagcgcagc gagtcagtga gcgaggaagc ggaagagcgc    6780
ctgatgcggt attttctcct tacgcatctg tgcggtattt cacaccgcat agggtcatgg    6840
ctgcgccccg acacccgcca acacccgctg acgcgccctg acgggcttgt ctgctcccgg    6900
catccgctta cagacaagct gtgaccgtct ccgggagctg catgtgtcag aggttttcac    6960
cgtcatcacc gaaacgcgcg aggcagcaag gagatggcgc ccaacagtcc cccggccacg    7020
gggcctgcca ccatacccac gccgaaacaa gcgctcatga gcccgaagtg gcgagcccga    7080
tcttccccat cggtgatgtc ggcgatatag gcgccagcaa ccgcacctgt ggcgccggtg    7140
atgccggcca cgatgcgtcc ggcgtagagg atctgctcat gtttgacagc ttatc    7195

<210> SEQ ID NO 11
<211> LENGTH: 7010
<212> TYPE: DNA
<213> ORGANISM: Artificial Sequence
<220> FEATURE:
<221> NAME/KEY: misc_feature
<222> LOCATION: (1)..(7010)
<223> OTHER INFORMATION: plasmid pBAD-alpha-beta-gamma
<221> NAME/KEY: CDS
<222> LOCATION: (1320)..(2000)
<223> OTHER INFORMATION: red alpha
<221> NAME/KEY: CDS
<222> LOCATION: (2086)..(2871)
<223> OTHER INFORMATION: red beta
<221> NAME/KEY: CDS
<222> LOCATION: (3403)..(3819)
<223> OTHER INFORMATION: red gamma

<400> SEQUENCE: 11
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcatttttta     180
aatacccgcg agaaatagag ttgatcgtca aaaccaacat tgcgaccgac ggtggcgata     240
```

```
ggcatccggg tggtgctcaa aagcagcttc gcctggctga tacgttggtc ctcgcgccag    300
cttaagacgc taatccctaa ctgctggcgg aaaagatgtg acagacgcga cggcgacaag    360
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttcccctt gcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag gggatcattt    960
tgcgcttcag cctacttttt catactcccg ccattcagag aagaaaccaa ttgtccatat   1020
tgcatcagac attgccgtca ctgcgtcttt tactggctct ctcgctaac caaaccggta   1080 accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgcttttta   1260
tcgcaactct ctactgtttc tccataccccg ttttttttggg ctagcaggag gaattcacc   1319
atg aca ccg gac att atc ctg cag cgt acc ggg atc gat gtg aga gct       1367
Met Thr Pro Asp Ile Ile Leu Gln Arg Thr Gly Ile Asp Val Arg Ala
        290             295                 300 gtc gaa cag ggg gat gat gcg tgg cac aaa tta cgg ctc ggc gtc atc       1415
Val Glu Gln Gly Asp Asp Ala Trp His Lys Leu Arg Leu Gly Val Ile
    305                 310                 315 acc gct tca gaa gtt cac aac gtg ata gca aaa ccc cgc tcc gga aag       1463
Thr Ala Ser Glu Val His Asn Val Ile Ala Lys Pro Arg Ser Gly Lys
320                 325                 330                 335 aag tgg cct gac atg aaa atg tcc tac ttc cac acc ctg ctt gct gag       1511
Lys Trp Pro Asp Met Lys Met Ser Tyr Phe His Thr Leu Leu Ala Glu
            340                 345                 350 gtt tgc acc ggt gtg gct ccg gaa gtt aac gct aaa gca ctg gcc tgg       1559
Val Cys Thr Gly Val Ala Pro Glu Val Asn Ala Lys Ala Leu Ala Trp
        355                 360                 365 gga aaa cag tac gag aac gac gcc aga acc ctg ttt gaa ttc act tcc       1607
Gly Lys Gln Tyr Glu Asn Asp Ala Arg Thr Leu Phe Glu Phe Thr Ser
    370                 375                 380 ggc gtg aat gtt act gaa tcc ccg atc atc tat cgc gac gaa agt atg       1655
Gly Val Asn Val Thr Glu Ser Pro Ile Ile Tyr Arg Asp Glu Ser Met
385                 390                 395 cgt acc gcc tgc tct ccc gat ggt tta tgc agt gac ggc aac ggc ctt       1703
Arg Thr Ala Cys Ser Pro Asp Gly Leu Cys Ser Asp Gly Asn Gly Leu
400                 405                 410                 415 gaa ctg aaa tgc ccg ttt acc tcc cgg gat ttc atg aag ttc cgg ctc       1751
Glu Leu Lys Cys Pro Phe Thr Ser Arg Asp Phe Met Lys Phe Arg Leu
            420                 425                 430 ggt ggt ttc gag gcc ata aag tca gct tac atg gcc cag gtg cag tac       1799
Gly Gly Phe Glu Ala Ile Lys Ser Ala Tyr Met Ala Gln Val Gln Tyr
        435                 440                 445 agc atg tgg gtg acg cga aaa aat gcc tgg tac ttt gcc aac tat gac       1847
Ser Met Trp Val Thr Arg Lys Asn Ala Trp Tyr Phe Ala Asn Tyr Asp
```

```
                450              455              460
ccg cgt atg aag cgt gaa ggc ctg cat tat gtc gtt att gag cgg gat    1895
Pro Arg Met Lys Arg Glu Gly Leu His Tyr Val Val Ile Glu Arg Asp
    465              470              475 gaa aag tac atg gcg agt ttt gac gag atc gtg ccg gag ttc atc gaa    1943
Glu Lys Tyr Met Ala Ser Phe Asp Glu Ile Val Pro Glu Phe Ile Glu
480              485              490              495 aaa atg gac gag gca ctg gct gaa att ggt ttt gta ttt ggg gag caa    1991
Lys Met Asp Glu Ala Leu Ala Glu Ile Gly Phe Val Phe Gly Glu Gln
                500              505              510 tgg cga tag atccggtacc cgagcacgtg ttgacaatta atcatcggca            2040
Trp Arg  * tagtatatcg gcatagtata atacgacaag gtgaggaact aaacc atg agt act      2094
                                                  Met Ser Thr
                                                    1 gca ctc gca acg ctg gct ggg aag ctg gct gaa cgt gtc ggc atg gat    2142
Ala Leu Ala Thr Leu Ala Gly Lys Leu Ala Glu Arg Val Gly Met Asp
      5               10               15 tct gtc gac cca cag gaa ctg atc acc act ctt cgc cag acg gca ttt    2190
Ser Val Asp Pro Gln Glu Leu Ile Thr Thr Leu Arg Gln Thr Ala Phe
 20               25               30               35 aaa ggt gat gcc agc gat gcg cag ttc atc gca tta ctg atc gtt gcc    2238
Lys Gly Asp Ala Ser Asp Ala Gln Phe Ile Ala Leu Leu Ile Val Ala
               40               45               50 aac cag tac ggc ctt aat ccg tgg acg aaa gaa att tac gcc ttt cct    2286
Asn Gln Tyr Gly Leu Asn Pro Trp Thr Lys Glu Ile Tyr Ala Phe Pro
               55               60               65 gat aag cag aat ggc atc gtt ccg gtg gtg ggc gtt gat ggc tgg tcc    2334
Asp Lys Gln Asn Gly Ile Val Pro Val Val Gly Val Asp Gly Trp Ser
        70               75               80 cgc atc atc aat gaa aac cag cag ttt gat ggc atg gac ttt gag cag    2382
Arg Ile Ile Asn Glu Asn Gln Gln Phe Asp Gly Met Asp Phe Glu Gln
 85               90               95 gac aat gaa tcc tgt aca tgc cgg att tac cgc aag gac cgt aat cat    2430
Asp Asn Glu Ser Cys Thr Cys Arg Ile Tyr Arg Lys Asp Arg Asn His
100              105              110              115 ccg atc tgc gtt acc gaa tgg atg gat gaa tgc cgc cgc gaa cca ttc    2478
Pro Ile Cys Val Thr Glu Trp Met Asp Glu Cys Arg Arg Glu Pro Phe
                120              125              130 aaa act cgc gaa ggc aga gaa atc acg ggg ccg tgg cag tcg cat ccc    2526
Lys Thr Arg Glu Gly Arg Glu Ile Thr Gly Pro Trp Gln Ser His Pro
            135              140              145 aaa cgg atg tta cgt cat aaa gcc atg att cag tgt gcc cgt ctg gcc    2574
Lys Arg Met Leu Arg His Lys Ala Met Ile Gln Cys Ala Arg Leu Ala
        150              155              160 ttc gga ttt gct ggt atc tat gac aag gat gaa gcc gag cgc att gtc    2622
Phe Gly Phe Ala Gly Ile Tyr Asp Lys Asp Glu Ala Glu Arg Ile Val
165              170              175 gaa aat act gca tac act gca gaa cgt cag ccg gaa cgc gac atc act    2670
Glu Asn Thr Ala Tyr Thr Ala Glu Arg Gln Pro Glu Arg Asp Ile Thr
180              185              190              195 ccg gtt aac gat gaa acc atg cag gag att aac act ctg ctg atc gcc    2718
Pro Val Asn Asp Glu Thr Met Gln Glu Ile Asn Thr Leu Leu Ile Ala
                200              205              210 ctg gat aaa aca tgg gat gac gac tta ttg ccg ctc tgt tcc cag ata    2766
Leu Asp Lys Thr Trp Asp Asp Asp Leu Leu Pro Leu Cys Ser Gln Ile
            215              220              225 ttt cgc cgc gac att cgt gca tcg tca gaa ctg aca cag gcc gaa gca    2814
Phe Arg Arg Asp Ile Arg Ala Ser Ser Glu Leu Thr Gln Ala Glu Ala
```

-continued

|  |  |  |  |
|---|---|---|---|
| gta aaa gct ctt gga ttc ctg aaa cag aaa gcc gca gag cag aag gtg<br>Val Lys Ala Leu Gly Phe Leu Lys Gln Lys Ala Ala Glu Gln Lys Val<br>245                       250                       255 | 2862 |
| gca gca tag atctcgagaa gcttcctgct gaacatcaaa ggcaagaaaa<br>Ala Ala *<br>260 | 2911 |
| catctgttgt caaagacagc atccttgaac aaggacaatt aacagttaac aaataaaaac | 2971 |
| gcaaaagaaa atgccgatat cctattggca ttttctttta tttcttatca acataaaggt | 3031 |
| gaatcccata cctcgagctt cacgctgccg caagcactca gggcgcaagg gctgctaaaa | 3091 |
| ggaagcggaa cacgtagaaa gccagtccgc agaaacggtg ctgaccccgg atgaatgtca | 3151 |
| gctactgggc tatctggaca agggaaaacg caagcgcaaa gagaaagcag gtagcttgca | 3211 |
| gtgggcttac atggcgatag ctagactggg cggttttatg gacagcaagc gaaccggaat | 3271 |
| tgccagctgg ggcgccctct ggtaaggttg ggaagccctg caaagtaaac tggatggctt | 3331 |
| tcttgccgcc aaggatctga tggcgcaggg atcaagatc tgatcaagag acaggatgag | 3391 |
| gatcgtttcg c atg gat att aat act gaa act gag atc aag caa aag cat<br>           Met Asp Ile Asn Thr Glu Thr Glu Ile Lys Gln Lys His<br>            1               5                   10 | 3441 |
| tca cta acc ccc ttt cct gtt ttc cta atc agc ccg gca ttt cgc ggg<br>Ser Leu Thr Pro Phe Pro Val Phe Leu Ile Ser Pro Ala Phe Arg Gly<br>15                     20                    25 | 3489 |
| cga tat ttt cac agc tat ttc agg agt tca gcc atg aac gct tat tac<br>Arg Tyr Phe His Ser Tyr Phe Arg Ser Ser Ala Met Asn Ala Tyr Tyr<br>30                     35                    40                    45 | 3537 |
| att cag gat cgt ctt gag gct cag agc tgg gcg cgt cac tac cag cag<br>Ile Gln Asp Arg Leu Glu Ala Gln Ser Trp Ala Arg His Tyr Gln Gln<br>               50                    55                    60 | 3585 |
| ctc gcc cgt gaa gag aaa gag gca gaa ctg gca gac gac atg gaa aaa<br>Leu Ala Arg Glu Glu Lys Glu Ala Glu Leu Ala Asp Asp Met Glu Lys<br>65                     70                    75 | 3633 |
| ggc ctg ccc cag cac ctg ttt gaa tcg cta tgc atc gat cat ttg caa<br>Gly Leu Pro Gln His Leu Phe Glu Ser Leu Cys Ile Asp His Leu Gln<br>          80                     85                    90 | 3681 |
| cgc cac ggg gcc agc aaa aaa tcc att acc cgt gcg ttt gat gac gat<br>Arg His Gly Ala Ser Lys Lys Ser Ile Thr Arg Ala Phe Asp Asp Asp<br>95                     100                  105 | 3729 |
| gtt gag ttt cag gag cgc atg gca gaa cac atc cgg tac atg gtt gaa<br>Val Glu Phe Gln Glu Arg Met Ala Glu His Ile Arg Tyr Met Val Glu<br>110                   115                  120                  125 | 3777 |
| acc att gct cac cac cag gtt gat att gat tca gag gta taa<br>Thr Ile Ala His His Gln Val Asp Ile Asp Ser Glu Val *<br>              130                   135 | 3819 |
| aacgagtaga agcttggctg ttttggcgga tgagagaaga ttttcagcct gatacagatt | 3879 |
| aaatcagaac gcagaagcgg tctgataaaa cagaatttgc ctggcggcag tagcgcggtg | 3939 |
| gtcccacctg accccatgcc gaactcagaa gtgaaacgcc gtagcgccga tggtagtgtg | 3999 |
| gggtctcccc atgcgagagt agggaactgc caggcatcaa ataaaacgaa aggctcagtc | 4059 |
| gaaagactgg gcctttcgtt ttatctgttg tttgtcggtg aacgctctcc tgagtaggac | 4119 |
| aaatccgccg ggagcggatt tgaacgttgc gaagcaacgg cccggagggt ggcgggcagg | 4179 |
| acgcccgcca taaactgcca ggcatcaaat taagcagaag gccatcctga cggatggcct | 4239 |
| ttttgcgttt ctacaaactc ttttgtttat tttctaaat acattcaaat atgtatccgc | 4299 |
| tcatgagaca ataaccctga taaatgcttc aataatattg aaaaaggaag agtatgagta | 4359 |

```
ttcaacattt ccgtgtcgcc cttattccct tttttgcggc attttgcctt cctgtttttg      4419
ctcacccaga aacgctggtg aaagtaaaag atgctgaaga tcagttgggt gcacgagtgg      4479
gttacatcga actggatctc aacagcggta agatccttga gagttttcgc cccgaagaac      4539
gttttccaat gatgagcact tttaaagttc tgctatgtgg cgcggtatta tcccgtgttg      4599
acgccgggca agagcaactc ggtcgccgca tacactattc tcagaatgac ttggttgagt      4659
actcaccagt cacagaaaag catcttacgg atggcatgac agtaagagaa ttatgcagtg      4719
ctgccataac catgagtgat aacactgcgg ccaacttact tctgacaacg atcggaggac      4779
cgaaggagct aaccgctttt ttgcacaaca tgggggatca tgtaactcgc cttgatcgtt      4839
gggaaccgga gctgaatgaa gccataccaa acgacgagcg tgacaccacg atgcctgtag      4899
caatggcaac aacgttgcgc aaactattaa ctggcgaact acttactcta gcttcccggc      4959
aacaattaat agactggatg gaggcggata agttgcagg accacttctg cgctcggccc       5019
ttccggctgg ctggtttatt gctgataaat ctggagccgg tgagcgtggg tctcgcggta      5079
tcattgcagc actggggcca gatggtaagc cctcccgtat cgtagttatc tacacgacgg      5139
ggagtcaggc aactatggat gaacgaaata gacagatcgc tgagataggt gcctcactga      5199
ttaagcattg gtaactgtca gaccaagttt actcatatat actttagatt gatttacgcg      5259
ccctgtagcg gcgcattaag cgcggcgggt gtggtggtta cgcgcagcgt gaccgctaca      5319
cttgccagcg ccctagcgcc cgctcctttc gctttcttcc cttcctttct cgccacgttc      5379
gccggctttc cccgtcaagc tctaaatcgg gggctcccct tagggttccg atttagtgct      5439
ttacggcacc tcgaccccaa aaaacttgat ttgggtgatg gttcacgtag tgggccatcg      5499
ccctgataga cggtttttcg ccctttgacg ttggagtcca cgttctttaa tagtggactc      5559
ttgttccaaa cttgaacaac actcaaccct atctcgggct attcttttga tttataaggg      5619
attttgccga tttcggccta ttggttaaaa aatgagctga tttaacaaaa atttaacgcg      5679
aattttaaca aaatattaac gtttacaatt taaaaggatc taggtgaaga tcctttttga      5739
taatctcatg accaaaatcc cttaacgtga gttttcgttc cactgagcgt cagaccccgt      5799
agaaaagatc aaaggatctt cttgagatcc tttttttctg cgcgtaatct gctgcttgca      5859
aacaaaaaaa ccaccgctac cagcggtggt ttgtttgccg gatcaagagc taccaactct      5919
ttttccgaag gtaactggct tcagcagagc gcagatacca aatactgtcc ttctagtgta      5979
gccgtagtta ggccaccact tcaagaactc tgtagcaccg cctacatacc tcgctctgct      6039
aatcctgtta ccagtggctg ctgccagtgg cgataagtcg tgtcttaccg ggttggactc      6099
aagacgatag ttaccggata aggcgcagcg gtcgggctga acggggggtt cgtgcacaca      6159
gcccagcttg gagcgaacga cctacaccga actgagatac ctacagcgtg agctatgaga      6219
aagcgccacg cttcccgaag ggagaaaggc ggacaggtat ccggtaagcg gcagggtcgg      6279
aacaggagag cgcacgaggg agcttccagg gggaaacgcc tggtatcttt atagtcctgt      6339
cgggtttcgc cacctctgac ttgagcgtcg atttttgtga tgctcgtcag ggggcggag       6399 cctatggaaa aacgccagca acgcggcctt tttacggttc ctggccttt gctggccttt       6459 tgctcacatg ttctttcctg cgttatcccc tgattctgtg ataaccgta ttaccgcctt       6519 tgagtgagct gataccgctc gccgcagccg aacgaccgag cgcagcgagt cagtgagcga      6579
ggaagcggaa gagcgcctga tgcggtattt tctccttacg catctgtgcg gtatttcaca      6639 ccgcatag gg tcatggctgc gccccgacac ccgccaacac ccgctgacgc gccctgacgg      6699
```

```
gcttgtctgc tcccggcatc cgcttacaga caagctgtga ccgtctccgg gagctgcatg    6759
tgtcagaggt tttcaccgtc atcaccgaaa cgcgcgaggc agcaaggaga tggcgcccaa    6819
cagtcccccg gccacggggc ctgccaccat acccacgccg aaacaagcgc tcatgagccc    6879
gaagtggcga gcccgatctt ccccatcggt gatgtcggcg atataggcgc cagcaaccgc    6939
acctgtggcg ccggtgatgc cggccacgat gcgtccggcg tagaggatct gctcatgttt    6999
gacagcttat c                                                         7010
```

<210> SEQ ID NO 12
<211> LENGTH: 226
<212> TYPE: PRT
<213> ORGANISM: Artificial Sequence
<220> FEATURE:
<221> NAME/KEY: DOMAIN
<222> LOCATION: (1)..(226)
<223> OTHER INFORMATION: Red-alpha from plasmid pBAD-alpha-beta-gamma

<400> SEQUENCE: 12

```
Met Thr Pro Asp Ile Ile Leu Gln Arg Thr Gly Ile Asp Val Arg Ala
  1               5                  10                  15

Val Glu Gln Gly Asp Asp Ala Trp His Lys Leu Arg Leu Gly Val Ile
             20                  25                  30

Thr Ala Ser Glu Val His Asn Val Ile Ala Lys Pro Arg Ser Gly Lys
         35                  40                  45

Lys Trp Pro Asp Met Lys Met Ser Tyr Phe His Thr Leu Leu Ala Glu
     50                  55                  60

Val Cys Thr Gly Val Ala Pro Glu Val Asn Ala Lys Ala Leu Ala Trp
 65                  70                  75                  80

Gly Lys Gln Tyr Glu Asn Asp Ala Arg Thr Leu Phe Glu Phe Thr Ser
                 85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 13
<211> LENGTH: 261
<212> TYPE: PRT
<213> ORGANISM: Artificial Sequence
<220> FEATURE:
<221> NAME/KEY: DOMAIN
<222> LOCATION: (1)..(261)
<223> OTHER INFORMATION: Red-beta from plasmid pBAD-alpha-beta-gamma -continued

```
<400> SEQUENCE: 13

Met Ser Thr Ala Leu Ala Thr Leu Ala Gly Lys Leu Ala Glu Arg Val
 1               5                  10                  15

Gly Met Asp Ser Val Asp Pro Gln Glu Leu Ile Thr Thr Leu Arg Gln
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
    50                  55                  60

Ala Phe Pro Asp Lys Gln Asn Gly Ile Val Pro Val Val Gly Val Asp
65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
        195                 200                 205

Leu Ile Ala Leu Asp Lys Thr Trp Asp Asp Leu Leu Pro Leu Cys
    210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
                245                 250                 255

Gln Lys Val Ala Ala
            260

<210> SEQ ID NO 14
<211> LENGTH: 138
<212> TYPE: PRT
<213> ORGANISM: Artificial Sequence
<220> FEATURE:
<221> NAME/KEY: DOMAIN
<222> LOCATION: (1)..(138)
<223> OTHER INFORMATION: Red-gamma from plasmid pBAD-alpha-beta-gamma
      and plasmid pBAD-ET-gamma

<400> SEQUENCE: 14

Met Asp Ile Asn Thr Glu Thr Glu Ile Lys Gln Lys His Ser Leu Thr
 1               5                  10                  15

Pro Phe Pro Val Phe Leu Ile Ser Pro Ala Phe Arg Gly Arg Tyr Phe
            20                  25                  30

His Ser Tyr Phe Arg Ser Ser Ala Met Asn Ala Tyr Tyr Ile Gln Asp
        35                  40                  45

Arg Leu Glu Ala Gln Ser Trp Ala Arg His Tyr Gln Gln Leu Ala Arg
    50                  55                  60

Glu Glu Lys Glu Ala Glu Leu Ala Asp Asp Met Glu Lys Gly Leu Pro
```

```
                65                  70                  75                  80
Gln His Leu Phe Glu Ser Leu Cys Ile Asp His Leu Gln Arg His Gly
                    85                  90                  95

Ala Ser Lys Lys Ser Ile Thr Arg Ala Phe Asp Asp Val Glu Phe
                100                 105                 110

Gln Glu Arg Met Ala Glu His Ile Arg Tyr Met Val Glu Thr Ile Ala
            115                 120                 125

His His Gln Val Asp Ile Asp Ser Glu Val
    130                 135
```

DNA CLONING METHOD RELYING ON THE E. COLI RECE/RECT RECOMBINATION SYSTEM

The invention refers to a novel method for cloning DNA molecules using a homologous recombination mechanism between at least two DNA molecules. Further, novel reagent kits suitable for DNA cloning are provided.

Current methods for cloning foreign DNA in bacterial cells usually comprise the steps of providing a suitable bacterial vector, cleaving said vector with a restriction enzyme and in vitro-inserting a foreign DNA fragment in said vector. The resulting recombinant vectors are then used to transform bacteria. Although such cloning methods have been used successfully for about 20 years they suffer from several drawbacks. These drawbacks are, in particular, that the in vitro steps required for inserting foreign DNA in a vector are often very complicated and time-consuming, if no suitable restriction sites are available on the foreign DNA or the vector.

Furthermore, current methods usually rely on the presence of suitable restriction enzyme cleavage sites in the vector into which the foreign DNA fragment is placed. This imposes two limitations on the final cloning product. First, the foreign DNA fragment can usually only be inserted into the vector at the position of such a restriction site or sites. Thus, the cloning product is limited by the disposition of suitable restriction sites and cloning into regions of the vector where there is no suitable restriction site, is difficult and often imprecise. Second, since restriction sites are typically 4 to 8 base pairs in length, they occur a multiple number of times as the size of the DNA molecules being used increases. This represents a practical limitation to the size of the DNA molecules that can be manipulated by most current cloning techniques. In particular, the larger sizes of DNA cloned into vectors such as cosmids, BACs, PACs and P1s are such that it is usually impractical to manipulate them directly by restriction enzyme based techniques. Therefore, there is a need for providing a new cloning method, from which the drawbacks of the prior art have at least partly been eliminated.

According to the present invention it was found that an efficient homologous recombination mechanism between two DNA molecules occurs at usable frequencies in a bacterial host cell which is capable of expressing the products of the recE and recT genes or functionally related genes such as the redα and redβ genes, or the phage P22 recombination system (Kolodner et al., Mol.Microbiol. 11 (1994) 23–30; Fenton, A. C. and Poteete, A. R., Virology 134 (1984) 148–160; Poteete, A. R. and Fenton, A. C., Virology 134 (1984) 161–167). This novel method of cloning DNA fragments is termed "ET cloning".

The identification and characterization of the E. coli RecE and RecT proteins is described Gillen et al. (J.Bacteriol. 145 (1981), 521–532) and Hall et al. (J.Bacteriol. 175 (1993), 277–287). Hall and Kolodner (Proc.Natl.Acad.Sci. USA 91 (1994), 3205–3209) disclose in vitro homologous pairing and strand exchange of linear double-stranded DNA and homologous circular single-stranded DNA promoted by the RecT protein. Any references to the use of this method for the cloning of DNA molecules in cells cannot be found therein.

The recET pathway of genetic recombination in E. coli is known (Hall and Kolodner (1994), supra; Gillen et al. (1981), supra). This pathway requires the expression of two genes, recE and recT. The DNA sequence of these genes has been published (Hall et al., supra). The RecE protein is similar to bacteriophage proteins, such as λ exo or λ Redα (Gillen et al., J.Mol.Biol.113 (1977), 27–41; Little, J.Biol.Chem. 242 (1967), 679–686; Radding and Carter, J.Biol.Chem. 246 (1971), 2513–2518; Joseph and Kolodner, J.Biol.Chem. 258 (1983), 10418–10424). The RecT protein is similar to bacteriophage proteins, such as λ β-protein or λ Redβ (Hall et al. (1993), supra; Muniyappa and Radding, J.Biol.Chem. 261 (1986), 7472–7478; Kmiec and Hollomon, J.Biol.Chem.256 (1981), 12636–12639). The content of the above-cited documents is incorporated herein by reference.

Oliner et al. (Nucl.Acids Res. 21 (1993), 5192–5197) describe in vivo cloning of PCR products in E. coli by intermolecular homologous: recombination between a linear PCR product and a linearized plasmid vector. Other previous attempts to develop new cloning methods based on homologous recombination in prokaryotes, too, relied on the use of restriction enzymes to linearise the vector (Bubeck et al., Nucleic Acids Res. 21 (1993), 3601–3602; Oliner et al., Nucleic Acids Res. 21 (1993), 5192–5197; Degryse, Gene 170 (1996), 45–50) or on the host-specific recA-dependent recombination system (Hamilton et al., J.Bacteriol. 171 (1989), 4617–4622; Yang et al., Nature Biotech. 15 (1997), 859–865; Dabert and Smith, Genetics 145 (1997), 877–889). These methods are of very limited applicability and are hardly used in practice.

The novel method of cloning DNA according to the present invention does not require in vitro treatments with restriction enzymes or DNA ligases and is therefore fundamentally distinct from the standard methodologies of DNA cloning. The method relies on a pathway of homologous recombination in E. coli involving the recE and recT gene products, or the redα and redβ gene products, or functionally equivalent gene products. The method covalently combines one preferably linear and preferably extrachromosomal DNA fragment, the DNA fragment to be cloned, with one second preferably circular DNA vector molecule, either an episome or the endogenous host chromosome or chromosomes. It is therefore distinct from previous descriptions of cloning in E. coli by homologous recombination which either rely on the use of two linear DNA fragments or different recombination pathways.

The present invention provides a flexible way to use homologous recombination to engineer large DNA molecules including an intact >76 kb plasmid and the E. coli chromosome. Thus, there is practically no limitation of target choice either according to size or site. Therefore, any recipient DNA in a host cell, from high copy plasmid to the genome, is amenable to precise alteration. In addition to engineering large DNA molecules, the invention outlines new, restriction enzyme-independent approaches to DNA design. For example, deletions between any two chosen base pairs in a target episome can be made by choice of oligonucleotide homology arms. Similarly, chosen DNA sequences can be inserted at a chosen base pair to create, for example, altered protein reading frames. Concerted combinations of insertions and deletions, as well as point mutations, are also possible. The application of these strategies is particularly relevant to complex or difficult DNA constructions, for example, those intended for homologous recombinations in eukaryotic cells, e.g. mouse embryonic stem cells. Further, the present invention provides a simple way to position site specific recombination target sites exactly where desired. This will simplify applications of site specific recombination in other living systems, such as plants and mice.

A subject matter of the present invention is a method for cloning DNA molecules in cells comprising the steps:

a) providing a host cell capable of performing homologous recombination, b) contacting in said host cell a first DNA molecule which is capable of being replicated in said host cell with a second DNA molecule comprising at least two regions of sequence homology to regions on the first DNA molecule, under conditions which favour homologous recombination between said first and second DNA molecules and c) selecting a host cell in which homologous recombination between said first and second DNA molecules has occurred.

In the method of the present invention the homologous recombination preferably occurs via the recET mechanism, i.e. the homologous recombination is mediated by the gene products of the recE and the recT genes which are preferably selected from the *E. coli* genes recE and recT or functionally related genes such as the phage λ redα and redβ genes.

The host cell suitable for the method of the present invention preferably is a bacterial cell, e.g. a gram-negative bacterial cell. More preferably, the host cell is an enterobacterial cell, such as Salmonella, Klebsielia or Escherichia. Most preferably the host cell is an *Escherichia coli* cell. It should be noted, however, that the cloning method of the present invention is also suitable for eukaryotic cells, such a s fungi, plant or animal c ell s.

Preferably, the host cell used for homologous recombination and is propagation of the cloned DNA can be any cell, e.g. a bacterial strain in which the products of the recE and recT, or redα and redβ, genes are expressed. The host cell may comprise the recE and recT genes located on the host cell chromosome or on non-chromosomal DNA, preferably on a vector, e.g. a plasmid. In a preferred case, the RecE and RecT, or Redα and Redβ, gene products are expressed from two different regulatable promoters, such as the arabinose-inducible BAD promoter or the lac promoter or from non-regulatable promoters. Alternatively, the recE and recT, or redα and redβ, genes are expressed on a polycistronic mRNA from a single regulatable or non-regulatable promoter. Preferably the expression is controlled by regulatable promoters.

Especially preferred is also an embodiment, wherein the recE or redα gene is expressed by a regulatable promoter. Thus, the recombinogenic potential of the system is only elicited when required and, at other times, possible undesired recombination reactions are limited. The recT or redβ gene, on the other hand, is preferably overexpressed with respect to recE or redα. This may be accomplished by using a strong constitutive promoter, e.g. the EM7 promoter and/or by using a higher copy number of recT, or redβ, versus recE, or redα, genes.

For the purpose of the present invention any recE and recT genes are suitable insofar as they allow a homologous recombination of first and second DNA molecules with sufficient efficiency to give rise to recombination products in more than 1 in $10^9$ cells transfected with DNA. The recE and recT genes may be derived from any bacterial strain or from bacteriophages or may be mutants and variants thereof. Preferred are recE and recT genes which are derived from *E. coli* or from *E. coli* bacteriophages, such as the redα and redβ genes from lambdoid phages, e.g. bacteriophage λ.

"More preferably, the recE or redα gene is selected from a nucleic acid molecule comprising (a) the nucleic acid sequence from position 1320 (ATG) to 2159 (GAC) as depicted in FIG. 7B or SEQ ID No. 2, (b) the nucleic acid sequence from position 1320 (ATG) to 1998 (CGA) as depicted in FIG. 14B or SEQ ID No. 11, (c) a nucleic acid encoding the same polypeptide within the degeneracy of the genetic code and/or (d) a nucleic acid sequence which hybridizes under stringent conditions with the nucleic acid sequence from (a), (b) and/or (c)."

"More preferably, the recT or redβ gene is selected from a nucleic acid molecule comprising (a) the nucleic acid sequence from position 2155 (ATG) to 2961 (GM) as depicted in FIG. 7B or SEQ ID No. 4, (b) the nucleic acid sequence from position 2086 (ATG) to 2868 (GCA) as depicted in FIG. 14B or SEQ ID No. 11, (c) a nucleic acid encoding the same polypeptide within the degeneracy of the genetic code and/or (d) a nucleic acid sequence which hybridizes under stringent conditions with the nucleic acid sequences from (a), (b) and/or (c)."

It should be noted that the present invention also encompasses mutants and variants of the given sequences, e.g. naturally occurring mutants and variants or mutants and variants obtained by genetic engineering. Further it should be noted that the recE gene depicted in FIG. 7B is an already truncated gene encoding amino acids 588–866 of the native protein. Mutants and variants preferably have a nucleotide sequence identity of at least 60%, preferably of at least 70% and more preferably of at least 80% of the recE and recT sequences depicted in FIG. 7B and 13B, and of the redα and redβ sequences depicted in FIG. 14B.

According to the present invention hybridization under stringent conditions preferably is defined according to Sambrook et al. (1989), infra, and comprises a detectable hybridization signal after washing for 30 min in 0.1×SSC, 0.5% SDS at 55° C., preferably at 62° C. and more preferably at 68° C.

In a preferred case the recE and recT genes are derived from the corresponding endogenous genes present in the *E. coli* K12 strain and its derivatives or from bacteriophages. In particular, strains that carry the sbcA mutation are suitable. Examples of such strains are JC8679 and JC 9604 (Gillen et al. (1981), supra). Alternatively, the corresponding genes may also be obtained from other coliphages such as lambdoid phages or phage P22.

The genotype of JC 8679 and JC 9604 is Sex (Hfr, F+, F–, or F') : F–.JC 8679 comprises the mutations: recBC 21, recC 22, sbcA 23, thr-1, ara-14, leu B 6, DE (gpt-proA) 62, lacY1, tsx-33, gluV44 (AS), galK2 (Oc), LAM-, his-60, relA 1, rps L31 (strR), xyl A5, mtl-1, argE3 (Oc) and thi-1. JC 9604 comprises the same mutations and further the mutation recA 56.

Further, it should be noted that the recE and recT, or redα and redβ, genes can be isolated from a first donor source, e.g. a donor bacterial cell and transformed into a second receptor source, e.g. a receptor bacterial or eukaryotic cell in which they are expressed by recombinant DNA means.

In one embodiment of the invention, the host cell used is a bacterial strain having an sbcA mutation, e.g. one of *E. coli* strains JC 8679 and JC 9604 mentioned above. However, the method of the invention is not limited to host cells having an sbcA mutation or analogous cells. Surprisingly, it has been found that the cloning method of the invention also works in cells without sbcA mutation, whether recBC+ or recBC–, e.g. also in prokaryotic recBC+ host cells, e.g. in *E. coli* recBC+ cells. In that case preferably those host cells are used in which the product of a recBC type exonuclease inhibitor gene is expressed. Preferably, the exonuclease inhibitor is capable of inhibiting the host recBC system or an equivalent thereof. A suitable example of such exonuclease inhibitor gene is the λ redγ gene (Murphy, J.Bacteriol. 173 (1991), 5808–5821) and functional equivalents thereof, respectively, which, for example, can be obtained from other coliphages such as from phage P22 (Murphy, J.Biol.Chem. 269 (1994), 22507–22516).

"More preferably, the exonuclease inhibitor gene is selected from a nucleic acid molecule comprising
 (a) the nucleic acid sequence from position 3588 (ATG) to 4002 (GTA) as depicted in FIG. 13B or SEQ ID No. 10 or 11,
 (b) a nucleic acid encoding the same polypeptide within the degeneracy of the genetic code and/or
 (c) a nucleic acid sequence which hybridizes under stringent conditions as defined above with the nucleic acid sequence from (a) and/or (b)."

Surprisingly, it has been found that the expression of an exonuclease inhibitor gene in both recBC+ and recBC− strains leads to significant improvement of cloning efficiency.

The cloning method according to the present invention employs a homologous recombination between a first DNA molecule and a second DNA molecule. The first DNA molecule can be any DNA molecule that carries an origin of replication which is operative in the host cell, e.g. an *E. coli* replication origin. Further, the first DNA molecule is present in a form which is capable of being replicated in the host cell. The first DNA molecule, i.e. the vector, can be any extrachromosomal DNA molecule containing an origin of replication which is operative in said host cell, e.g. a plasmid including single, low, medium or high copy plasmids or other extrachromosomal circular DNA molecules based on cosmid, P1, BAC or PAC vector technology. Examples of such vectors are described, for example, by Sambrook et al. (Molecular Cloning, Laboratory Manual, 2nd Edition (1989), Cold Spring Harbor Laboratory Press) and loannou et al. (Nature Genet. 6 (1994), 84–89) or references cited therein. The first DNA molecule can also be a host cell chromosome, particularly the *E. coli* chromosome. Preferably, the first DNA molecule is a double-stranded DNA molecule.

The second DNA molecule is preferably a linear DNA molecule and comprises at least two regions of sequence homology, preferably of sequence identity to regions on the first DNA molecule. These homology or identity regions are preferably at least 15 nucleotides each, more preferably at least 20 nucleotides and, most preferably, at least 30 nucleotides each. Especially good results were obtained when using sequence homology regions having a length of about 40 or more nucleotides, e.g. 60 or more nucleotides. The two sequence homology regions can be located on the linear DNA fragment so that one is at one end and the other is at the other end, however they may also be located internally. Preferably, also the second DNA molecule is a double-stranded DNA molecule.

The two sequence homology regions are chosen according to the experimental design. There are no limitations on which regions of the first DNA molecule can be chosen for the two sequence homology regions located on the second DNA molecule, except that the homologous recombination event cannot delete the origin of replication of the first DNA molecule. The sequence homology regions can be interrupted by non-identical sequence regions as long as sufficient sequence homology is retained for the homologous recombination reaction. By using sequence homology arms having non-identical sequence regions compared to the target site mutations such as substitutions, e.g. point mutations, insertions and/or deletions may be introduced into the target site by ET cloning.

The second foreign DNA molecule which is to be cloned in the bacterial cell may be derived from any source. For example, the second DNA molecule may be synthesized by a nucleic acid amplification reaction such as a PCR where both of the DNA oligonucleotides used to prime the amplification contain in addition to sequences at the 3'-ends that serve as a primer for the amplification, one or the other of the two homology regions. Using oligonucleotides of this design, the DNA product of the amplification can be any DNA sequence suitable for amplification and will additionally have a sequerne homology region at each end.

A specific example of the generation of the second DNA molecule is the amplification of a gene that serves to convey a phenotypic difference to the bacterial host cells, in particular, antibiotic resistance. A simple variation of this procedure involves the use of oligonucleotides that include other sequences in addition to the PCR primer sequence and the sequence homology region. A further simple variation is the use of more than two amplification primers to generate the amplification product. A further simple variation is the use of more than one amplification reaction to generate the amplification product. A further variation is the use of DNA fragments obtained by methods other than PCR, for example, by endonuclease or restriction enzyme cleavage to linearize fragments from any source of DNA.

It should be noted that the second DNA molecule is not necessarily a single species of DNA molecule. It is of course possible to use a heterogenous population of second DNA molecules, e.g. to generate a DNA library, such as a genomic or cDNA library.

The method of the present invention may comprise the contacting of the first and second DNA molecules in vivo. In one embodiment of the present invention the second DNA fragment is transformed into a bacterial strain that already harbors the first vector DNA molecule. In a different embodiment, the second DNA molecule and the first DNA molecule are mixed together in vitro before co-transformation in the bacterial host cell. These two embodiments of the present invention are schematically depicted in FIG. 1. The method of transformation can be any method known in the art (e.g. Sambrook et al. supra). The preferred method of transformation or co-transformation, however, is electroporation.

Figure 2:
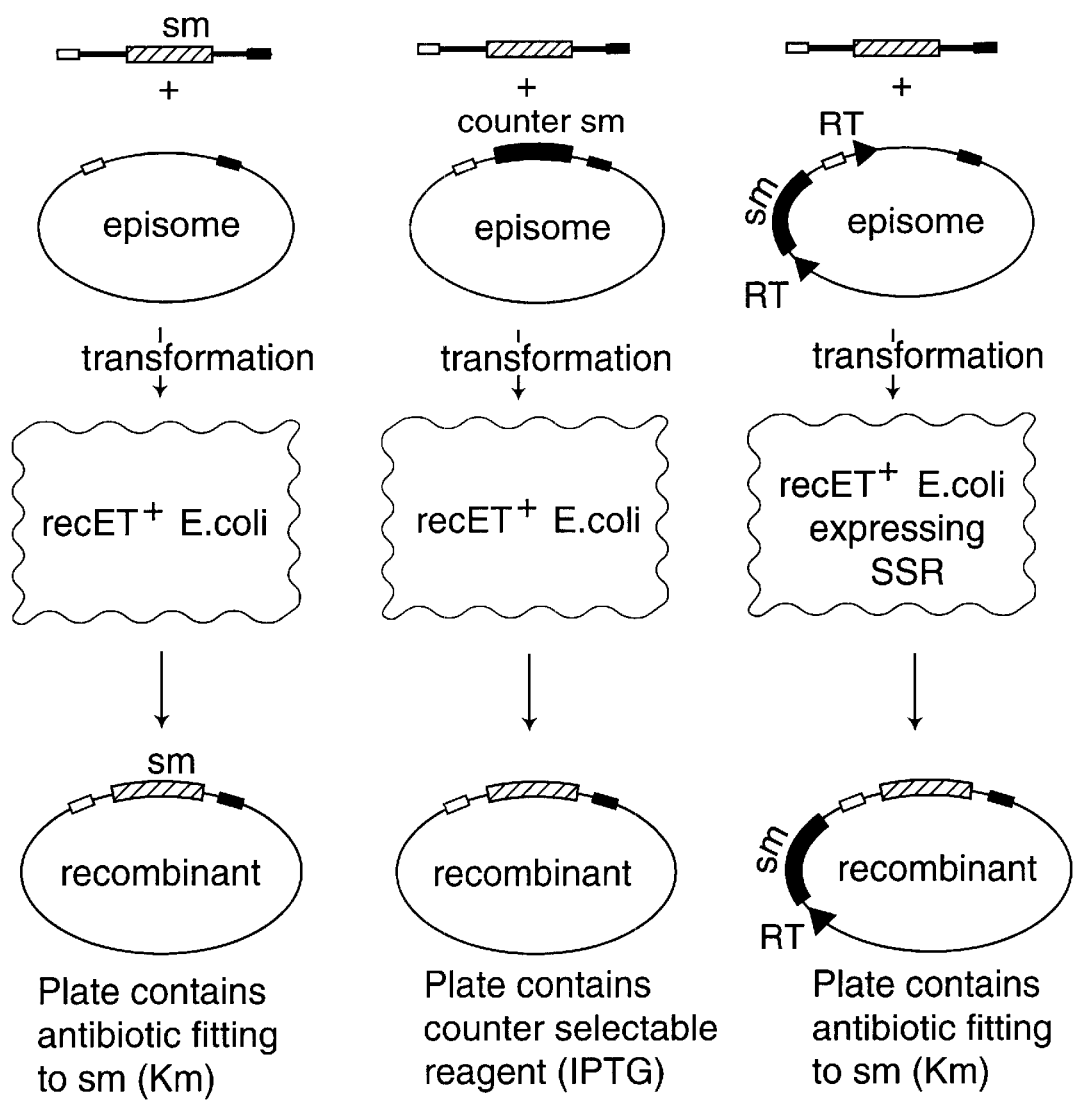

After contacting the first and second DNA molecules under conditions which favour homologous recombination between first and second DNA molecules via the ET cloning mechanism a host cell is selected, in which homologous recombination between said first and second DNA molecules has occurred. This selection procedure can be carried out by several different methods. In the following three preferred selection methods are depicted in FIG. 2 and described in detail below.

In a first selection method a second DNA fragment is employed which carries a gene for a marker placed between the two regions of sequence homology wherein homologous recombination is detectable by expression of the marker gene. The marker gene may be a gene for a phenotypic marker which is not expressed in the host or from the first DNA molecule. Upon recombination by ET cloning, the change in phenotype of the host strain conveyed by the stable acquisition of the second DNA fragment identifies the ET cloning product.

In a preferred case, the phenotypic marker is a gene that conveys resistance to an antibiotic, in particular, genes that convey resistance to kanamycin, ampillicin, chloramphenicol, tetracyclin or any other substance that shows bacteriocidal or bacteriostatic effects on the bacterial strain employed.

A simple variation is the use of a gene that complements a deficiency present within the bacterial host strain employed. For example, the host strain may be mutated so that it is incapable of growth without a metabolic supplement. In the absence of this supplement, a gene on the second DNA fragment can complement the mutational defect thus permitting growth. Only those cells which contain the episome carrying the intended DNA rearrangement caused by the ET cloning step will grow.

In another example, the host strain carries a phenotypic marker gene which is mutated so that one of its codons is a stop codon that truncates the open reading frame. Expression of the full length protein from this phenotypic marker gene requires the introduction of a suppressor tRNA gene which, once expressed, recognizes the stop codon and permits translation of the full open reading frame. The suppressor tRNA gene is introduced by the ET cloning step and successful recombinants identified by selection for, or identification of, the expression of the phenotypic marker gene. In these cases, only those cells which contain the intended DNA rearrangement caused by the ET cloning step will grow.

A further simple variation is the use of a reporter gene that conveys a readily detectable change in colony colour or morphology. In a preferred case, the green fluorescence protein (GFP) can be used and colonies carrying the ET cloning product identified by the fluorescence emissions of GFP. In another preferred case, the lacZ gene can be used and colonies carrying the ET cloning product identified by a blue colony colour when X-gal is added to the culture medium.

In a second selection method the insertion of the second DNA fragment into the first DNA molecule by ET cloning alters the expression of a marker present on the first DNA molecule. In this embodiment the first DNA molecule contains at least one marker gene between the two regions of sequence homology and homologous recombination may be detected by an altered expression, e.g. lack of expression of the marker gene.

In a preferred application, the marker present the first DNA molecule is a counter-selectable gene product, such as the sacB, ccdB or tetracycline-resistance genes. In these cases, bacterial cells that carry the first DNA molecule unmodified by the ET cloning step after transformation with the second DNA fragment, or co-transformation with the second DNA fragment and the first DNA molecule, are plated onto a medium so the expression of the counter-selectable marker conveys a toxic or bacteriostatic effect on the host. Only those bacterial cells which contain the first DNA molecule carrying the intended DNA rearrangement caused by the ET cloning step will grow.

In another preferred application, the first DNA molecule carries a reporter gene that conveys a readily detectable change in colony colour or morphology. In a preferred case, the green fluorescence protein (GFP) can be present on the first DNA molecule and colonies carrying the first DNA molecule with or without the ET cloning product can be distinguished by differences in the fluorescence emissions of GFP. In another preferred case, the lacZ gene can be present on the first DNA molecule and colonies carrying the first DNA molecule with or without the ET cloning product identified by a blue or white colony colour when X-gal is added to the culture medium.

In a third selection method the integration of the second DNA fragment into the first DNA molecule by ET cloning removes a target site for a site specific recombinase, termed here an RT (for recombinase target) present on the first DNA molecule between the two regions of sequence homology. A homologous recombination event may be detected by removal of the target site.

In the absence of the ET cloning product, the RT is available for use by the corresponding site specific recombinase. The difference between the presence or not of this RT is the basis for selection of the ET cloning product. In the presence of this RT and the corresponding site specific recombinase, the site specific recombinase mediates recombination at this RT and changes the phenotype of the host so that it is either not able to grow or presents a readily observable phenotype. In the absence of this RT, the corresponding site specific recombinase is not able to mediate recombination.

In a preferred case, the first DNA molecule to which the second DNA fragment is directed, contains two RTs, one of which is adjacent to, but not part of, an antibiotic resistance gene. The second DNA fragment is directed, by design, to remove this RT. Upon exposure to the corresponding site specific recombinase, those first DNA molecules that do not carry the ET cloning product will be subject to a site specific recombination reaction between the RTs that remove the antibiotic resistance gene and therefore the first DNA molecule fails to convey resistance to the corresponding antibiotic. Only those first DNA molecules that contain the ET cloning product, or have failed to be site specifically recombined for some other reason, will convey resistance to the antibiotic.

In another preferred case, the RT to be removed by ET cloning of the second DNA fragment is adjacent to a gene that complements a deficiency present within the host strain employed. In another preferred case, the RT to be removed by ET cloning of the second DNA fragment is adjacent to a reporter gene that conveys a readily detectable change in colony colour or morphology.

In another preferred case, the RT to be removed by ET cloning of the second DNA fragment is anywhere on a first episomal DNA molecule and the episome carries an origin of replication incompatible with survival of the bacterial host cell if it is integrated into the host genome. In this case the host genome carries a second RT, which may or may not be a mutated RT so that the corresponding site specific recombinase can integrate the episome, via its RT, into the RT sited in the host genome. Other preferred. RTs include RTs for site specific recombinases of the resolvase/transposase class. RTs include those described from existing examples of site specific recombination as well as natural or mutated variations thereof.

The preferred site specific recombinases include Cre, FLP, Kw or any site specific recombinase of the integrase class. Other preferred site specific recombinases include site specific recombinases of the resolvase/transposase class.

There are no limitations on the method of expression of the site specific recombinase in the host cell. In a preferred method, the expression of the site specific recombinase is regulated so that expression can be induced and quenched according to the optimisation of the ET cloning efficiency. In this case, the site specific recombinase gene can be either integrated into the host genome or carried on an episome. In another preferred case, the site specific recombinase is expressed from an episome that carries a conditional origin of replication so that it can be eliminated from the host cell.

In another preferred case, at least two of the above three selection methods are combined. A particularly preferred case involves a two-step use of the first selection method above, followed by use of the second selection method. This combined use requires, most simply, that the DNA fragment to be cloned includes a gene, or genes that permits the identification, in the first step, of correct ET cloning products by the acquisition of a phenotypic change. In a second step, expression of the gene or genes introduced in the first step is altered so that a second round of ET cloning products can be identified. In a preferred example, the gene employed is the tetracycline resistance gene and the first step ET cloning products are identified by the acquisition of tetracycline resistance. In the second step, loss of expression of the tetracycline gene is identified by loss of sensitivity to nickel chloride, fusaric acid or any other agent that is toxic to the host cell when the tetracycline gene is expressed. This two-step procedure permits the identification of ET-cloning products by first the integration of a gene that conveys a phenotypic change on the host, and second by the loss of a related phenotypic change, most simply by removal of some of the DNA sequences integrated in the first step. Thereby the genes used to identify ET cloning products can be inserted and then removed to leave ET cloning products that are free of these genes.

In a further embodiment of the present invention the ET cloning may also be used for a recombination method comprising the steps of a) providing a source of RecE and RecT, or Redα and Redβ, proteins, b) contacting a first DNA molecule which is capable of being replicated in a suitable host cell with a second DNA molecule comprising at least two regions of sequence homology to regions on the first DNA molecule, under conditions which favour homologous recombination between said first and second DNA molecules and c) selecting DNA molecules in which a homologous recombination between said first and second DNA molecules has occurred.

The source of RecE and RecT, or Redα and Redβ, proteins may be either purified or partially purified RecE and RecT, or Redα and Redβ, proteins or cell extracts comprising RecE and RecT, or Redα and Redβ, proteins.

The homologous recombination event in this embodiment may occur in vitro, e.g. when providing a cell extract containing further components required for homologous recombination. The homologous recombination event, however, may also occur in vivo, e.g. by introducing RecE and RecT, or Redα and Redβ, proteins or the extract in a host cell (which may be recET positive or not, or redαβ positive or not) and contacting the DNA molecules in the host cell. When the recombination occurs in vitro the selection of DNA molecules may be accomplished by transforming the recombination mixture in a suitable host cell and selecting for positive clones as described above. When the recombination occurs in vivo the selection methods as described above may directly be applied.

A further subject matter of the invention is the use of cells, preferably bacterial cells, most preferably, *E. coli* cells capable of expressing the recE and recT, or redα and redβ, genes as a host cell for a cloning method involving homologous recombination.

Still a further subject matter of the invention is a vector system capable of expressing recE and recT, or redα and redβ, genes in a host cell and its use for a cloning method involving homologous recombination. Preferably, the vector system is also capable of expressing an exonuclease inhibitor gene as defined above, e.g. the λ redγ gene. The vector system may comprise at least one vector. The recE and recT, or redα and redβ, genes are preferably located on a single vector and more preferably under control of a regulatable promoter which may be the same for both genes or a single promoter for each gene. Especially preferred is a vector system which is capable of overexpressing the recT, or redβ, gene versus the recE, or redα, gene.

Still a further subject matter of the invention is the use of a source of RecE and RecT, or Redα and Redβ, proteins for a cloning method involving homologous recombination.

A still further subject matter of the invention is a reagent kit for cloning comprising (a) a host cell, preferably a bacterial host cell, (b) means of expressing recE and recT, or redα and redβ, genes in said host cell, e.g. comprising a vector system, and (c) a recipient cloning vehicle, e.g. a vector, capable of being replicated in said cell.

On the one hand, the recipient cloning vehicle which corresponds to the first DNA molecule of the process of the invention can already be present in the bacterial cell. On the other hand, it can be present separated from the bacterial cell.

In a further embodiment the reagent kit comprises (a) a source for RecE and RecT, or Redα and Redβ, proteins and (b) a recipient cloning vehicle capable of being propagated in a host cell and (c) optionally a host cell suitable for propagating said recipient cloning vehicle.

The reagent kit furthermore contains, preferably, means for expressing a site specific recombinase in said host cell, in particular, when the recipient ET cloning product contains at least one site specific recombinase target site. Moreover, the reagent kit can also contain DNA molecules suitable for use as a source of linear DNA fragments used for ET cloning, preferably by serving as templates for PCR generation of the linear fragment, also as specifically designed DNA vectors from which the linear DNA fragment is released by restriction enzyme cleavage, or as prepared linear fragments included in the kit for use as positive controls or other tasks. Moreover, the reagent kit can also contain nucleic acid amplification primers comprising a region of homology to said vector. Preferably, this region of homology is located at the 5'-end of the nucleic acid amplification primer.

The invention is further illustrated by the following Sequence listings, Figures and Examples.

SEQ ID NO. 1: shows the nucleic acid sequence of the plasmid pBAD24-rec ET (FIG. 7).

SEQ ID NOs 2/3: show the nucleic acid and amino acid sequences of the truncated recE gene (t-recE) present on pBAD24-recET at positions 1320–2162.

SEQ ID NOs 4/5: show the nucleic acid and amino acid sequences of the recT gene present on pBAD24-recET at position 2155–2972.

SEQ ID NOs 6/7: show the nucleic acid and amino acid sequences of the araC gene present on the complementary stand to the one shown of pBAD24-recET at positions 974–996.

SEQ ID NOs 8/9: show the nucleic acid an amino acid sequences of the bla gene present on pBAD24-recET at positions 3493–4353.

Figure 13A:
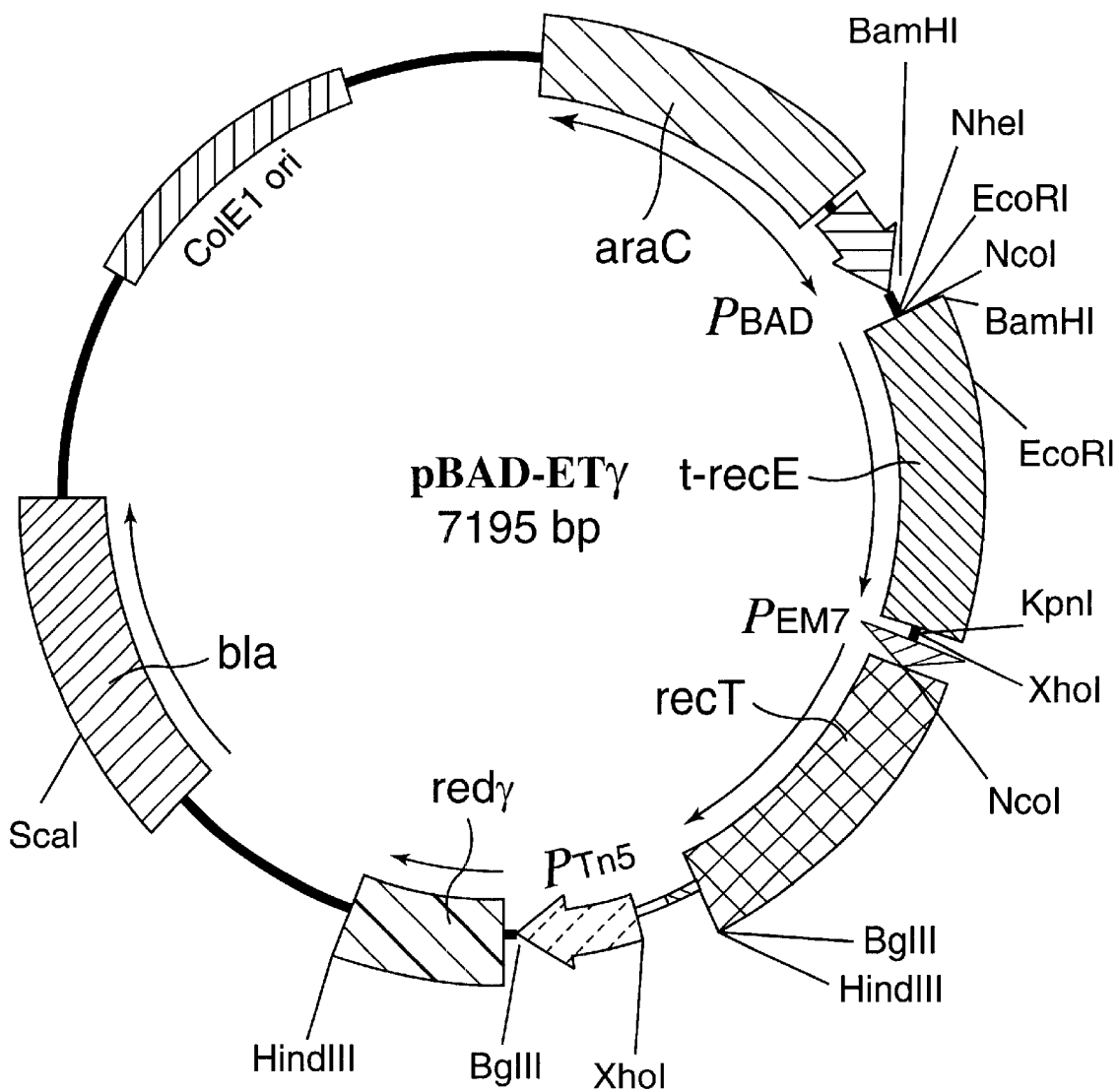
Figure 13D:

SEQ ID NO 10: shows the nucleic acid sequence of the plasmid pBAD-ETγ (FIG. 13).

SEQ ID No 11: shows the nucleic acid sequence of the plasmid pBAD-αβγ (FIG. 14) as well as the coding regions for the genes redα (1320–200), redβ (2086–2871) and redγ (3403–3819).

SEQ ID NOs 12–14: show the amino acid sequences of the Redα, Redβ and Redγ proteins, respectively. The redγ sequence is present on each of pBAD-ETγ (FIG. 13) and pBAD-αβγ (FIG. 14).

FIG. 1 A preferred method for ET cloning is shown by diagram. The linear DNA fragment to be cloned is synthesized by PCR using oligonucleotide primers that contain a left homology arm chosen to match sequences in the recipient episome and a sequence for priming in the PCR reaction, and a right homology arm chosen to match another sequence in the recipient episome and a sequence for priming in the PCR reaction. The product of the PCR reaction, here a selectable marker gene (sm1), is consequently flanked by the left and right homology arms and can be mixed together in vitro with the episome before co-transformation, or transformed into a host cell harboring the target episome. The host cell contains the products of the recE and recT gene. ET cloning products are identified by the combination of two selectable markers, sm1 and sm2 on the recipient episome.

FIG. 2 Three ways to identify ET cloning products are depicted. The first, (on the left of the figure), shows the acquisition, by ET cloning, of a gene that conveys a phenotypic difference to the host, here a selectable marker gene (sm). The second (in the centre of the figure) shows the loss, by ET cloning, of a gene that conveys a phenotypic difference to the host, here a counter selectable marker gene (counter-sm). The third shows the loss of a target site (RT, shown as triangles on the circular episome) for a site specific recombinase (SSR), by ET cloning. In this case, the correct ET cloning product deletes one of the target sites required by the SSR to delete a selectable marker gene (sm). The failure of the SSR to delete the sm gene identifies the correct ET cloning product.

FIG. 3 A simple example of ET cloning is presented. (a) Top panel—PCR products (left lane) synthesized from oligonucleotides designed as described in FIG. 1 to amplify by PCR a kanamycin resistance gene and to be flanked by homology arms present in the recipient vector, were mixed in vitro with the recipient vector (2nd lane) and cotransformed into a recET+ E. coli host. The recipient vector carried an ampillicin resistance gene. (b) Transformation of the sbcA E. coli strain JC9604 with either the PCR product alone (0.2 μg) or the vector alone (0.3 μg) did not convey resistance to double selection with ampicillin and kanamycin (amp+kan), however cotransformation of both the PCR product and the vector produced double resistant colonies. More than 95% of these colonies contained the correct ET cloning product where the kanamycin gene had precisely integrated into the recipient vector according to the choice of homology arms. The two lanes on the right of (a) show Pvu II restriction enzyme digestion of the recipient vector before and after ET cloning. (c) As for b, except that six PCR products (0.2 μg each) were cotransformed with pSVpaZ11 (0.3 μg each) into JC9604 and plated onto Amp+Kan plates or Amp plates. Results are plotted as Amp+Kan-resistant colonies, representing recombination products, divided by Amp-resistant colonies, representing the plasmid transformation efficiency of the competent cell preparation, ×10⁶. The PCR products were equivalent to the a-b PCR product except that homology arm lengths were varied. Results are from five experiments that used the same batches of competent cells and DNAs. Error bars represent standard deviation. (d) Eight products flanked by 50 bp homology arms were cotransformed with pSVpaZ11 into JC9604. All eight PCR products contained the same left homology arm and amplified neo gene. The right homology arms were chosen from the pSVpaZ11 sequence to be adjacent to (O), or at increasing distances (7–3100 bp), from the left. Results are from four experiments.

Figure 4B:
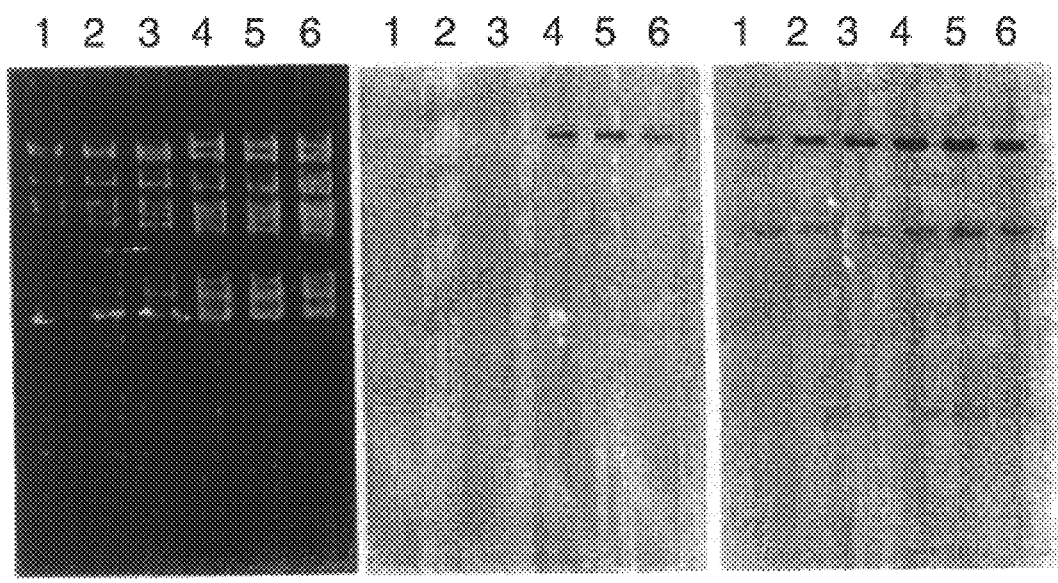

FIGS. 4(a) and (b) ET cloning in an approximately 100 kb P1 vector to exchange the selectable marker. A P1 clone which uses a kanamycin resistance gene as selectable marker and which contains at least 70 kb of the mouse Hox a gene cluster was used. Before ET cloning, this episome conveys kanamycin resistance (top panel, upper left) to its host E. coli which are ampillicin sensitive (top panel, upper right). A linear DNA fragment designed to replace the kanamycin resistance gene with an ampillicin resistance gene was made by PCR as outlined in FIG. 1 and transformed into E. coli host cells in which the recipient Hox a/P1 vector was resident. ET cloning resulted in the deletion of the kanamycin resistance gene, and restoration of kanamycin sensitivity (top panel, lower left) and the acquisition of ampillicin resistance (top panel, lower right). Precise DNA recombination was verified by restriction digestion and Southern blotting analyses of isolated DNA before and after ET cloning (lower panel).

Figure 5A:
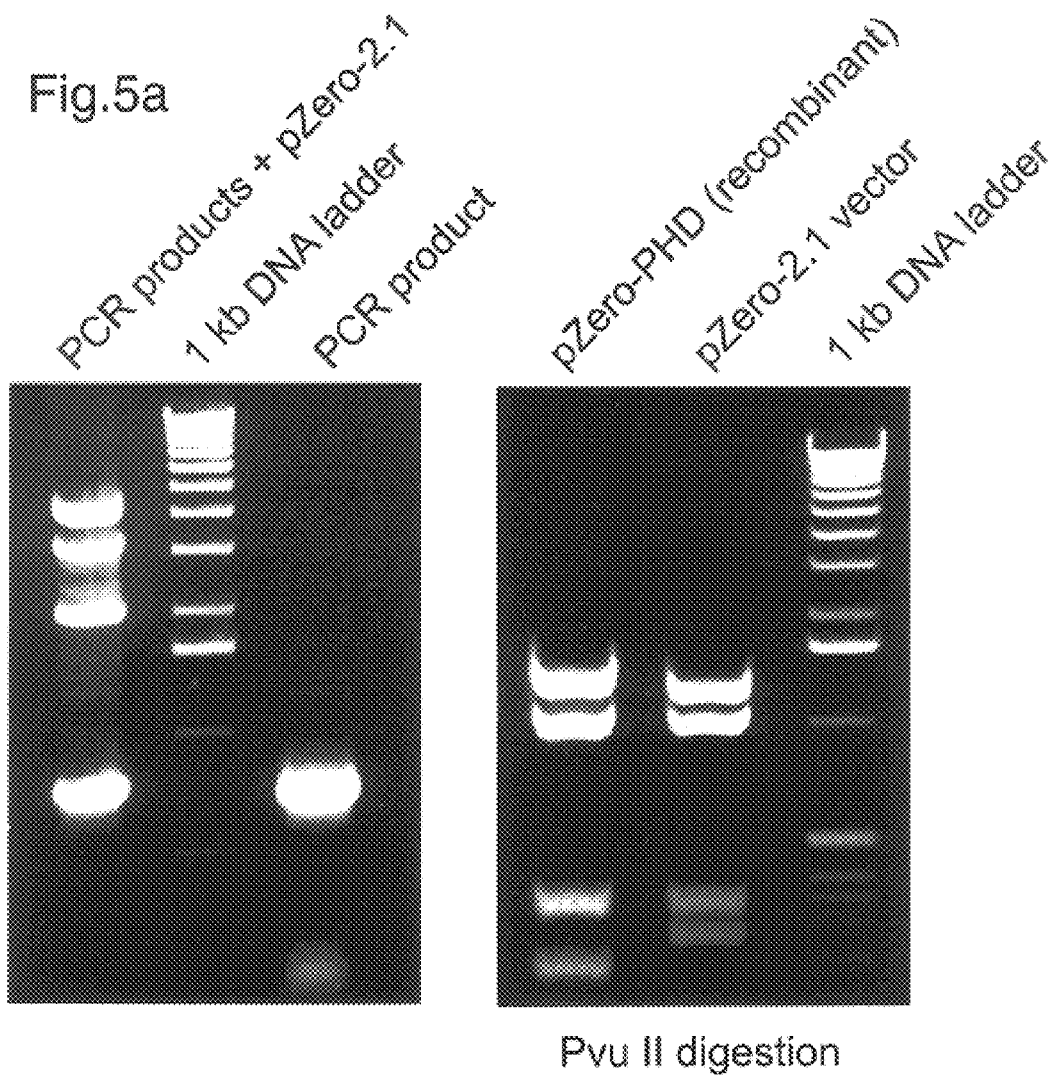

FIGS. 5(a) and (b) ET cloning to remove a counter selectable marker A PCR fragment (upper panel, left, third lane) made as outlined in FIGS. 1 and 2 to contain the kanamycin resistance gene was directed by homology arms to delete the counter selectable ccdB gene present in the vector, pZero-2.1. The PCR product and the pZero vector were mixed in vitro (upper panel, left, 1st lane) before cotransformation into a recE/recT+ E. coli host. Transformation of pZero-2.1 alone and plating onto kanamycin selection medium resulted in little colony growth (lower panel, left). Cotransformation of pZero-2.1 and the PCR product presented ET cloning products (lower panel, right) which showed the intended molecular event as visualized by Pvu II digestion (upper panel, right).

FIG. 6 ET cloning mediated by inducible expression of recE and recT from an episome. RecE/RecT mediate homologous recombination between linear and circular DNA molecules. (a) The plasmid pBAD24-recET was transformed into E. coli JC5547, and then batches of competent cells were prepared after induction of RecE/RecT expression by addition of L-arabinose for the times indicated before harvesting. A PCR product, made using oligonucleotides e and f to contain the chloramphenicol resistance gene (cm) of pMAK705 and 50 bp homology arms chosen to flank the ampicillin resistance gene (bla) of pBAD24-recET, was then transformed and recombinants identified on chloramphenicol plates. (b) Arabinose was added to cultures of pBAD24-recETtransformed JC5547 for different times immediately before harvesting for competent cell preparation. Total protein expression was analyzed by SDS-PAGE and Coomassie blue staining. (c) The number of chloramphenicol resistant colonies per pg of PCR product was normalized against a control for transformation efficiency, determined by including 5 pg pZero2.1, conveying kanamycin resistance, in the transformation and plating an aliquot onto Kan plates.

FIG. 7A The plasmid pBAD24-recET is shown by diagram. The plasmid contains the genes recE (in a truncated form) and recT under control of the inducible BAD promoter ($P_{BAD}$). The plasmid further contains an ampillicin resistance gene (Amp') and an araC gene.

FIG. 7B The nucleic acid sequence and the protein coding portions of pBAD24-recET are depicted.

Figure 8A:
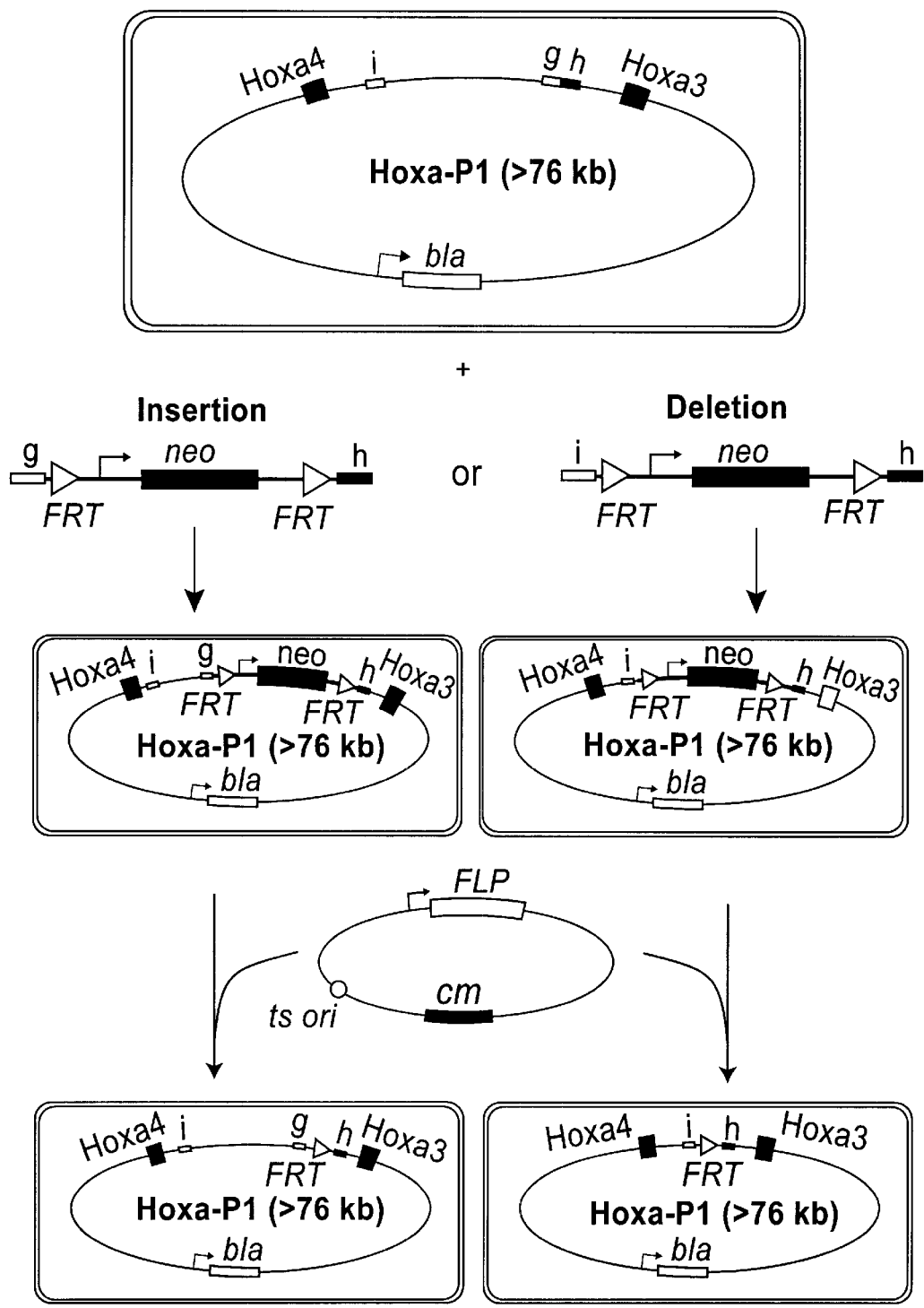

FIG. 8 Manipulation of a large E. coli episome by multiple recombination steps. FIG. 8a depicts the scheme of the recombination reactions. A P1 clone of the Mouse Hoxa complex, resident in JC9604, was modified by recombination with PCR products that contained the neo gene and two Flp recombination targets (FRTs). The two PCR products were identical except that one was flanked by g and h homology arms (insertion), and the other was flanked by i and h homology arms (deletion). In a second step, the neo gene was removed by Flp recombination between the FRTs by transient transformation of a Flp expression plasmid based on the pSC101 temperature-sensitive origin (ts ori). FIG. 8b (upper panel): ethidium bromide stained agarose gel showing EcoR1 digestions of P1 DNA preparations from three independent colonies for each step. FIG. 8b (middle panel): a Southern blot of the upper panel hybridized with a neo gene probe. FIG. 8b (lower panel): a Southern blot of the upper panel hybridized with a Hoxa3 probe to visualize the site of recombination. Lane 1 in each of the panels shows the original Hoxa3 P1 clone grown in *E. coli* strain NS3145. Lane 2 in each of the panels shows that replacement of the Tn903 kanamycin resistance gene in the P1 vector with an ampicillin resistance gene, increased the 8.1 kb band (lane 1) to 9.0 kb. Lane 3 in each of the panels shows that insertion of the Tn5-neo gene with g–h homology arms upstream of Hoxa3, increased the 6.7 kb band (lanes 1,2) to 9.0 kb. Lane 4 in each of the panels shows that Flp recombinase deleted the g–h neo gene reducing the 9.0 kb band (lane 3) back to 6.7 kb. Lane 5 in each of the panels shows that deletion of 6 kb of Hoxa3–4 intergenic DNA by replacement with the i–h neo gene, decreased the 6.7 kb band (lane 2) to 4.5 kb. Lane 6 in each of the panels shows that Flp recombinase deleted the i–h neo gene reducing the 4.5 kb band to 2.3 kb.

Figure 9A:
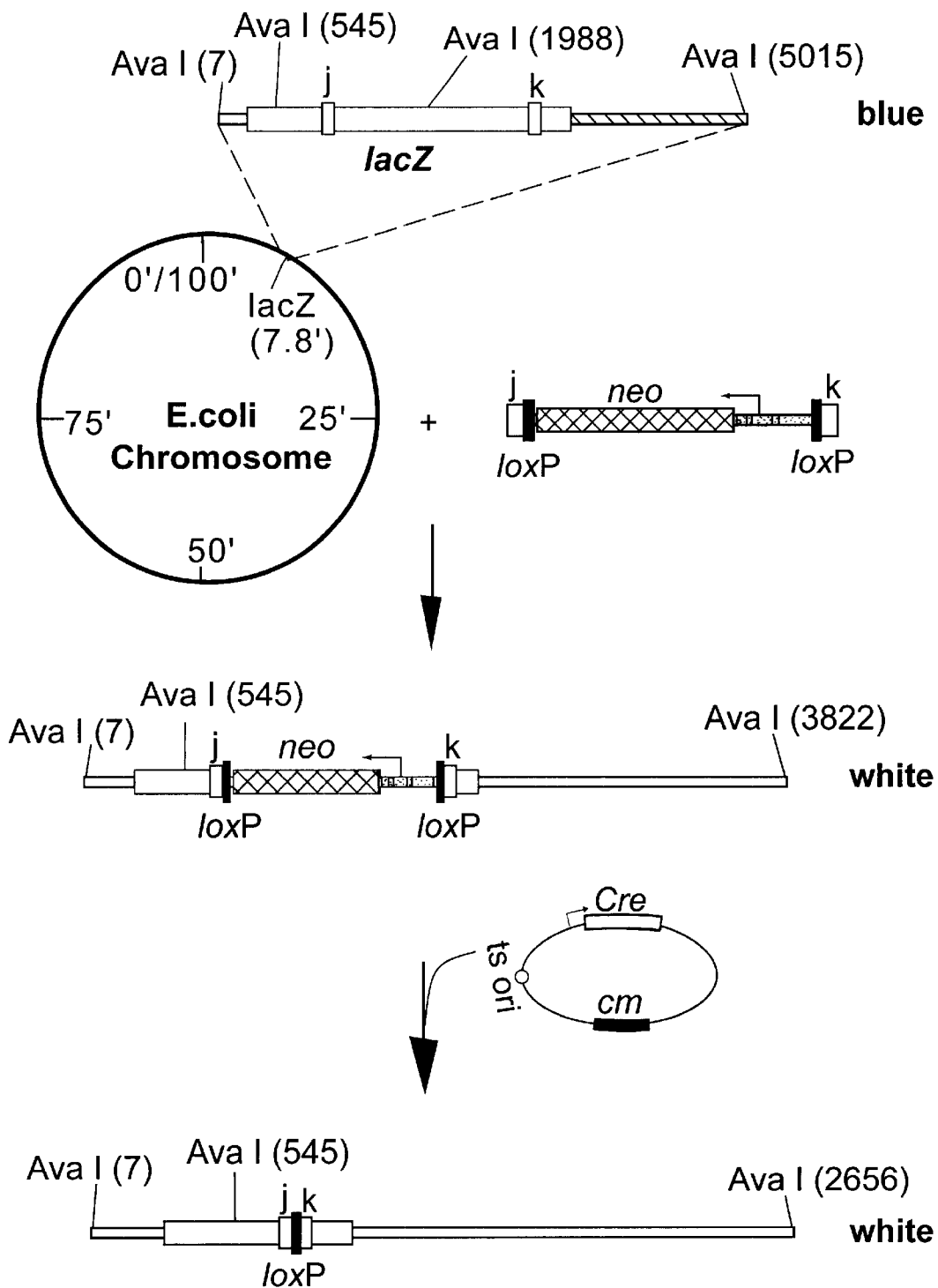
Figure 9B:
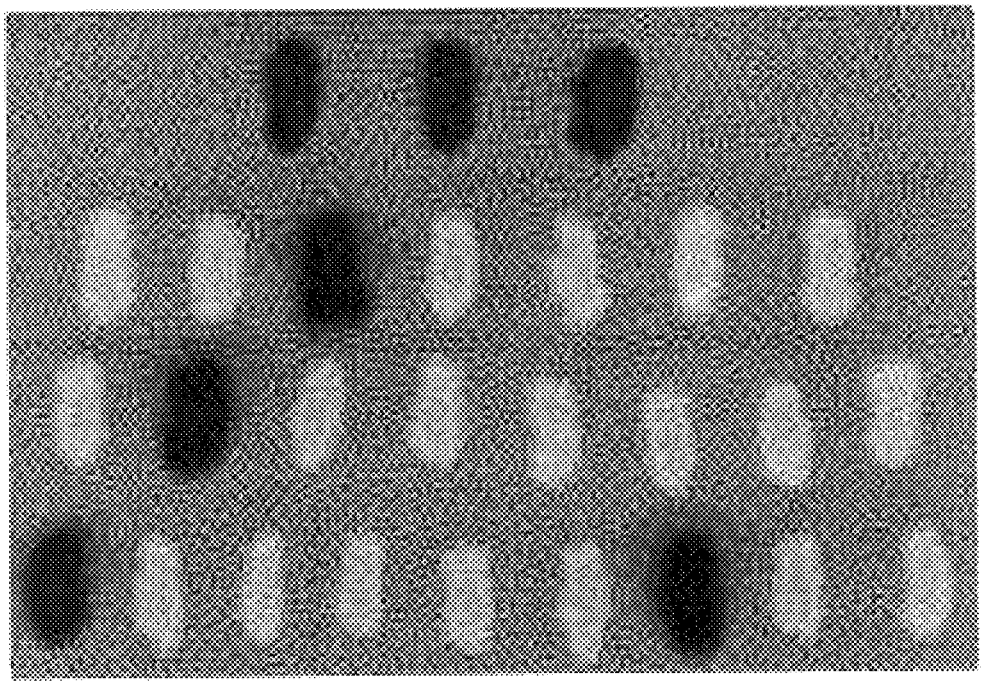
Figure 9C:
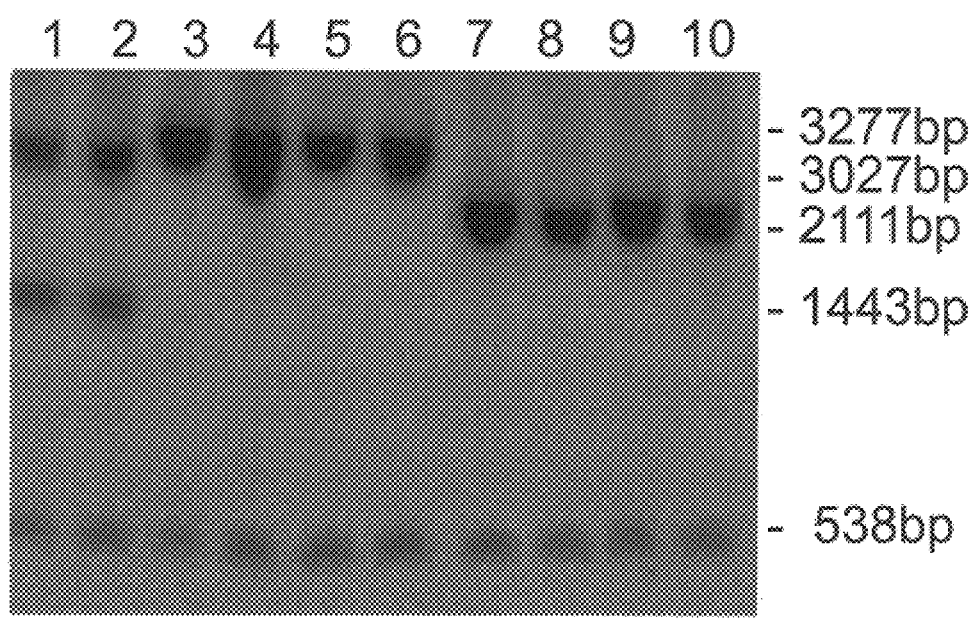

FIG. 9 Manipulation of the *E. coli* chromosome. FIG. 9a depicts the scheme of the recombination reactions. The endogenous lacZ gene of JC9604 at 7.8' of the *E. coli* chromosome, shown in expanded form with relevant Ava I sites and coordinates, was targeted by a PCR fragment that contained the neo gene flanked by homology arms j and k, and loxP sites, as depicted. Integration of the neo gene removed most of the lacZ gene including an Ava I site to alter the 1443 and 3027 bp bands into a 3277 bp band. In a second step, the neo gene was removed by Cre recombination between the loxPs by transient transformation of a Cre expression plasmid based on the pSC101 temperature-sensitive origin (ts ori). Removal of the neo gene by Cre recombinase reduces the 3277 band to 2111 bp. FIG. 9b shows β-galactosidase expression evaluated by streaking colonies on X-Gal plates. The top row of three streaks show β-galactosidase expression in the host JC9604 strain (w.t.), the lower three rows (Km) show 24 independent primary colonies, 20 of which display a loss of β-galactosidase expression indicative of the intended recombination event. FIG. 9c shows the results from Southern analysis of *E. coli* chromosomal DNA digested with Ava I using a random primed probe made from the entire lacZ coding region; lanes 1,2, w.t.; lanes 3–6, four independent white colonies after integration of the j–k neo gene; lanes 7–10; the same four colonies after transient transformation with the Cre expression plasmid.

Figure 10A:
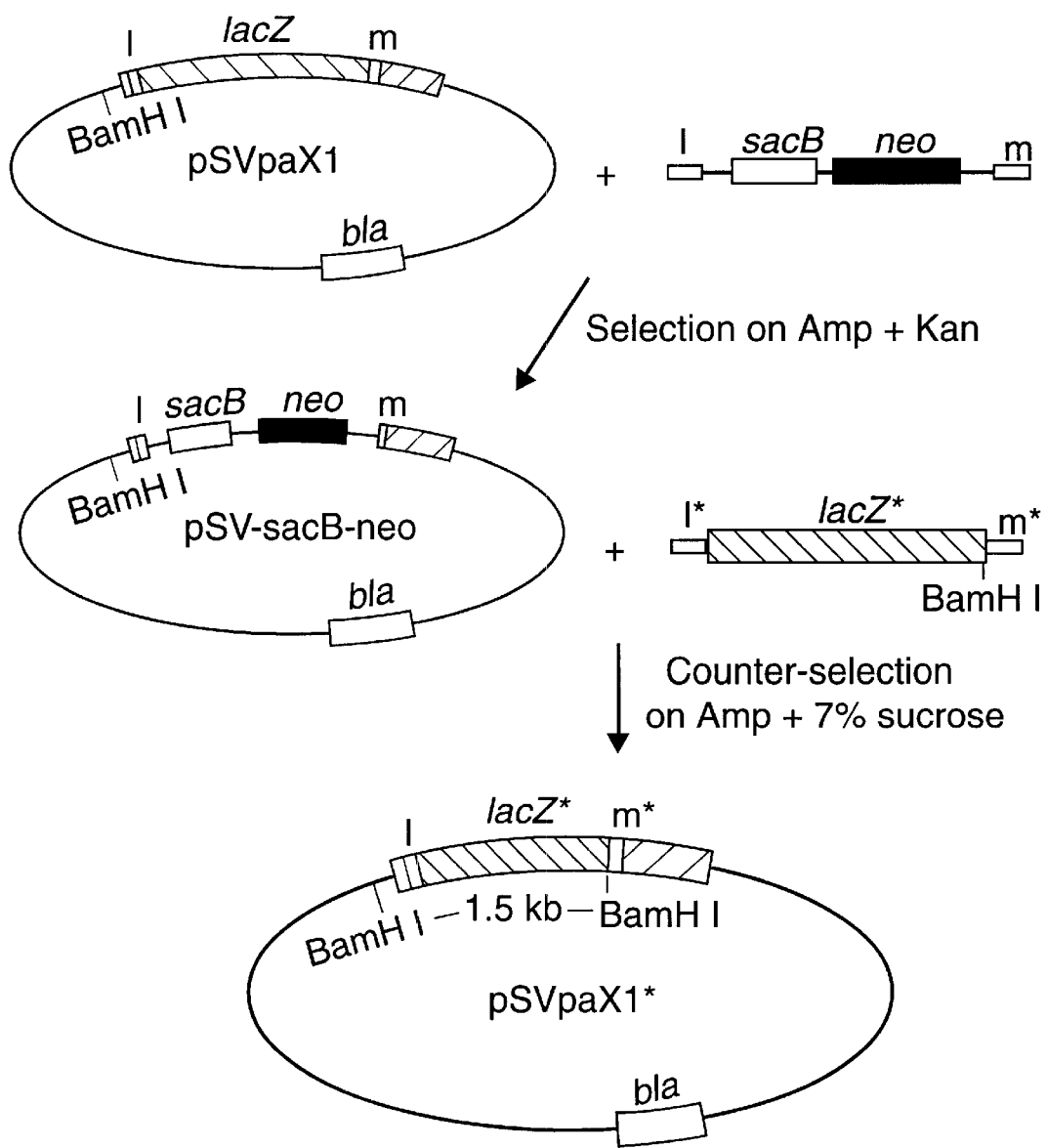
Figure 10B:
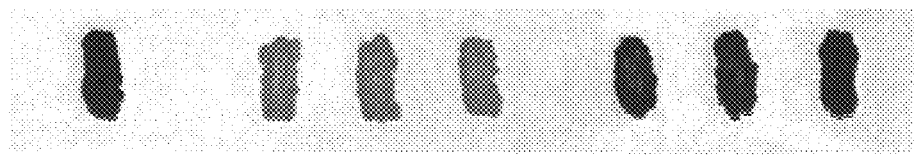
Figure 10C:
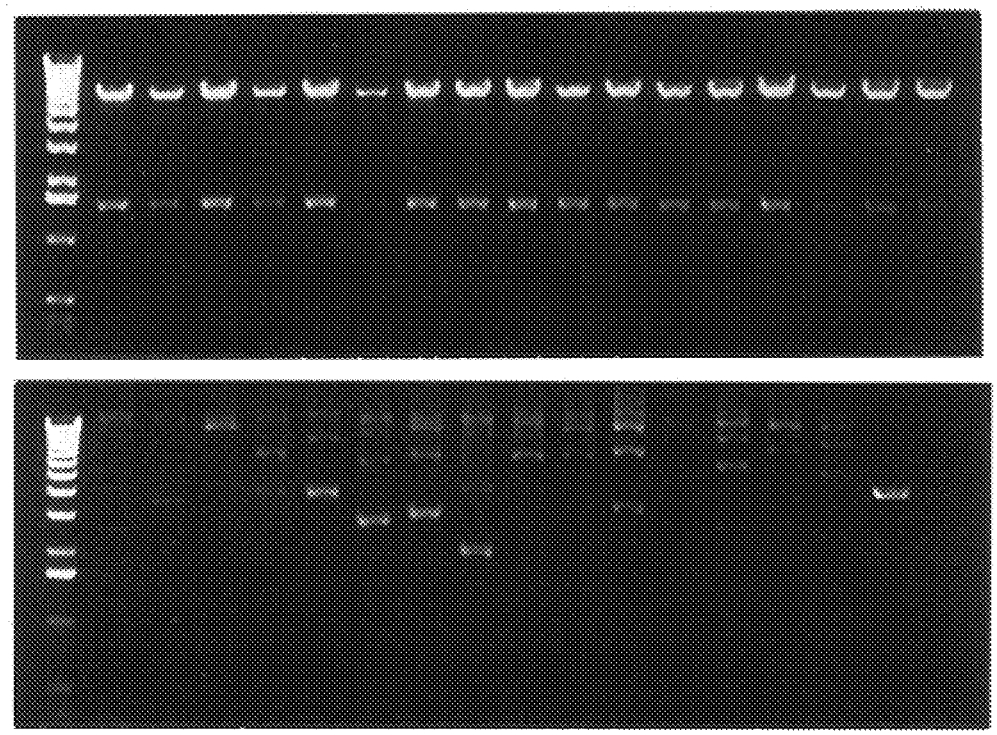

FIG. 10 Two rounds of ET cloning to introduce a point mutation. FIG. 10a depicts the scheme of the recombination reactions. The lacZ gene of pSVpaX1 was disrupted in JC9604lacZ, a strain made by the experiment of FIG. 9 to ablate endogenous lacZ expression and remove competitive sequences, by a sacB-neo gene cassette, synthesized by PCR to pIB279 and flanked by l and m homology arms. The recombinants, termed pSV-sacB-neo, were selected on Amp+Kan plates. The lacZ gene of pSV-sacB-neo was then repaired by a PCR fragment made from the intact lacZ gene using l* and m* homology arms. The m* homology arm included a silent C to G change that created a BamH1 site. The recombinants, termed pSVpaX1*, were identified by counter selection against the sacB gene using 7% sucrose. FIG. 10b shows that β-galactosidase expression from pSVpaX1 was disrupted in pSV-sacB-neo and restored in pSVpaX1*. Expression was analyzed on X-gal plates. Three independent colonies of each pSV-sacB-neo and pSVpaX1* are shown. FIG. 10c shows Ethidium bromide stained agarose gels of BamH1 digested DNA prepared from independent colonies taken after counter selection with sucrose. All β-galactosidase expressing colonies (blue) contained the introduced BamH1 restriction site (upper panel). All white colonies displayed large rearrangements and no product carried the diagnostic 1.5 kb BamH1 restriction fragment (lower panel).

FIG. 11 Transferance of ET cloning into a recBC+ host to modify a large episome. FIG. 11a depicts the plasmid, pBAD-ETγ, which carries the mobile ET system, and the strategy employed to target the Hoxa P1 episome. pBAD-ETγ is based on pBAD24 and includes (i) the truncated recE gene (t-recE) under the arabinose-inducible $P_{BAD}$ promoter; (ii) the recT gene under the EM7 promoter; and (iii) the redγ gene under the Tn5 promoter. It was transformed into NS3145, a recA *E. coli* strain which contained the Hoxa P1 episome. After arabinose induction, competent cells were prepared and transformed with a PCR product carrying the chloramphenicol resistance gene (cm) flanked by n and p homology arms. n and p were chosen to recombine with a segment of the P1 vector. FIG. 11b shows the results from Southern blots of Pvu II digested DNAs hybridized with a probe made from the P1 vector to visualize the recombination target site (upper panel) and a probe made from the chloramphenicol resistance gene (lower panel). Lane 1, DNA prepared from cells harboring the Hoxa P1 episome before ET cloning. Lanes 2–17, DNA prepared from 16 independent chloramphenicol resistant colonies.

Figure 12:
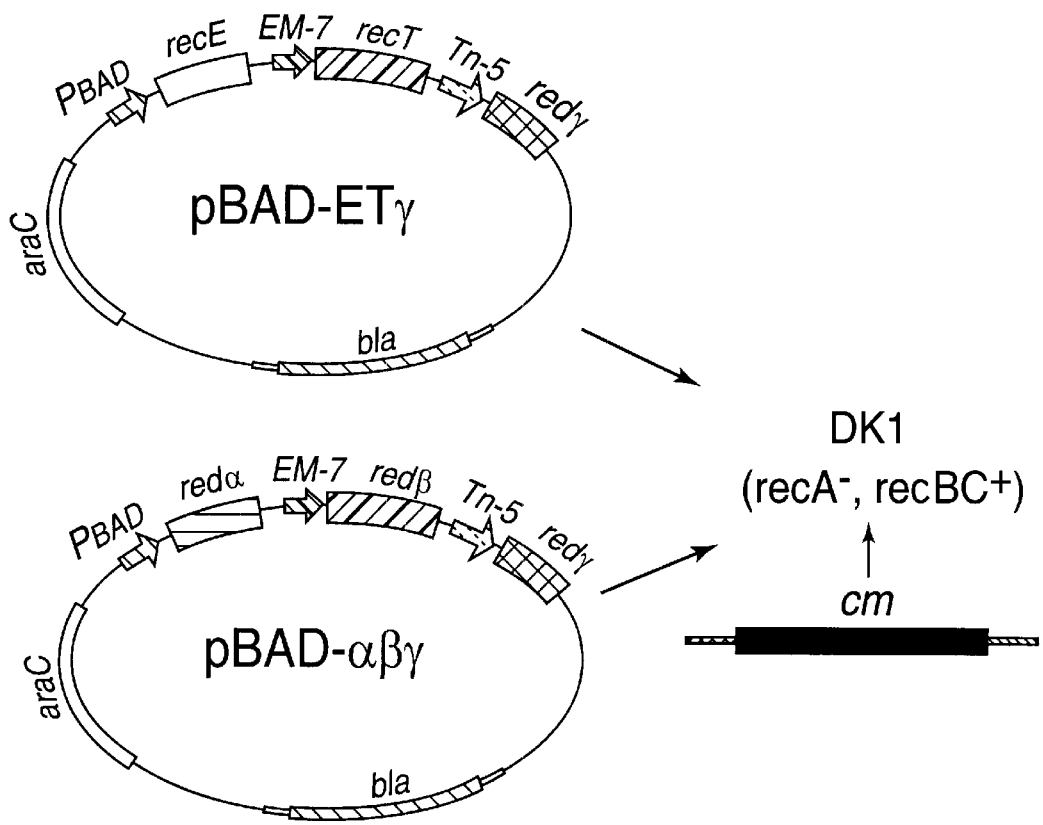
Figure 12:
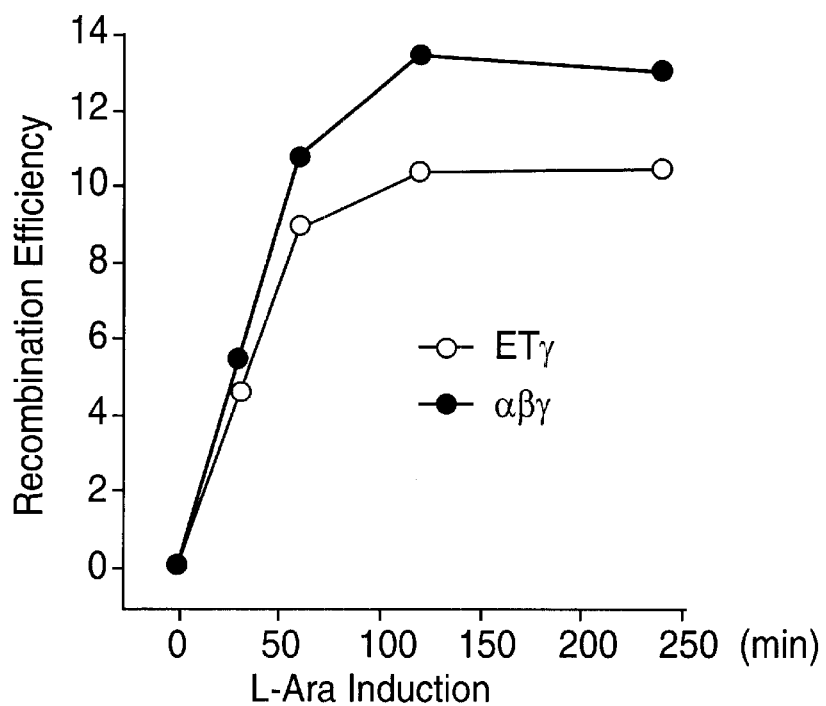

FIG. 12 Comparison of ET cloning using the recE/recT genes in pBAD-ETγ with redα/redβ genes in pBAD-αβγ.

The plasmids pBAD-ETγ or pBAD-αβγ, depicted, were transformed into the *E. coli* recA–, recBC+ strain, DK1 and targeted by a chloramphenicol gene as described in FIG. 6 to evaluate ET cloning efficiencies. Arabinose induction of protein expression was for 1 hour.

FIG. 13A The plasmid pBAD-ETγ is shown by diagram.

FIG. 13B The nucleic acid sequence and the protein coding portions of pBAD-ETγ are depicted.

Figure 14A:
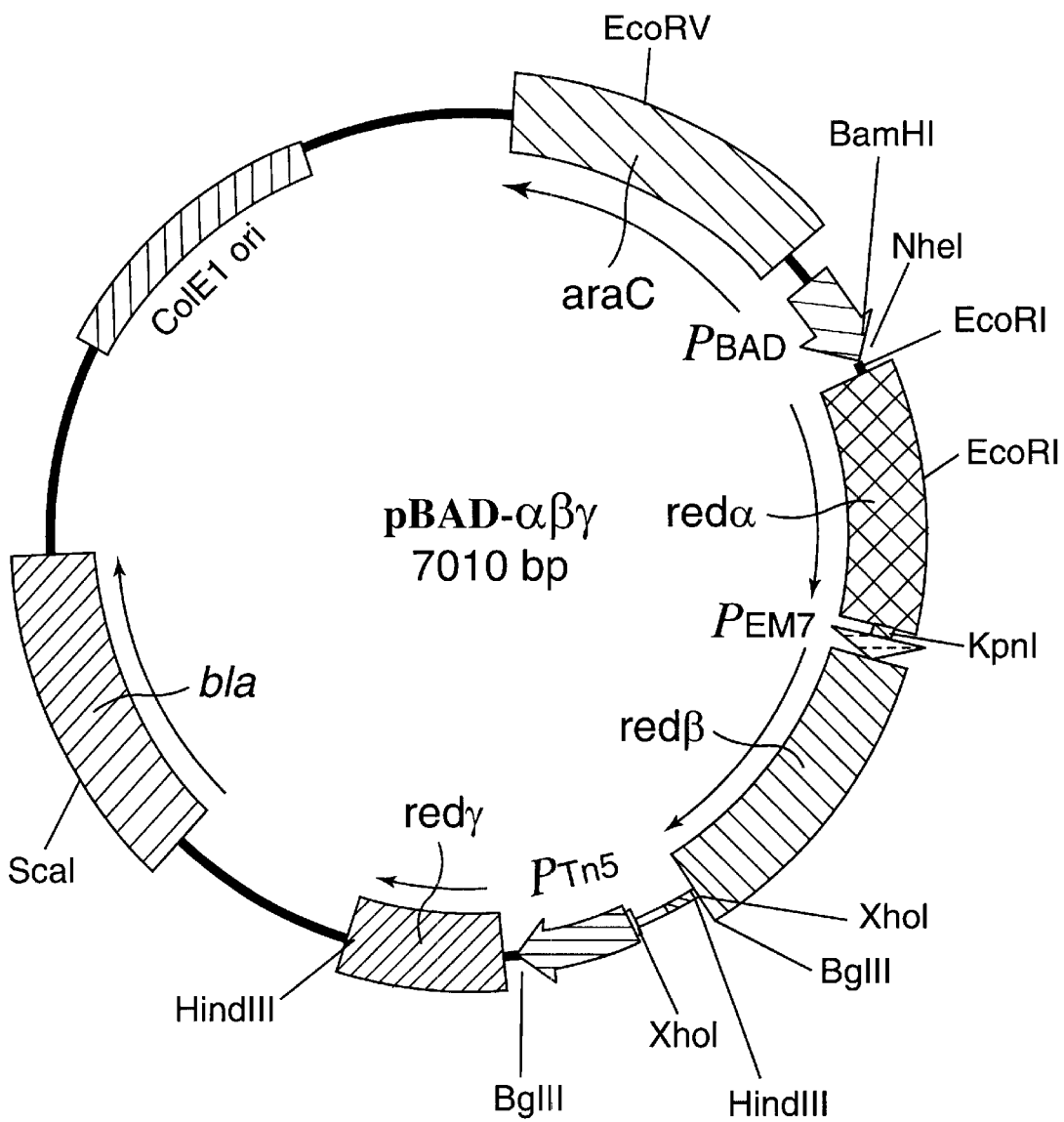

FIG. 14A The plasmid pBAD-αβγ is shown by diagram. This plasmid substantially corresponds to the plasmid shown in FIG. 13 except that the recE and recT genes are substituted by the redα and redβ genes.

FIG. 14B The nucleic acid sequence and the protein coding portions of pBAD-αβγ are depicted.

1. METHODS 1. 1 Preparation of Linear Fragments

Standard PCR reaction conditions were used to amplify linear DNA fragments.

The Tn5-neo gene from pJP5603 (Penfoid a nd Pemberton, Gene 118 (1992), 145–146) was amplified by using oligo pairs a/b and c/d. The chloramphenicol (cm) resistant gene from pMAK705 (Hashimoto-Gotoh and Sekiguchi, J.Bacteriol. 131 (1977), 405–412) was amplified by using primer pairs e/f and n/p. The Tn5-neo gene flanked by FRT or loxP sites was amplified from pKaZ or pKaX (http://www.embl-heidelberg.de/Externalinfo/stewart) using oligo pairs i/h, g/h and j/k. The sacB-neo cassette from plB279 (Blomfield etal., Mol.Microbiol. 5 (1991), 1447–1457) was amplified by using oligo pair l/m. The lacZ gene fragment from pSVpaZ11 (Buchholz et al., Nucleic Acids Res. 24 (1 996), 4256–4262) was amplified using oligo pair l*/m*. PCR products were purified using the QlAGEN PCR Purification Kit and eluted with $H_2O_2$, followed by digestion of any residual template DNA with Dpn I. After digestion, PCR products were extracted once with Phenol:$CHCl_3$, ethanol precipitated and resuspended in $H_2O$ at approximately 0.5 µg/µl.

1.2 Preparation of Competent Cells and Electroporation

Saturated overnight cultures were diluted 50 fold into LB medium, grown to an OD600 of 0.5, following by chilling on ice for 15 min. Bacterial cells were centrifuged at 7,000 rpm for 10 min at 0° C. The pellet was resuspended in ice-cold 10% glycerol and centrifuged again (7,000 rpm, –5° C., 10 min). This was repeated twice more and the cell pellet was suspended in an equal volume of ice-cold 10% glycerol. Aliquots of 50 µl were frozen in liquid nitrogen and stored at –80° C. Cells were thawed on ice and 1 µl DNA solution (containing, for co-transformation, 0.3 µg plasmid and 0.2 µg PCR products; or, for transformation, 0.2 µg PCR products) was added. Electroporation was performed using ice-cold cuvettes and a Bio-Rad Gene Pulser set to 25 µFD, 2.3 kV with Pulse Controller set at 200 ohms. LB medium (1 ml) was added after electroporation. The cells were incubated at 37° C. for 1 hour with shaking and then spread on antibiotic plates.

1.3 Induction of RecE and RecT Expression *E. coli* JC5547 carrying pBAD24-recET was cultured overnight in LB medium plus 0.2% glucose, 100 µg/ml ampicillin. Five parallel LB cultures, one of which (0) included 0.2% glucose, were started by a 1/100 inoculation. The cultures were incubated at 37° C. with shaking for 4 hours and 0.1% L-arabinose was added 3, 2, 1 or ½ hour before harvesting and processing as above. Immediately before harvesting, 100 µl was removed for analysis on a 10% SDS-polyacrylamide gel. *E. coli* NS3145 carrying Hoxa-P1 and pBAD-ETγ was induced by 0.1% L arabirose for 90 min before harvesting.

1.4 Transient Transformation of FLP and Cre Expression Plasmids

The FLP and Cre expression plasmids, 705-Cre and 705-FLP (Buchholz et al, Nucleic Acids Res. 24 (1996), 3118–3119), based on the pSC101 temperature sensitive origin, were transformed into rubidium chloride competent bacterial cells. Cells were spread on 25 µg/ml chloramphenicol plates, and grown for 2 days at 30° C., whereupon colonies were picked, replated on L-agar plates without any antibiotics and incubated at 40° C. overnight. Single colonies were analyzed on various antibiotic plates and all showed the expected loss of chloramphenicol and kanamycin resistance.

1.5 Sucrose Counter Selection of SacB Expression

The *E. coli* JC9604lacZ strain, generated as described in FIG. 11, was cotransformed with a sacB-neo PCR fragment and pSVpaX1 (Buchholz et al, Nucleic Acids Res. 24 (1996), 4256–4262). After selection on 100 µg/ml ampicillin, 50 µg/ml kanamycin plates, pSVpaX-sacB-neo plasmids were isolated and cotransformed into fresh JC9604lacZ cells with a PCR fragment amplified from pSVpaX1 using primers l*/m*. Oligom carried a silent point mutation which generated a BamHI site. Cells were plated on 7% sucrose, 100 µg/ml ampicillin, 40 µg/ml X-gal plates and incubated at 28° C. for 2 days. The blue and white colonies grown on sucrose plates were counted and further checked by restriction analysis.

1.6 Other Methods

DNA preparation and Southern analysis were performed according to standard procedures. Hybridization probes were generated by random priming of fragments isolated from the Tn5 neo gene (PvuII), Hoxa3 gene (both HindIII fragments), lacZ genes (EcoR1 and BamH1 fragments from pSVpaX1), cm gene (BstB1 fragments from pMAK705) and P1 vector fragments (2.2 kb EcoR1 fragments from P1 vector).

2. RESULTS 2.1 Identification of recombination events in *E. coli*

To identify a flexible homologous recombination reaction in *E. coli*, an assay based on recombination between linear and circular DNAs was designed (FIG. 1, FIG. 3). Linear DNA carrying the Tn5 kanamycin resistance gene (neo) was made by PCR (FIG. 3a). Initially, the oligonucleotides used for PCR amplification of neo were 60 mers consisting of 42 nucleotides at their 5' ends identical to chosen regions in the plasmid and, at the 3' ends, 18 nucleotides to serve as PCR primers. Linear and circular DNAs were mixed in equimolar proportions and co-transformed into a variety of *E. coli* hosts. Homologous recombination was only detected in sbcA *E. coli* hosts. More than 95% of double ampicillin/kanamycin resistant colonies (FIG. 3b) contained the expected homologously recombined plasmid as determined by restriction digestion and sequencing. Only a low background of kanamycin resistance, due to genomic integration of the neo gene, was apparent (not shown).

Figure 3A:
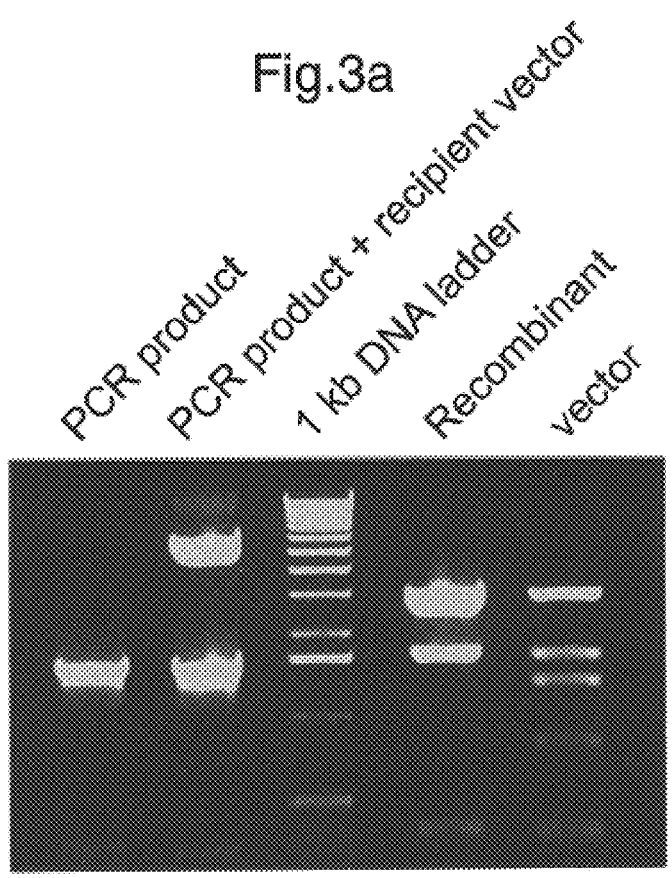
Figure 3B:
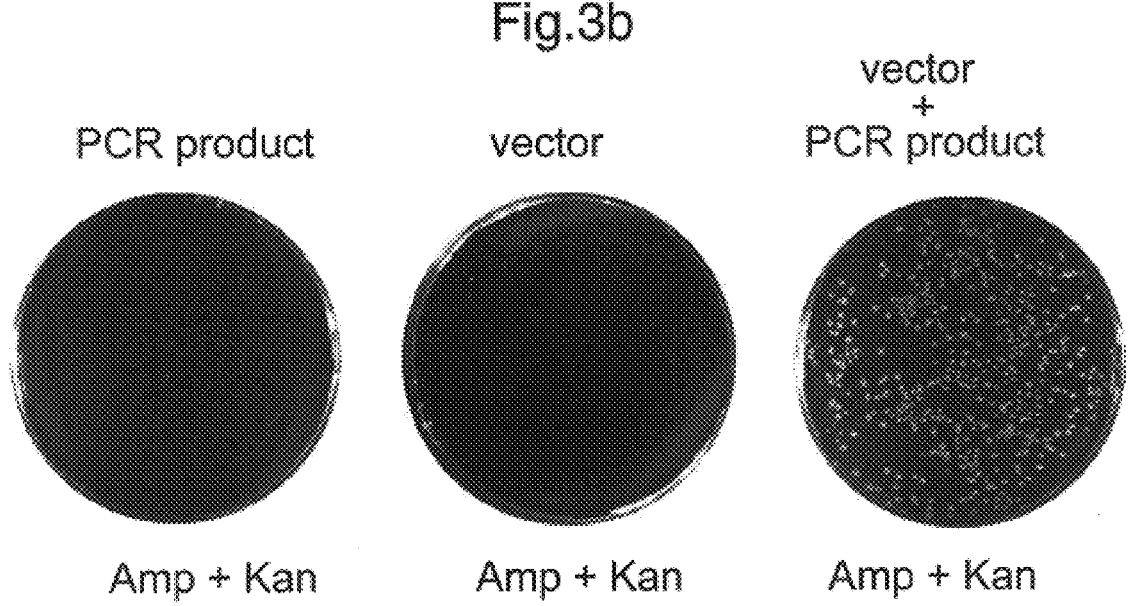
Figure 3C:
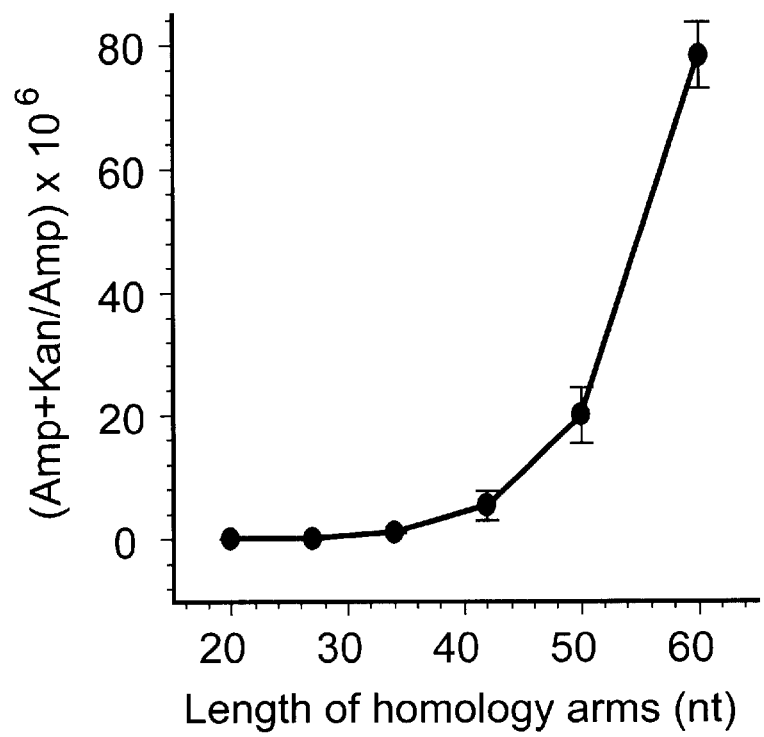
Figure 3D:
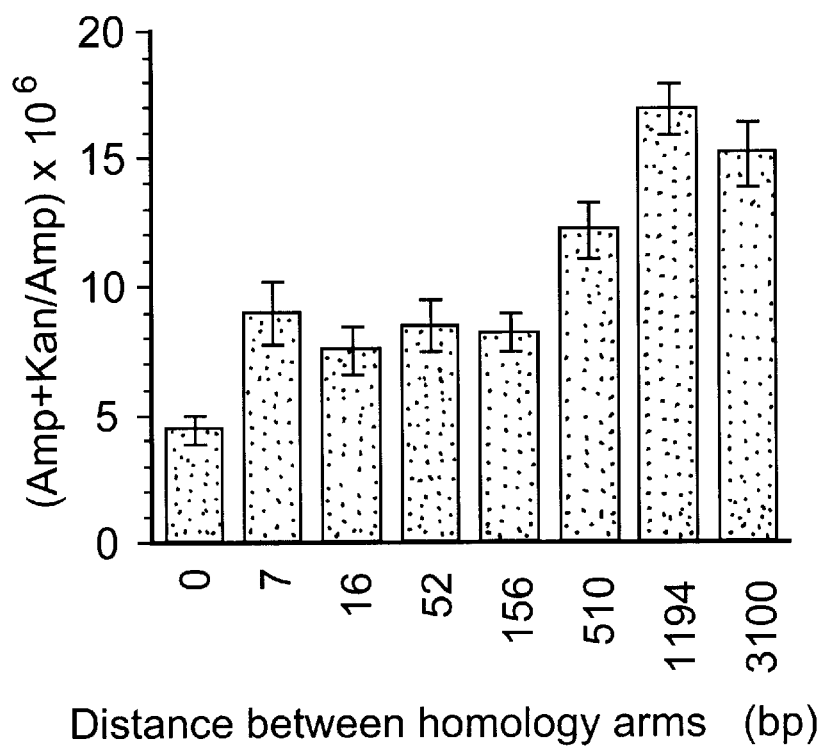

The linear plus circular recombination reaction was characterized in two ways. The relationship between homology arm length and recombination efficiency was simple, with longer arms recombining more efficiently (FIG. 3c). Efficiency increased within the range tested, up to 60 bp. The effect of distance between the two chosen homology sites in the recipient plasmid was examined (FIG. 3d). A set of eight PCR fragments was generated by use of a constant left homology arm with differing right homology arms. The right homology arms were chosen from the plasmid sequence to be 0–3100 bp from the left. Correct products were readily obtained from all, with less than 4 fold difference between them, although the insertional product (0) was least efficient. Correct products also depended on the presence of both homology arms, since PCR fragments containing only one arm failed to work.

2.2 Involvement of RecE and RecT

The relationship between host genotype and this homologous recombination reaction was more systematically examined using a panel of *E. coli* strains deficient in various recombination components (Table 1).

Table 1 Only the two sbcA strains, JC8679 and JC9604 presented the intended recombination products and RecA was not required. In sbcA strains, expression of RecE and RecT is activated. Dependence on recE can be inferred from comparison of JC8679 with JC8691. Notably no recombination products were observed in JC9387 suggesting that the sbcBC background is not capable of supporting homologous recombination based on 50 nucleotide homology arms.

Figure 6A:
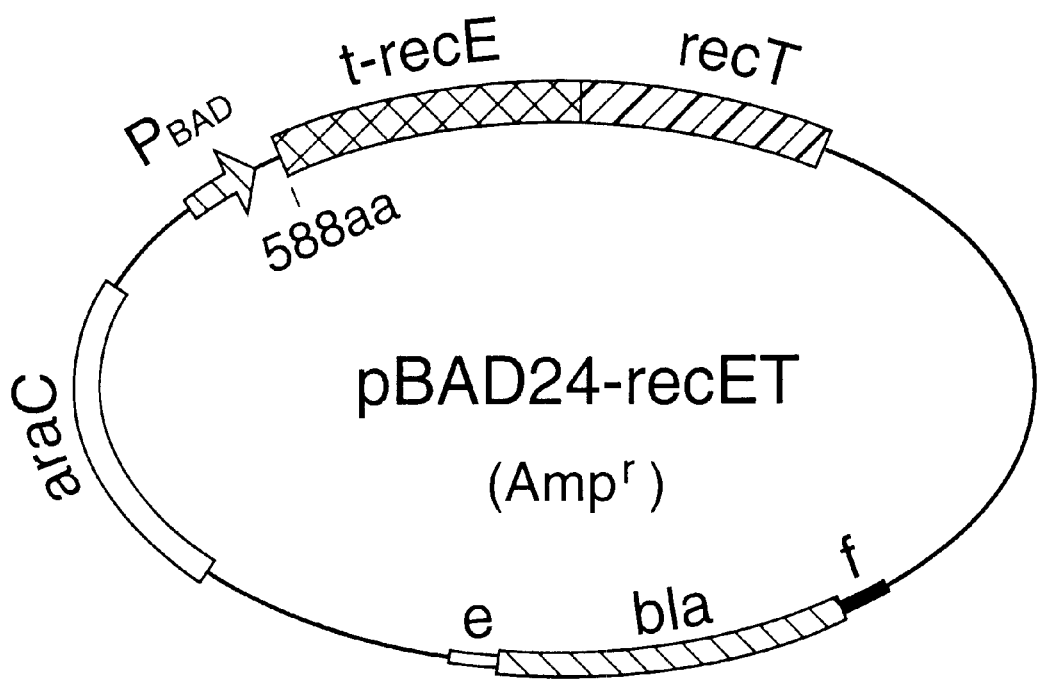
Figure 6A:
Figure 6A:
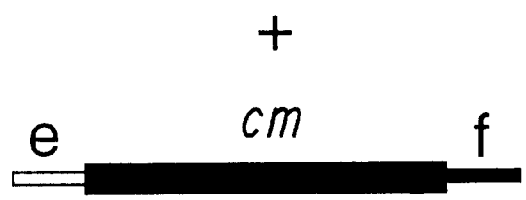
Figure 6B:
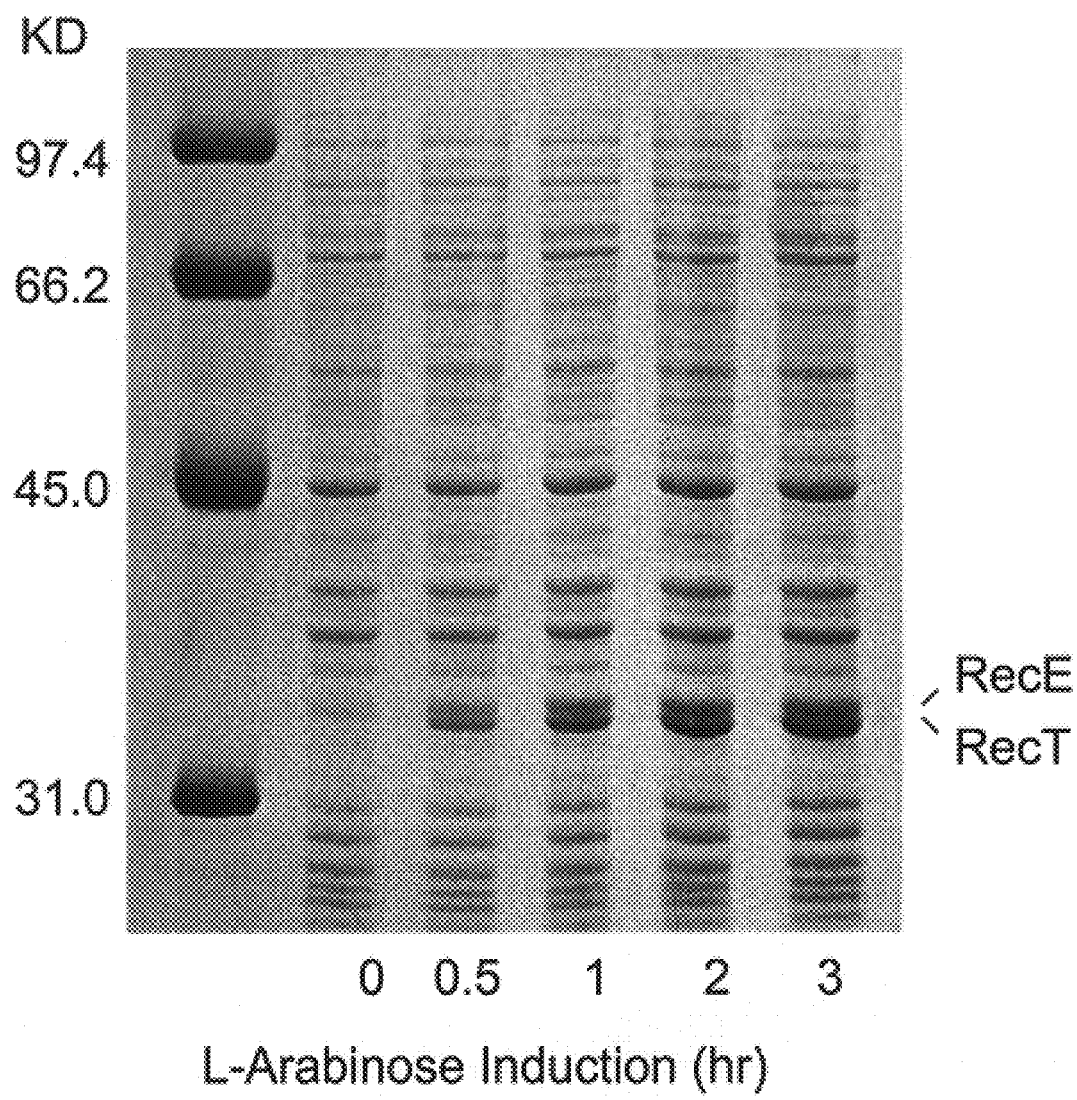
Figure 6C:
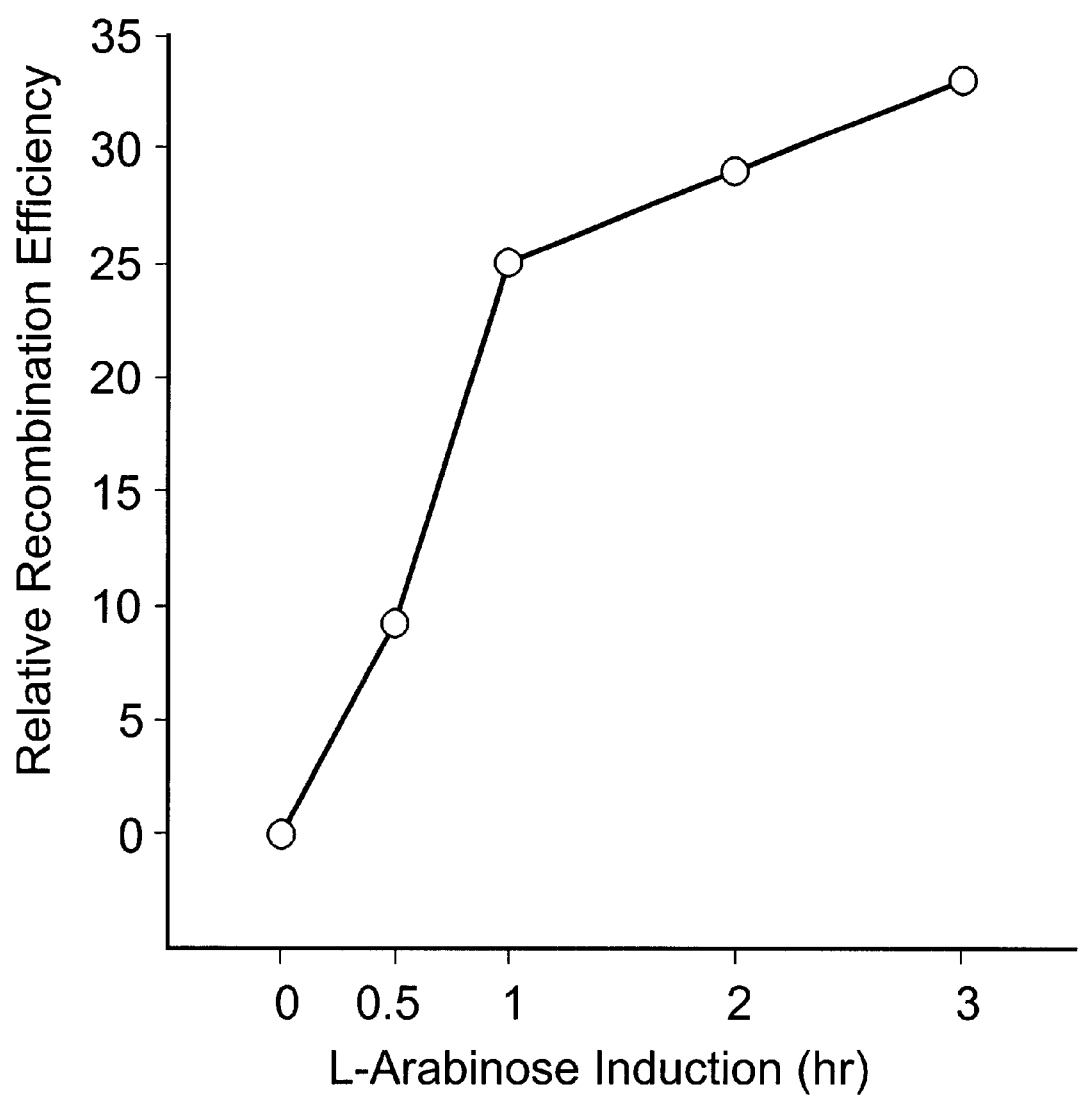

To demonstrate that RecE and RecT are involved, part of the recET operon was cloned into an inducible expression vector to create pBAD24-recET (FIG. 6a). the recE gene was truncated at its N-terminal end, as the first 588 a.a.s of RecE are dispensable. The recBC strain, JC5547, was transformed with pBAD24-recET and a time course of RecE/RecT induction performed by adding arabinose to the culture media at various times before harvesting for competent cells. The batches of harvested competent cells were evaluated for protein expression by gel electrophoresis (FIG. 6b)

and for recombination between a linear DNA fragment and the endogenous pBAD24-recET plasmid (FIG. 6c). Without induction of RecE/RecT, no recombinant products were found, whereas recombination increased in approximate concordance with increased RecE/RecT expression. This experiment also shows that co-transformation of linear and circular DNAs is not essential and the circular recipient can be endogenous in the host. From the results shown in FIGS. 3, 6 and Table 2, we conclude that RecE and RecT mediate a very useful homologous recombination reaction in recBC E. coli at workable frequencies. Since RecE and RecT are involved, we refer to this way of recombining linear and circular DNA fragments as "ET cloning".

2.3 Application of ET Cloning to Large Target DNAs

To show that large DNA episomes could be manipulated in E. coli, a >76 kb P1 clone that contains at least 59 kb of the intact mouse Hoxa complex, (confirmed by DNA sequencing and Southern blotting), was transferred to an E. coli strain having an sbcA background (JC9604) and subjected to two rounds of ET cloning. In the first round, the Tn903 kanamycin resistance gene resident in the P1 vector was replaced by an ampicillin resistance gene (FIG. 4). In the second round, the interval between the Hoxa3 and a4 genes was targeted either by inserting the neo gene between two base pairs upstream of the Hoxa3 proximal promoter, or by deleting 6203 bp between the Hoxa3 and a4 genes (FIG. 8a). Both insertional and deletional ET cloning products were readily obtained (FIG. 8b, lanes 2, 3 and 5) showing that the two rounds of ET cloning took place in this large E. coli episome with precision and no apparent unintended recombination.

The general applicability of ET cloning was further examined by targeting a gene in the E. coli chromosome (FIG. 9a). The β-galactosidase (lacZ) gene of JC9604 was chosen so that the ratio between correct and incorrect recombinants could be determined by evaluating β-galactosidase expression. Standard conditions (0.2 µg PCR fragment; 50 µl competent cells), produced 24 primary colonies, 20 of which were correct as determined by β-galactosidase expression (FIG. 9b), and DNA analysis (FIG. 9c, lanes 3–6).

2.4 Secondary Recombination Reactions to Remove Operational Sequences

The products of ET cloning as described above are limited by the necessary inclusion of selectable marker genes. Two different ways to use a further recombination step to remove this limitation were developed. In the first way, site specific recombination mediated by either Flp or Cre recombinase was employed. In the experiments of FIGS. 8 and 9, either Flp recombination target sites (FRTs) or Cre recombination target sites (loxPs) were included to flank the neo gene in the linear substrates. Recombination between the FRTs or loxPs was accomplished by Flp or Cre, respectively, expressed from plasmids with the pSC101temperature sensitive replication origin (Hashimoto-Gotoh and Sekiguchi, J.Bacteriol. 131 (1977), 405–412) to permit simple elimination of these plasmids after site specific recombination by temperature shift. The precisely recombined Hoxa P1 vector was recovered after both ET and Flp recombination with no other recombination products apparent (FIG. 8, lanes 4 and 6). Similarly, Cre recombinase precisely recombined the targeted lacZ allele (FIG. 9, lanes 7–10). Thus site specific recombination can be readily coupled with ET cloning to remove operational sequences and leave a 34 bp site specific recombination target site at the point of DNA manipulation.

In the second way to remove the selectable marker gene, two rounds of ET cloning, combining positive and counter selection steps, were used to leave the DNA product free of any operational sequences (FIG. 10a).

Figure 5B:
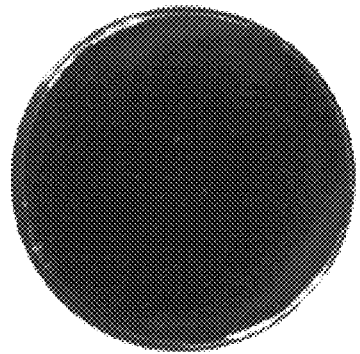
Figure 5B:
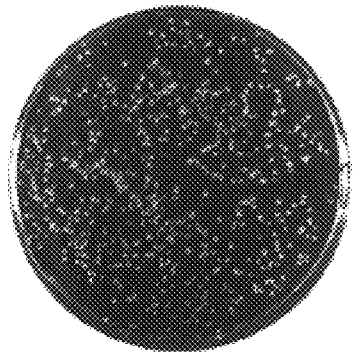

Additionally this experiment was designed to evaluate, by a functional test based on β-galactosidase activity, whether ET cloning promoted small mutations such as frame shift or point mutations within the region being manipulated. In the first round, the lacZ gene of pSVpaX1 was disrupted with a 3.3 kb PCR fragment carrying the neo and B.subtilis sacB (Blomfield et al., Mol.Microbiol. 5 (1991), 1447–1457) genes, by selection for kanamycin resistance (FIG. 10a). As shown above for other positively selected recombination products, virtually all selected colonies were white (FIG. 10b), indicative of successful lacZ disruption, and 17 of 17 were confirmed as correct recombinants by DNA analysis. In the second round, a 1.5 kb PCR fragment designed to repair lacZ was introduced by counter selection against the sacB gene. Repair of lacZ included a silent point mutation to create a BamHI restriction site. Approximately one quarter of sucrose resistant colonies expressed β-galactosidase, and all analyzed (17 of 17; FIG. 10c) carried the repaired lacZ gene with the BamH1 point mutation. The remaining three quarters of sucrose resistant colonies did not express β-galactosidase, and all analyzed (17 of 17; FIG. 10c) had undergone a variety of large mutational events, none of which resembled the ET cloning product. Thus, in two rounds of ET cloning directed at the lacZ gene, no disturbances of β-galactosidase activity by small mutations were observed, indicating the RecE/RecT recombination works with high fidelity. The significant presence of incorrect products observed in the counter selection step is an inherent limitation of the use of counter selection, since any mutation that ablates expression of the counter selection gene will be selected. Notably, all incorrect products were large mutations and therefore easily distinguished from the correct ET product by DNA analysis. In a different experiment (FIG. 5), we observed that ET cloning into pZero2.1 (InVitroGen) by counter selection against the ccdB gene gave a lower background of incorrect products (8%), indicating that the counter selection background is variable according to parameters that differ from those that influence ET cloning efficiencies.

2.5 Transference of ET Cloning Between E. coli Hosts

Figure 11A:
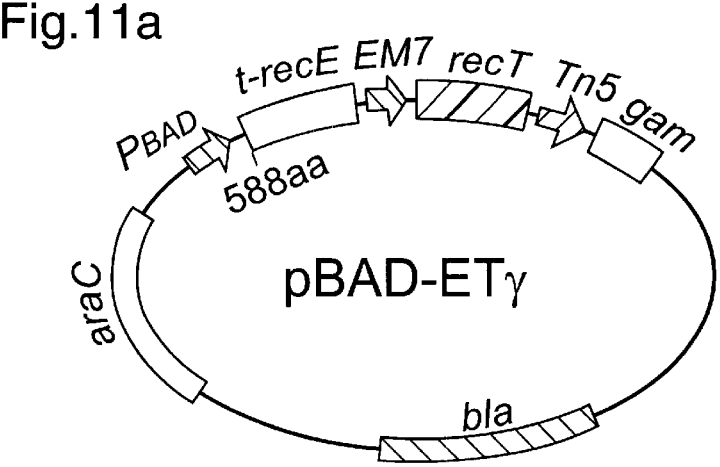
Figure 11A:
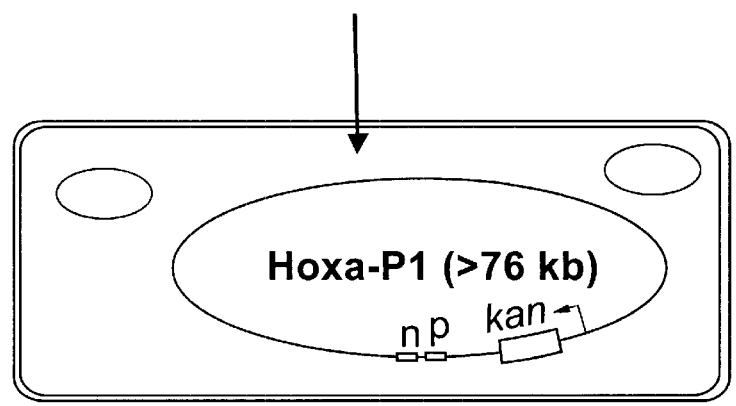
Figure 11A:
Figure 11A:
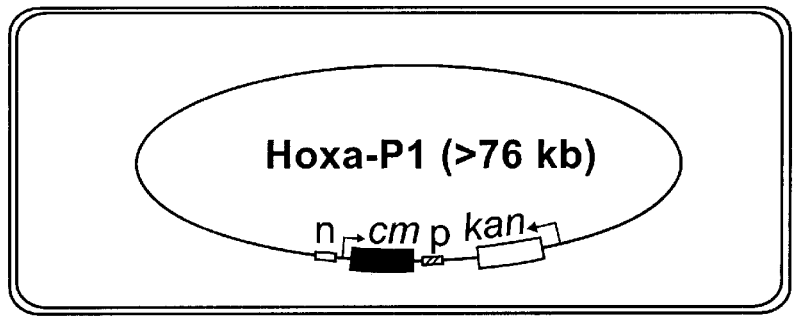
Figure 11B:
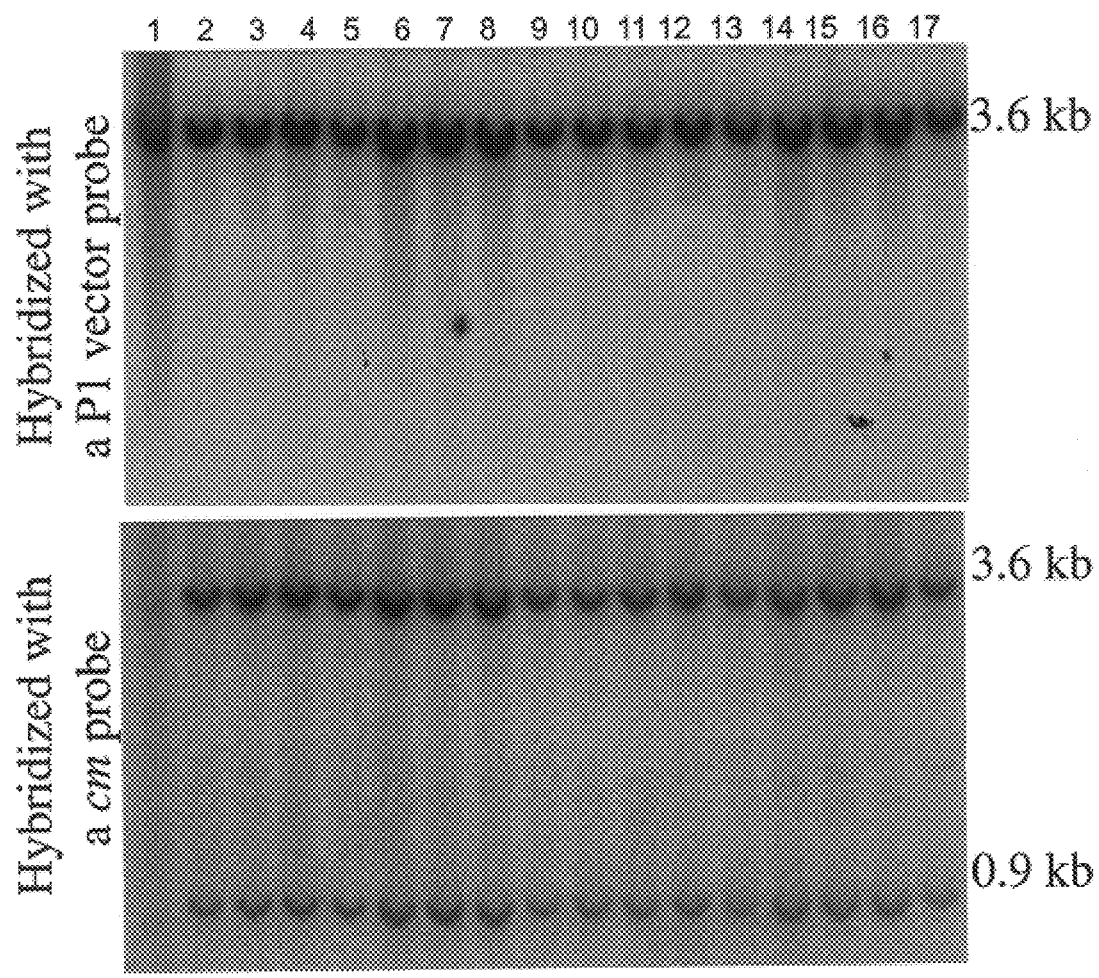

The experiments shown above were performed in recBC– E. coli hosts since the sbcA mutation had been identified as a suppressor of recBC (Barbour et al., Proc.Natl.Acad.Sci. USA 67 (1970), 128–135; Clark, Genetics 78 (1974), 259–271). However, many useful E. coli strains are recBC+, including strains commonly used for propagation of P1, BAC or PAC episomes. To transfer ET cloning into recBC+ strains, we developed pBAD-ETγ and pBAD-αβγ (FIGS. 13 and 14). These plasmids incorporate three features important to the mobility of ET cloning. First, RecBC is the major E. coli exonuclease and degrades introduced linear fragments. Therefore the RecBC inhibitor, Redγ (Murphy, J.Bacteriol. 173 (1991), 5808–5821), was included. Second, the recombinogenic potential of RecE/RecT, or Redα/Redβ3, was regulated by placing recE or redα under an inducible promoter. Consequently ET cloning can be induced when required and undesired recombination events which are restricted at other times. Third, we observed that ET cloning efficiencies are enhanced when RecT, or Redβ, but not RecE, or Redα, is overexpressed. Therefore we placed recT, or redβ, under the strong, constitutive, EM7 promoter.

pBAD-ETγ was transformed into NS3145 E. coli harboring the original Hoxa P1 episome (FIG. 11a). A region in the P1 vector backbone was targeted by PCR amplification of the chloramphenicol resistance gene (cm) flanked by n and p homology arms. As described above for positively selected ET cloning reactions, most (<90%) chloramphenicol resistant colonies were correct. Notably, the overall efficiency of ET cloning, in terms of linear DNA transformed, was nearly three times better using pBAD-ETγ than with similar experiments based on targeting the same episome in the sbcA host, JC9604. This is consistent with our observation that overexpression of RecT improves ET cloning efficiencies.

A comparison between ET cloning efficiencies mediated by RecE/RecT, expressed from pBAD-ETγ, and Redα/Redβ, expressed from pBAD-αβγ was made in the recA–, recBC+ E. coli strain, DK 1 (FIG. 12). After transformation of E. coli DK1 with either pBAD-ETγ or pBAD-αβγ, the same experiment as described in FIGS. 6a,c, to replace the bla gene of the pBAD vector with a chloramphenicol gene was performed. Both pBAD-ETγ or pBAD-αβγ presented similar ET cloning efficiencies in terms of responsiveness to arabinose induction of RecE and Redα, and number of targeted events.

TABLE 1

| E.coli Strains | Genotypes | Amp + Kan | Amp × $10^8$/μg |
|---|---|---|---|
| JC8679 | recBC sbcA | 318 | 2.30 |
| JC9604 | recA recBC sbcA | 114 | 0.30 |
| JC8691 | recBC sbcA recE | 0 | 0.37 |
| JC5547 | recA recBC | 0 | 0.37 |
| JC5519 | recBC | 0 | 1.80 |
| JC15329 | recA recBC sbcBC | 0 | 0.03 |
| JC9387 | recBC sbcBC | 0 | 2.20 |
| JC8111 | recBC sbcBC recF | 0 | 2.40 |
| JC9366 | recA | 0 | 0.37 |
| JC13031 | recJ | 0 | 0.45 |

What is claimed is:

1. A method for cloning DNA molecules in procaryotic cells comprising the steps of:
   a) providing a procaryotic host cell capable of performing homologous recombination,
   b) contacting in said host cell a circular first DNA molecule which is capable of being replicated in said host cell with a second DNA molecule comprising at least two regions of sequence homology to regions on the first DNA molecule, under conditions for promoting homologous recombination between said first and second DNA molecules, and
   c) selecting a host cell in which homologous recombination between said first and second DNA molecules has occurred,
   wherein a second DNA molecule is introduced into the host cell in a form which allows recombination without further modification, and wherein the homologous recombination occurs by recE and recT mediated gene recombination.

2. The method according to claim 1, wherein the host cell expresses recE and recT genes.

3. The method according to claim 2, wherein the recE and recT genes are selected from the group of consisting of *E. coli* recE, *E. coli* rect, phage λredα and phage λredβ.

4. method according to claim 2, wherein the host cell is transformed with at least one vector capable of expressing recE and/or recT genes.

5. method of claim 2, wherein the expression of the recE and/or recT genes is under control of a regulatable promoter.

6. method of claim 4, wherein the recT gene is overexpressed in comparison to the recE gene.

7. The method according to claim 2, wherein the recE gene is a nucleic acid molecule selected from the group consisting of:
   (a) the nucleic acid sequence from position 1320 (ATG) to 1998 (CGA) of SEQ ID No. 10, and,
   (b) a nucleic acid sequence which hybridizes under stringent conditions with the nucleic acid sequence of (a).

8. The method according to claim 2, wherein the recT gene is a nucleic acid molecule selected from the group consisting of:
   (a) the nucleic acid sequence from position 2086 (ATG) to 2868 (GCA) of SEQ ID No. 10, and,
   (b) a nucleic acid sequence which hybridizes under stringent conditions with the nucleic acid sequences of (a).

9. The method according to claim 1, wherein the host cell is a gram-negative bacterial cell.

10. The method according to claim 9, wherein the host cell is an *Escherichia coli* cell.

11. The method according to claim 10, wherein the host cell is an *Escherichia coli* K12 strain.

12. The method according to claim 11, wherein the *E. coli* strain is JC 8679 or JC 9604.

13. The method according to claim 1, wherein the host cell expresses a recBC inhibitor gene.

14. The method according to claim 13, wherein the host cell is transformed with a vector expressing the recBC inhibitor gene.

15. The method according to claim 13, wherein the recBC inhibitor gene is a nucleic acid molecule selected from the group consisting of:
   (a) the nucleic acid sequence from position 3588 (ATG) to 4002 (GTA) of SEQ ID No. 10, and,
   (b) a nucleic acid sequence which hybridizes under stringent conditions as defined above with the nucleic acid sequence of (a).

16. The method according to claim 12, wherein the host cell is a prokaryotic recBC+ cell.

17. The method according to claim 1, wherein the first DNA molecule is an extrachromosomal DNA molecule containing an origin of replication which is operative in the host cell.

18. The method according to claim 17, wherein the first DNA molecule is selected from the group consisting of plasmids, cosmids, P1 vectors, BAC vectors and PAC vectors.

19. The method according to claim 1, wherein the first DNA molecule is a host cell chromosome.

20. The method according to claim 1, wherein the second DNA molecule is linear.

21. The method according to claim 1, wherein the regions of sequence homology are at least 15 nucleotides each.

22. The method according to claim 1, wherein the second DNA molecule is obtained by an amplification reaction.

23. The method according to claim 1, wherein the first and/or second DNA molecules are introduced into the host cells by transformation.

24. The method according to claim 23, wherein the transformation method is electroporation.

25. The method according to claim 1, wherein the first and second DNA molecules are introduced into the host cell simultaneously by co-transformation.

26. The method according to claim 1, wherein the second DNA molecule is introduced into a host cell in which the first DNA molecule is already present.

27. The method according to claim 1, wherein the second DNA molecule contains at least one marker gene placed between the two regions of sequence homology and wherein homologous recombination is detected by expression of said marker gene.

28. The method according to claim 27, wherein the marker gene is selected from the group consisting of antibiotic resistance genes, deficiency complementation genes and reporter genes.

29. The method of claim 1, wherein the first DNA molecule contains at least one marker gene between the two regions of sequence homology and wherein homologous recombination is detected by lack of expression of said marker gene.

30. The method of claim 29, wherein said marker gene is a reporter gene or gene, which under selected conditions, conveys a toxic or bacteriostatic effect on the cell.

31. A method according to claim 1, wherein the first DNA molecule contains at least one target site for a site specific recombinase between the two regions of sequence homology and wherein homologous recombination is detected by removal of said target site.

32. A method for cloning DNA molecules comprising the steps of:
   (a) providing a source of RecE and RecT proteins,
   (b) contacting a circular first DNA molecule which is capable of being replicated in a suitable host cell with a second DNA molecule comprising at least two regions of sequence homology to regions on the first DNA molecule, under conditions for promoting homologous recombination between said first and second DNA molecules, and
   (c) selecting DNA molecules in which homologous recombination between said first and second DNA molecules has occurred, wherein a second DNA molecule is introduced into the host cell in a form which allows recombination without further modification, and wherein the homologous recombination occurs by recE- and recT-mediated gene recombination.

33. The method of claim 32, wherein said RecE and RecT proteins are selected from the group of proteins consisting of E. coli RecE, E. coli RecT, phage λRedα and phage λRedβ.

34. The method of claim 32, wherein the recombination occurs in vitro.

35. The method of claim 32, wherein the recombination occurs in vivo.

36. A method for making a recombinant DNA molecule comprising introducing into a prokaryotic host cell a circular first DNA molecule which is capable of being replicated in said host cell, and introducing a second DNA molecule comprising a first and a second region of sequence homology to a third and fourth region, respectively, on the first DNA molecule, said host cell being capable of performing homologous recombination, such that a recombinant DNA molecule is made, said recombinant DNA molecule comprising the first DNA molecule wherein the sequences between said third and fourth regions have been replaced by sequences between the first and second regions of the second DNA molecule, wherein a second DNA molecule is introduced into the host cell in a form which allows recombination without further modification, and wherein the homologous recombination occurs by recE- and recT-mediated gene recombination.

37. The method according to claim 36, further comprising detecting the recombinant DNA molecule.

38. A method for making a recombinant DNA molecule comprising introducing into a prokaryotic host cell, containing a chromosomal first DNA molecule, a second DNA molecule comprising a first and a second region of sequence homology to a third and a fourth region, respectively, on the host chromosomal first DNA molecule, said host cell being capable of performing homologous recombination, such that a recombinant DNA molecule is made, said recombinant DNA molecule comprising the chromosomal first DNA molecule wherein the sequences between said third and fourth regions have been replaced by sequences between the first and second regions of the second DNA molecule, wherein a second DNA molecule is introduced into the host cell in a form which allows recombination without further modification, and wherein the homologous recombination occurs by recE- and recT-mediated gene recombination.

39. The method according to claim 38, further comprising detecting the recombinant DNA molecule.

40. The method according to claim 36, wherein the host cell expresses RecE, RecT, λRedα and λRedβproteins.

41. A method for cloning DNA molecules comprising the steps of:
   (a) contacting in vitro a first DNA molecule with a second DNA molecule comprising at least two regions of sequence homology to regions on the first DNA molecule, in the presence of RecE and RecT proteins and under conditions for promoting homologous recombination between said first and second DNA molecules; and
   (b) selecting a DNA molecule in which homologous recombination between said first and second DNA molecules has occurred, and wherein the homologous recombination occurs by recE- and recT-mediated gene recombination.

42. method for making a recombinant DNA molecule comprising contacting in vitro a first DNA molecule with a second DNA molecule comprising a first and a second region of sequence homology to a third and a fourth region on the first DNA molecule, in the presence of RecE and RecT proteins and under conditions in which homologous recombination can occur, such that a recombinant DNA molecule is made, said recombinant DNA molecule comprising the first DNA molecule wherein the sequences between said third and fourth regions have been replaced by sequences between the first and second regions of the second DNA molecule, and wherein the homologous recombination occurs by recE- and recT-mediated gene recombination.

43. A reagent kit for cloning comprising
   (a) a host cell,
   (b) means of expressing recE and recT genes in said host cell, and
   (c) a recipient cloning vehicle capable of being replicated in said cell wherein said recipient cloning vehicle is a circular DNA molecule.

44. The reagent kit according to claim 43, wherein the means (b) comprise a vector system capable of expressing the recE and recT genes in the host cell.

45. The reagent kit according to claim 43, wherein the recE and recT genes are selected from the group consisting of E. coli recE, E. coli recT, phage λredα and phage λredβ.

46. A reagent kit for cloning comprising
   (a) a source for RecE and RecT proteins and
   (b) a recipient cloning vehicle capable of being propagated in a host cell, wherein said recipient cloning vehicle is a circular DNA molecule.

47. The reagent kit according to claim 46, further comprising a host cell suitable for propagating said recipient cloning vehicle.

48. The reagent kit according to claim 46, wherein said RecE and RecT proteins are selected from the group consisting of E. coli RecE, E. coli RecT, phage λRedα and phage λRedβ.

49. The reagent kit according to claim 43, further comprising means for expressing a site specific recombinase in said host cell.

50. The reagent kit according to claim 43, further comprising nucleic acid amplification primers comprising a region of homology to said recipient cloning vehicle.

51. A reagent kit for cloning comprising first and second DNA amplification primers and a recipient cloning vehicle that is a circular DNA molecule, said first DNA amplification primer having a first region of sequence homology to a third region on the circular recipient cloning vehicle, and said second DNA amplification primer having a second region of sequence homology to a fourth region on the circular recipient cloning vehicle.

52. The reagent kit of claim 51, further comprising a prokaryotic host cell for performing homologous recombination.

53. The reagent kit of claim 51, further comprising a means of expressing RecE and RecT proteins or Redα and Redβ proteins.

54. The reagent kit according claim 51, wherein the means comprises a vector system capable of expressing the recE and recT genes in the host cell.

55. The reagent kit according claim 51, further comprising a phenotypic marker located in the recipient cloning vehicle between the third and fourth regions of sequence homology.

56. The reagent kit according claim 51, wherein the recipient cloning vehicle further comprises a recognition site for a site-specific recombinase on the recipient cloning vehicle between the third and fourth regions of sequence homology.

57. The reagent kit of claim 56, further comprising means for expressing a site-specific recombinase in said host cell.

58. A vector system capable of expressing recE and recT genes in a host cell.

59. The vector system of claim 58, further capable of expressing a recBC inhibitor gene.

60. The vector system of claim 59, capable of expressing the recE and recT genes and the recBC inhibitor gene under control by a regulatable promoter.

61. The method of claim 14, comprising a vector system capable of expressing recE and recT genes and recBC inhibitor gene under control by a regulatable promoter.

* * * * *